(12) United States Patent
Amin

(10) Patent No.: US 10,729,790 B2
(45) Date of Patent: Aug. 4, 2020

(54) MOTOR NEURON-SPECIFIC EXPRESSION VECTORS

(71) Applicant: SALK INSTITUTE FOR BIOLOGICAL STUDIES, La Jolla, CA (US)

(72) Inventor: Neal Dilip Amin, La Jolla, CA (US)

(73) Assignee: SALK INSTITUTE FOR BIOLOGICAL STUDIES, La Jolla, CA (US)

( * ) Notice: Subject to any disclaimer, the term of this patent is extended or adjusted under 35 U.S.C. 154(b) by 257 days.

(21) Appl. No.: 15/576,587

(22) PCT Filed: May 24, 2016

(86) PCT No.: PCT/US2016/033914
§ 371 (c)(1),
(2) Date: Nov. 22, 2017

(87) PCT Pub. No.: WO2016/191418
PCT Pub. Date: Dec. 1, 2016

(65) Prior Publication Data
US 2018/0264140 A1    Sep. 20, 2018

Related U.S. Application Data

(60) Provisional application No. 62/166,677, filed on May 26, 2015, provisional application No. 62/168,755, filed on May 30, 2015, provisional application No. 62/268,357, filed on Dec. 16, 2015.

(51) Int. Cl.
| | |
|---|---|
| *A61K 48/00* | (2006.01) |
| *A01K 67/027* | (2006.01) |
| *A61K 31/7088* | (2006.01) |
| *C12N 15/85* | (2006.01) |
| *C12N 15/113* | (2010.01) |
| *A61K 31/7105* | (2006.01) |
| *A61K 31/713* | (2006.01) |
| *A61P 25/28* | (2006.01) |

(52) U.S. Cl.
CPC ...... *A61K 48/0066* (2013.01); *A01K 67/0275* (2013.01); *A01K 67/0276* (2013.01); *A61K 31/7088* (2013.01); *A61K 31/713* (2013.01); *A61K 31/7105* (2013.01); *A61K 48/0016* (2013.01); *A61P 25/28* (2018.01); *C12N 15/113* (2013.01); *C12N 15/85* (2013.01); *A01K 2217/052* (2013.01); *A01K 2217/075* (2013.01); *A01K 2227/105* (2013.01); *A01K 2227/50* (2013.01); *A01K 2267/0318* (2013.01); *A01K 2267/0393* (2013.01); *C12N 2310/113* (2013.01); *C12N 2310/20* (2017.05); *C12N 2830/008* (2013.01)

(58) Field of Classification Search
None
See application file for complete search history.

(56) References Cited

U.S. PATENT DOCUMENTS

| | | |
|---|---|---|
| 4,980,286 A | 12/1990 | Morgan et al. |
| 5,139,941 A | 8/1992 | Muzyczka et al. |
| 5,252,479 A | 10/1993 | Srivastava |
| 5,436,146 A | 7/1995 | Shenk et al. |
| 5,753,500 A | 5/1998 | Shenk et al. |
| 2015/0023927 A1* | 1/2015 | Eggan .................. C12N 5/0619 424/93.7 |
| 2018/0064748 A1* | 3/2018 | Hornstein .............. A61K 45/06 |

FOREIGN PATENT DOCUMENTS

| | | |
|---|---|---|
| WO | WO-9206180 A1 | 4/1992 |
| WO | WO-9220316 A2 | 11/1992 |
| WO | WO-9222635 A1 | 12/1992 |
| WO | WO-9314188 A1 | 7/1993 |
| WO | WO-9320221 A1 | 10/1993 |
| WO | WO-9408598 A1 | 4/1994 |
| WO | WO-9412649 A2 | 6/1994 |
| WO | WO-9709441 A2 | 3/1997 |
| WO | WO-9822144 A2 | 5/1998 |
| WO | WO-2016191418 A1 | 12/2016 |

OTHER PUBLICATIONS

Genbank Accession No. NC_000077, earliest publication date 2009. 129 pages.*
Alaynick et al. SnapShot: spinal cord development. Cell 146:178-178.e1 (2011).
Amin et al. Loss of motoneuron-specific microRNA-218 causes systemic neuromuscular failure. Science 350:1525-1529 (2015).
Anson. The use of retroviral vectors for gene therapy—what are the risks? A review of retroviral pathogenesis and its relevance to retroviral vector-mediated gene delivery. Genet Vaccines Ther 2(1):9 (2004).
Azim et al. Skilled reaching relies on a V2a propriospinal internal copy circuit. Nature 508:357-363 (2014).
Bartel. MicroRNAs: target recognition and regulatory functions. Cell 136:215-233 (2009).

(Continued)

*Primary Examiner* — Christopher M Babic
*Assistant Examiner* — Kimberly A. Aron
(74) *Attorney, Agent, or Firm* — Wilson Sonsini Goodrich & Rosati

(57) ABSTRACT

The present disclosure relates to nucleic acid promoter sequences that are able to specifically express genes operatively linked to the promoter in brainstem and spinal motor neuron cells, and to methods for using such promoters to selectively express genes in motor neurons in vitro and in vivo. It is based, at least in part, on the discovery that the nucleic acid of SEQ ID NO: 1 functioned as a motor neuron-specific promoter and was successful in expressing transgenes in motor neuron cells in vivo. The present disclosure also relates to compositions that can increase the activity or expression level of miR-218 and to compositions that can decrease the expression of miR-218 target nucleic acids.

7 Claims, 79 Drawing Sheets

Specification includes a Sequence Listing.

(56) References Cited

OTHER PUBLICATIONS

Boesen et al. Circumvention of chemotherapy-induced myelosuppression by transfer of the mdr1 gene. Biotherapy 6:291-302 (1994).
Bout et al. Lung gene therapy: in vivo adenovirus-mediated gene transfer to rhesus monkey airway epithelium. Human Gene Therapy 5:3-10 (1994).
Brophy et al. Bioavailability of oral dexamethasone during high dose steroid therapy in neurological patients. Eur J Clin Pharmacol 24:103-108 (1983).
Cheah et al. Riluzole, neuroprotection and amyotrophic lateral sclerosis. Curr Aled Chem 17:942-1199 (2010).
Cline. Perspectives for gene therapy: inserting new genetic information into mammalian cells by physical techniques and viral vectors. Pharmac Ther 29:69-92 (1985).
Clowes et al. Long-term biological response of injured rat carotid artery seeded with smooth muscle cells expressing retrovirally introduced human genes. J Clin Invest 93:644-651 (1994).
Cotton et al. Receptor-mediated transport of DNA into eukaryotic cells. Methods Enzymol 217:618-644 (1993).
Darabid et al. Neuromuscular synaptogenesis: coordinating partners with multiple functions. Nat Rev Neurosci 15:703-718 (2014).
Dillon. Regulating gene expression in gene therapy. Trends Biotechnol 11(5):167-173 (1993).
Dodet. Commercial prospects for gene therapy—a company survey. Trends Biotechnol 11(5):182-189 (1993).
Dzau et al. Gene therapy for cardiovascular disease. Trends Biotechnol 11(5):205-210 (1993).
Eom et al. Transglutaminase II/MicroRNA-218/-181a Loop Regulates Positive Feedback Relationship between Allergic Inflammation and Tumor Metastasis. J Bio Chem 289:29483-29505 (2014).
Findeis et al. Targeted delivery of DNA for gene therapy via receptors. Trends Biotechnol 11(5):202-205 (1993).
Fischer et al. Amyotrophic lateral sclerosis is a distal axonopathy: evidence in mice and man. Exp Neurol 185:232-240 (2004).
Fotherby. Bioavailability of orally administered sex steroids used in oral contraception and hormone replacement therapy. Contraception 54:59-69 (1996).
Friedmann. Gene therapy for disorders of the nervous system. Trends Biotechnol. 11:192-197 (1993).
Friedmann. Gene therapy—a new kind of medicine. Trends Biotechnol. 11(5):156-159 (1993).
Garcia et al. Weak seed-pairing stability and high target-site abundance decrease the proficiency of Isy-6 and other microRNAs. Nat Struct Mol Biol 18:1139-1146 (2011).
Goldspiel et al. Human gene therapy. Clin Pharm 12:488-505 (1993).
Groning et al. Three-dimensional solubility parameters and their use in characterising the permeation of drugs through the skin. Pharmazie 51:337-341 (1996).
Grossman et al. Retroviruses: delivery vehicle to the liver. Curr Opin Genet Dev 3:110-114 (1993).
Haramati et al. miRNA malfunction causes spinal motor neuron disease. PNAS USA 107:13111-13116 (2010).
Herranz et al. MicroRNAs and gene regulatory networks: managing the impact of noise in biological systems. Genes Dev 24:1339-1344 (2010).
Hidalgo-Aragones et al. Pharmacokinetics of oestrone-3-O-sulphamate. J Steroid Biochem Mol Biol 58:611-617 (1996).
High. The gene therapy journey for hemophilia: are we there yet? Blood 120(23):4482-4487 (2012).
Jinek et al. A programmable dual-RNA-guided DNA endonuclease in adaptive bacterial immunity. Science 337:816-821 (2012).
Johnson et al. Permeation of steroids through human skin. J Pharm Sci 84:1144-1146 (1995).
Kapsimali et al. MicroRNAs show a wide diversity of expression profiles in the developing and mature central nervous system. Genome Biol 8:R173 (2007).
Kawahara et al. TDP-43 promotes microRNA biogenesis as a component of the Drosha and Dicer complexes. PNAS USA 109:3347-3352 (2012).
Kiem et al. Retrovirus-mediated gene transduction into canine peripheral blood repopulating cells. Blood 83:1467-1473 (1994).
Koller et al. Inactivating the beta 2-microglobulin locus in mouse embryonic stem cells by homologous recombination. PNAS USA 86:8932-8935 (1989).
Kozarsky et al. Gene therapy: adenovirus vectors. Curr Opin Genet Dev 3:499-503 (1993).
Kron et al. Adenovirus vectors and subviral particles for protein and peptide delivery. Curr Gene Tiler 12(5):362-73 (2012).
Kwan et al. Activity of Hb9 interneurons during fictive locomotion in mouse spinal cord. J Neurosci 29:11601-11613 (2009).
Li et al. Enhancer of Zeste Homolog 2 Silences MicroRNA-218 in Human Pancreatic Ductal Adenocarcinoma Cells by Inducing Formation of Heterochromatin. Gastroenterology 144:1086-1097 (2013).
Little et al. Conserved modularity and potential for alternate splicing in mouse and human Slit genes. Int J Dev Bio 46:385-391 (2002).
Liu et al. Spinal muscular atrophy patient-derived motor neurons exhibit hyperexcitability. Sci Rep 5:12189 (2015).
Loeffler et al. Gene transfer into primary and established mammalian cell lines with lipopolyamine-coated DNA. Meth Enzymol 217:599-618 (1993).
Long et al. Conserved roles for Slit and Robo proteins in midline commissural axon guidance. Neuron 42:213-223 (2004).
Lu et al. MiR-218 mediates tumorigenesis and metastasis: Perspectives and implications. Exp Cell Res 334:173-182 (2015).
Ma et al. Dual branch-promoting and branch-repelling actions of Slit/Robo signaling on peripheral and central branches of developing sensory axons. J Neurosci 27:6843-6851 (2007).
Mah et al. Virus-based gene delivery systems. Clin Pharmacokinet 41(12):901-911 (2002).
Makeyev et al. The microRNA miR-124 promotes neuronal differentiation by triggering brain-specific alternative pre-mRNA splicing, Molecular Cell, 27(3):435-448 (2007).
Marson et al. Connecting microRNA genes to the core transcriptional regulatory circuitry of embryonic stem cells. Cell 134:521-533 (2008).
Mastrangeli et al. Diversity of airway epithelial cell targets for in vivo recombinant adenovirus-mediated gene transfer. J Clin Invest 91:225-234 (1993).
Mazzoni et al. Synergistic binding of transcription factors to cell-specific enhancers programs motor neuron identity. Nat Neurosci 16, 1219-1227 (2013).
McCarty et al. Integration of adeno-associated virus (AAV) and recombinant AAV vectors. Annu Rev Genet. 38:819-845 (2004).
McConnell et al. Biology of adenovirus and its use as a vector for gene therapy. Hum Gene Ther. 15(11):1022-1033 (2004).
Miller et al. Use of retroviral vectors for gene transfer and expression. Meth. Enzymol. 217:581-599 (1993).
Mitani et al. Delivering therapeutic genes—matching approach and application Trends Biotechnol 11:162-166 (1993).
Molyneaux et al. DeCoN: genome-wide analysis of in vivo transcriptional dynamics during pyramidal neuron fate selection in neocortex. Neuron 85:275-288 (2015).
Morgan et al. Human gene therapy. Ann Rev Biochem 62:191-217 (1993).
Morlando et al. FUS stimulates microRNA biogenesis by facilitating co-transcriptional Drosha recruitment. EAJBO J 31:4502-4510 (2012).
Mulligan. The basic science of gene therapy. Science 260(5110):926-932 (1993).
Nabel et al. Direct gene transfer for immunotherapy and immunization. Trends Biotechnol 11(5):211-215 (1993).
Paez-Colasante et al. Amyotrophic lateral sclerosis: mechanisms and therapeutics in the epigenomic era. Nat Rev Neurol 11:266-279 (2015).
PCT/US2016/033914 International Preliminary Report on Patentability dated Dec. 7, 2017.
PCT/US2016/033914 International Search Report and Written Opinion dated Sep. 13, 2016.

(56) References Cited

OTHER PUBLICATIONS

Pittelkow et al. New techniques for the in vitro culture of human skin keratinocytes and perspectives on their use for grafting of patients with extensive burns. Mayo Clinic Proc. 61:771-777 (1986).
Porada et al. Treatment of Hemophilia A in Utero and Postnatally using Sheep as a Model for Cell and Gene Delivery. J Genet Syndr Gene Ther S1 (2012).
Porteous et al. How relevant are mouse models for human diseases to somatic gene therapy? Trends Biotechnol 11(5):173-181 (1993).
Punnamoottil et al. Motor Neuron-Expressed MicroRNAs 218 and Their Enhancers Are Nested Within Introns of Slit2/3 Genes. Genesis 53:321-328 (2015).
Rheinwald. Chapter 15: Serial cultivation of normal human epidermal keratinocytes. Meth. Cell Bio 21A:229-254 (1980).
Robinson. Gene therapy—proceeding from laboratory to clinic. Trends Biotech 11:155 (1993).
Rohatagi et al. Pharmacokinetic interaction between endogenous cortisol and exogenous corticosteroids. Pharmazie 50:610-613 (1995).
Rosen et al. Mutations in Cu/Zn superoxide dismutase gene are associated with familial amyotrophic lateral sclerosis. Nature 362(6415):59-62 (1993).
Rosenfeld et al. Adenovirus-Mediated Transfer of A Recombinant alpha 1-Antitrypsin Gene To The Lung Epithelium in Vivo. Science 252:431-434 (1991).
Rosenfeld et al. In vivo transfer of the human cystic fibrosis transmembrane conductance regulator gene to the airway epithelium. Cell 68:143-155 (1992).
Salmons et al. Targeting of retroviral vectors for gene therapy. Human Gene Therapy. 4:129-141 (1993).
Scott et al. Viral vectors for gene transfer of micro-, mini-, or full-length dystrophin. Neuromuscul. Disord. 12(Suppl 1):S23-9 (2002).
Sikora. Gene therapy for cancer. Trends Biotechnol 11(5):197-201 (1993).
Stemple et al. Isolation of a stem cell for neurons and glia from the mammalian neural crest. Cell 71:973-985 (1992).
Thiebes et al. miR-218 is essential to establish motor neuron fate as a downstream effector of Isl1-Lhx3. Nat Commun 6:7718 (2015).
Tolstoshev. Gene Therapy, Concepts, Current Trials and Future Directions. Ann. Rev. Pharmacol. Toxicol. 32:573-596 (1993).
Tsang et al. MicroRNA-mediated feedback and feedforward loops are recurrent network motifs in mammals. Mol Cell 26:753-767 (2007).
Turgeon et al. Interpreting neonatal lethal phenotypes in mouse mutants: insights into gene function and human diseases. Physiol Rev 89:1-26 (2009).
Van Dongen et al. Detecting microRNA binding and siRNA off-target effects from expression data. Nat Methods 5:1023-1025 (2008).
Vidigal et al. The biological functions of miRNAs: lessons from in vivo studies. Trends Cell Biol 25:137-147 (2015).
Volonte et al. MicroRNAs: newcomers into the ALS picture. CNS Neurol Disord Drug Targets 14:194-207 (2015).
Wainger et al. Intrinsic membrane hyperexcitability of amyotrophic lateral sclerosis patient-derived motor neurons. Cell Rep 7:1-11 (2014).
Walsh et al. Gene therapy for human hemoglobinopathies. Proc. Soc. Exp. Biol. Med. 204:289-300 (1993).
Wang et al. A packaging cell line for propagation of recombinant adenovirus vectors containing two lethal gene-region deletions. Gene Ther 2(10):775-783 (1995).
Wang et al. One-step generation of mice carrying mutations in multiple genes by CRISPR/Cas-mediated genome engineering. Cell 153 (4):910-918 (2013).
Williamson. From genome mapping to gene therapy. Trends Biotechnol 11(5):159-161 (1993).
Wivel. Regulatory considerations for gene-therapy strategies and products. Trends Biotechnol 11(5):189-191 (1993).
Wu et al. Delivery systems for gene therapy. Biotherapy 3:87-95 (1991).
Yi et al. Current advances in retroviral gene therapy. Curr Gene Ter 11(3):218-228 (2011).
Zhang et al. V3 spinal neurons establish a robust and balanced locomotor rhythm during walking. Neuron 60:84-96 (2008).
Zhong et al. Development of Novel Recombinant AAV Vectors and Strategies for the Potential Gene Therapy of Hemophilia. J Genet Syndr Gene Ther S1 (2012).
Zijlstra et al. Germ-line transmission of a disrupted β2-microglobulin gene produced by homologous recombination in embryonic stem cells. Nature 342:435¬-438 (1989).

* cited by examiner

```
taaacgcccc aatttgctac ttatcaaata gtatacattt ttggctcaga aaaaaacctg   60
atgtctgtat attacttctc aactaaaatc cctcagtcct taactggcat gtgtattagt  120
caaggcatct ttgagaaggg cattatttcc ctacacttag gatggggaaa gagaaattaa  180
aaaggaatcc taaaataggt gcatttaatt ctcccaatt taaatgtaag tggtgcgtct   240
tttaggcaat aatgatatgc cttttagtcc tccattacaa acacttccat cgatgaattt  300
ccttaatgtt gatgatggtt agtgcagttt gagggaatct gtatttattc agaaaatgtt  360
cccatagaat gacctaccag atgggccacg taacaatgca tggagacatc aaaccaccac  420
agacatttgg tgcttagaat aataaaaaga ctataaaatt agattagttg agtctaattt  480
ggaattggta tattccctac gcaccctcac cgctcttggg cagataaagc cttgagattt  540
agcgctgtgt caaagccaag actgtaactt ccagtaaaag ggagccgagg gaggggagc   600
ttgctgggag gtcgcggagg gcagagcagt gacctccaat gatttacagg cctttagctt  660
aatgaaattg tttcagtgac atgacagtaa gagctcgtaa tggattggat gccctaatgt  720
aatgaaatta ctcccttctg cctaaaaaaa aaaaatgcg caattaatat ttactgagac    780
ctgacagcct ttggtgcgct cgctcgcctg tgtagttccc tcagacagtc agagagaaga  840
gacagagcag cgtggcagac aggcgggctc tgcaggagct cctggcaggg acaagcagag  900
cctgcaag                                                            908
(SEQ ID NO:1).
```

FIG. 1

E11.5 transgenic mouse line expressing 908bp miR-218-promoter:eGFP

Brightfield image eGFP fluorescence

- Motor columns/cell bodies (arrow)
- Motor axons (bracket)
- Brainstem motor nuclei (arrowhead)

E12.5 transgenic mouse line expressing 7.6 kb miR-218-promoter:eGFP
or homeobox gene (Hb9) promoter:eGFP
Brightfield
Hb9:GFP             218p:eGFP long
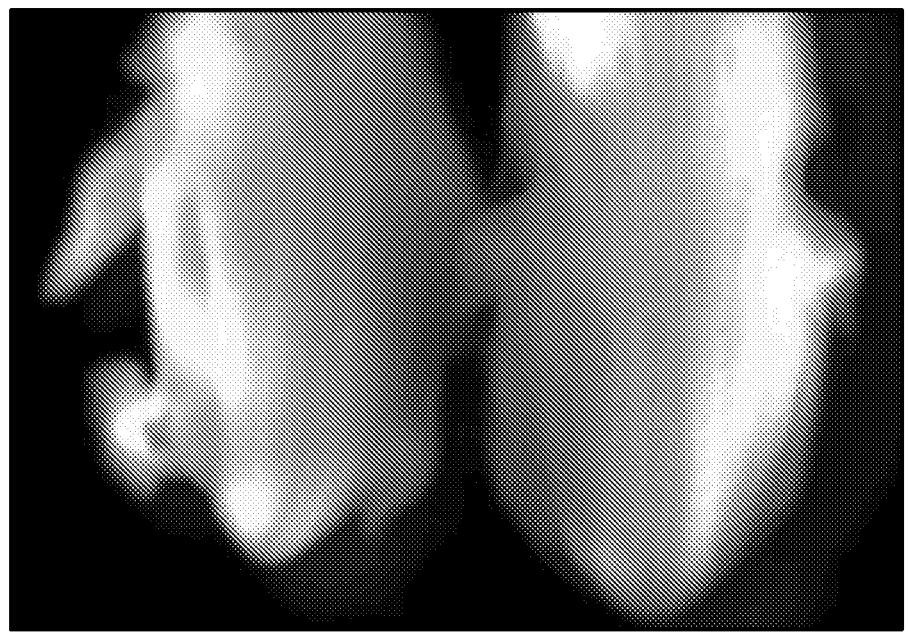
Fluorescence
Hb9:GFP             218p:eGFP long
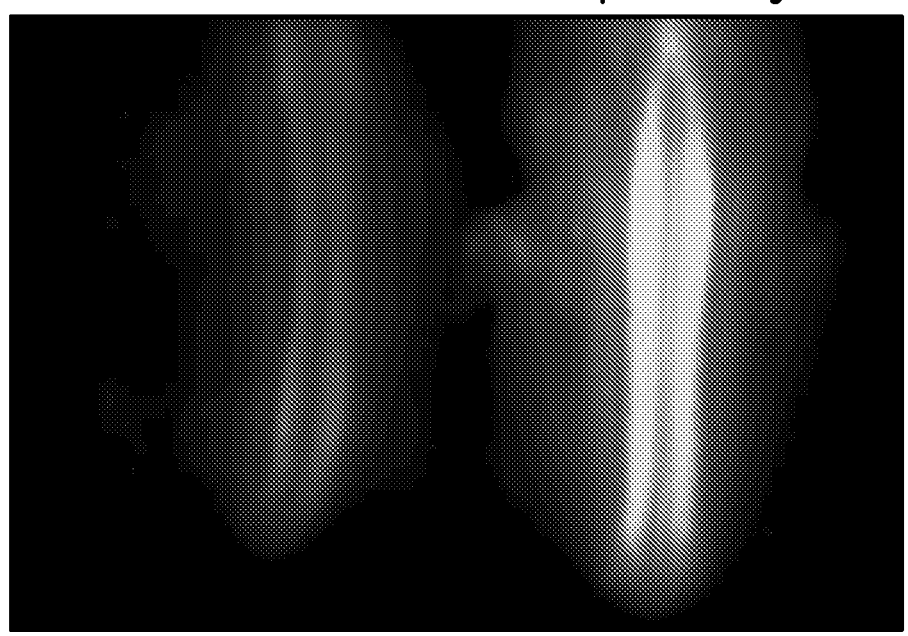
FIG. 3A E12.5 transgenic mouse line expressing 7.6 kb miR-218-promoter:eGFP
Brightfield
Fluorescence
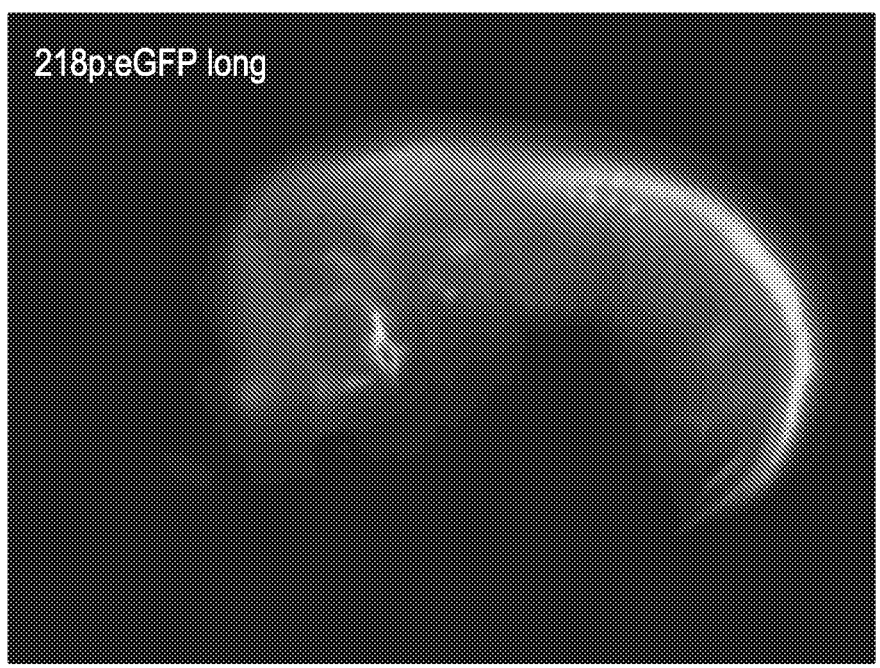
FIG. 3B E18.5 transgenic mouse line expressing 7.6 kb miR-218-promoter:eGFP

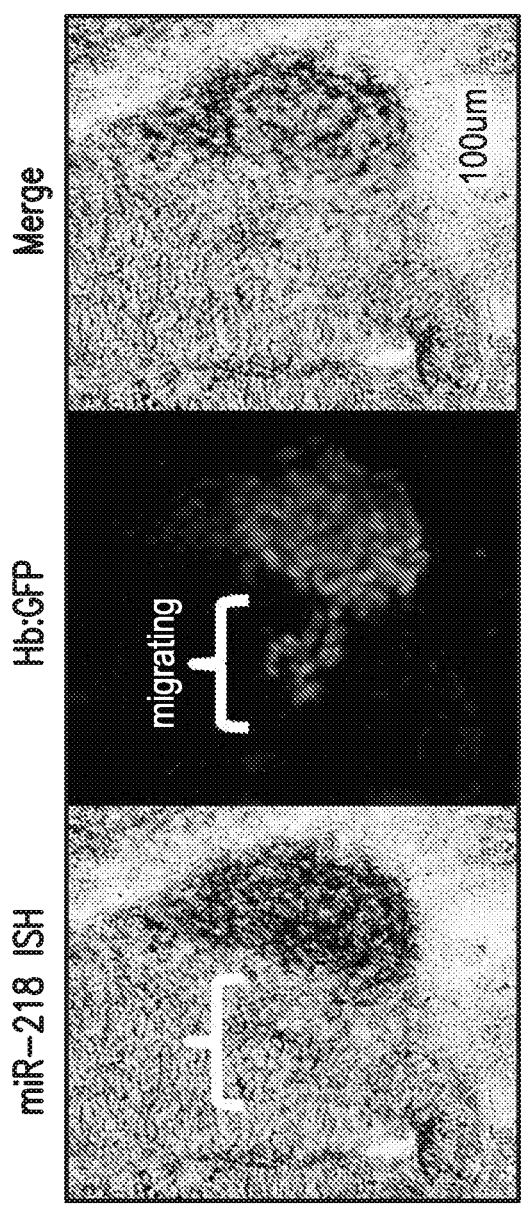
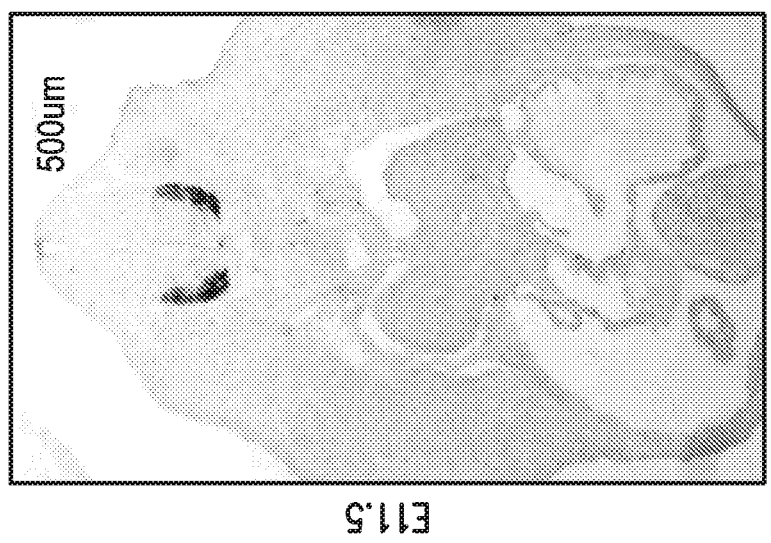
FIG. 11

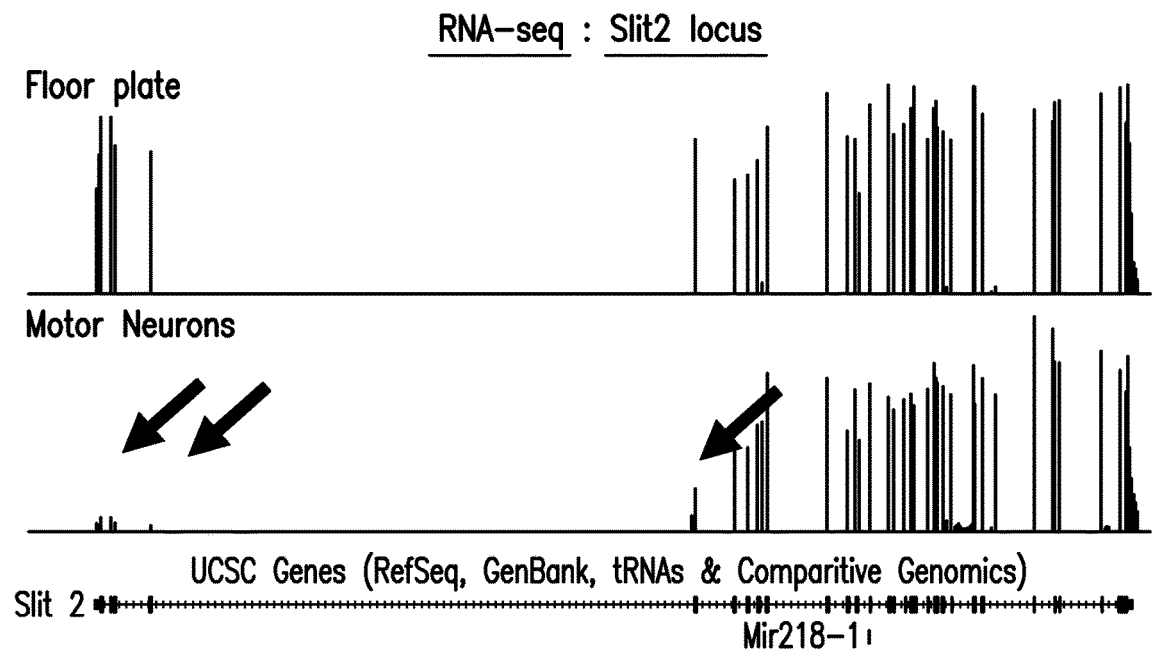
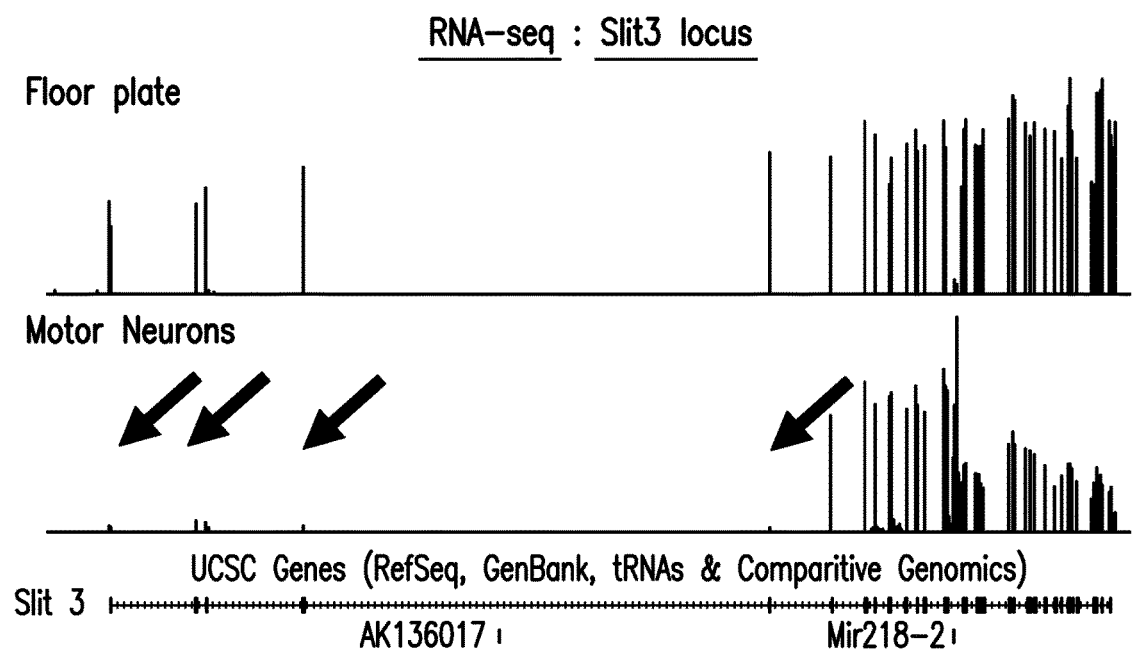
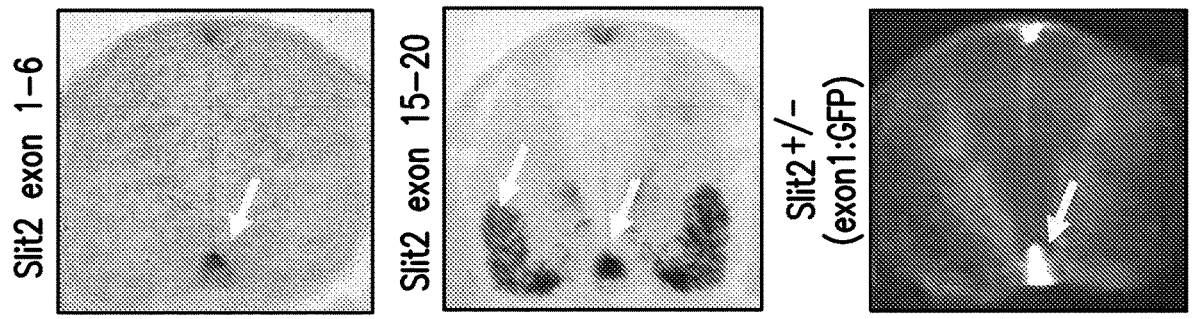
FIG. 13 Continued

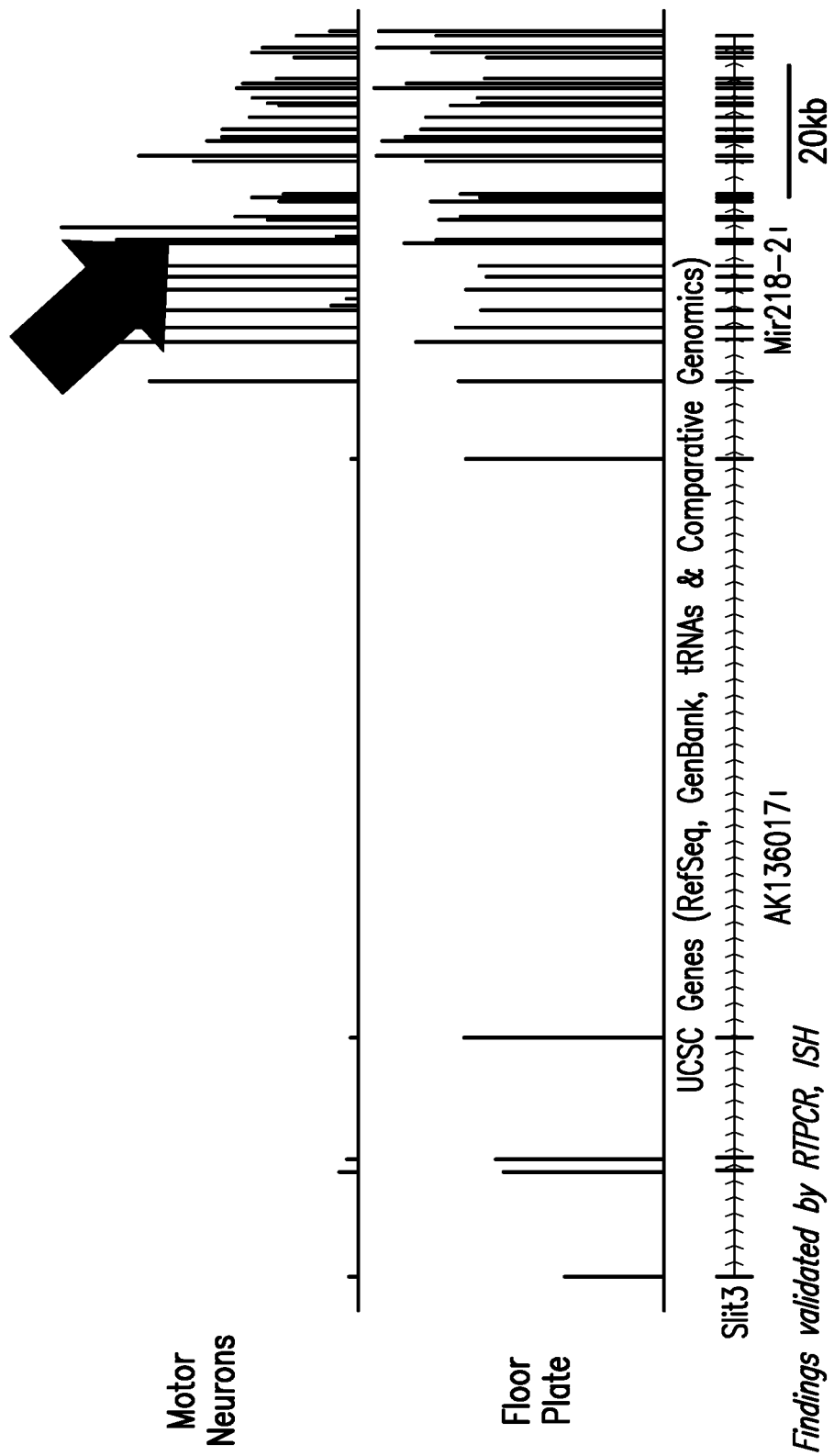

| Gene Name | Symbol | e12.5 %up | ESMN %up | TargetScan Score |
|---|---|---|---|---|
| one cut domain, family member 2 | Onecut2 | 78% | 157% | −0.786 |
| predicted gene 9514; similar to sorting nexin 4; sorting nexin 4 | Snx4 | 30% | 83% | −0.553 |
| glucuronyl C5-epimerase | Glce | 55% | 106% | −0.512 |
| solute carrier family 1 (glutamatre reuptake)-EAAT2 | Slc1a2 | 126% | 273% | −0.431 |
| synaptotagmin XIII | Syt13 | 66% | 187% | −0.417 |
| Ras association (RalGDS/AF-6) domain family member2 | Rassf2 | 63% | 70% | −0.401 |
| YEATS domain containing 4 | Yeats4 | 35% | 125% | −0.314 |
| Bmi1 polycomb ring finger oncogene | Bmi1 | 25% | 119% | −0.309 |
| expressed sequence AW146242 | Vopp1 | 66% | 65% | −0.308 |
| one cut domain, family member 3 | Onecut3 | 104% | 76% | −0.297 |
| splicing factor, arginine/serine-rich 6 | Srsf6 | 20% | 48% | −0.297 |
| cytospinA | Specc1l | 32% | 43% | −0.291 |
| guanine nucleotide binding protein (G protein), gamma 3 | Gng3 | 37% | 72% | −0.278 |
| regulator of chromosome condensation (RCC1) and BTB (POZ) domain containing protein 1 | Rcbtb1 | 33% | 103% | −0.272 |
| lysine (K)-specific demethylase 5A | Kdm5a | 26% | 31% | −0.261 |

FIG. 21 Continued

Synaptic-related indirect targets are downregulated in the absence of miR-218

| Symbol | Gene name | Function | e12.5 %down | ESMN %down |
|---|---|---|---|---|
| Nrp1 | neuropilin 1 | Glycoprotein receptor | -10% | -23% |
| Pygb | brain glycogen phosphorylase | Glycogen degradation | -11% | -20% |
| Magee1 | melanoma antigen, family E, 1 | a-dystrobrevin associated | -11% | -16% |
| Syngr3 | synaptogyrin 3 | Ca++ dependent exocytosis | -12% | -23% |
| Cplx1 | complexin 1 | SNARE complex | -12% | -24% |
| Stx1a | syntaxin 1A (brain) | SNARE complex | -12% | -30% |
| Ache | acetylcholinesterase | Acetylcholine turnover | -15% | -31% |
| Sigmar1 | sigmanon-opioid intracellular receptor 1 | ALS gene-chaperone protein | -17% | -27% |
| Adora | adenosineA1 receptor | Target of sedatives | -20% | -36% |
| Trpv2 | transient receptor potential cation channel V2 | Mechano receptor | -20% | -34% |
| Sv2c | synaptic vesicle glycoprotein 2c | NMJ localized | -24% | -27% |
| Prph | peripherin | ALS gene–Int. Filament | -32% | -38% |
| Qk | similar to Quaking protein; quaking | KO results in seizures | -41% | -40% |

FIG. 22 Continued

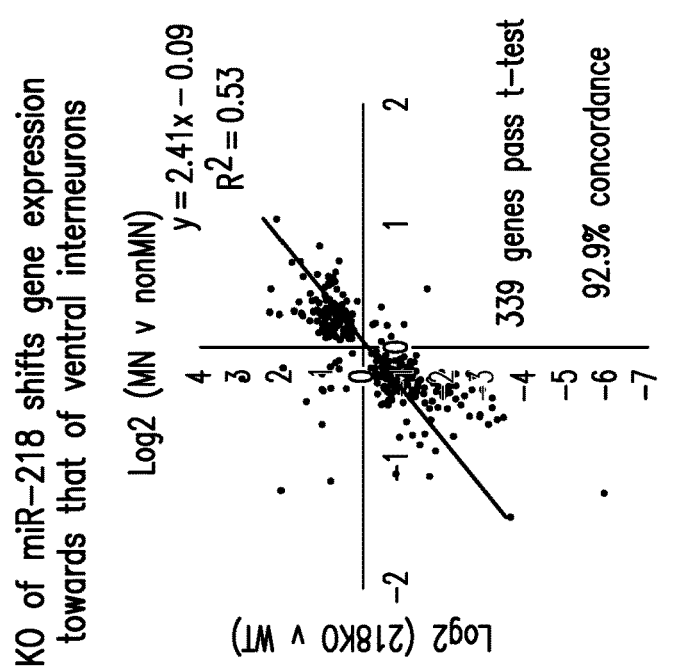
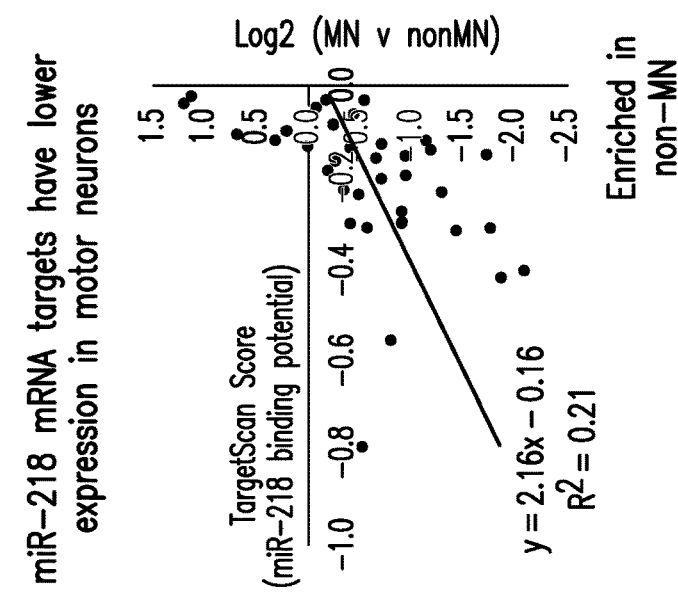
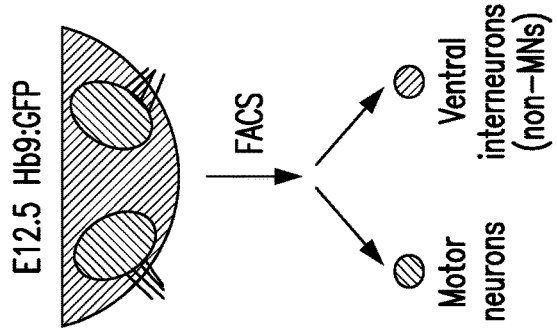
FIG. 23

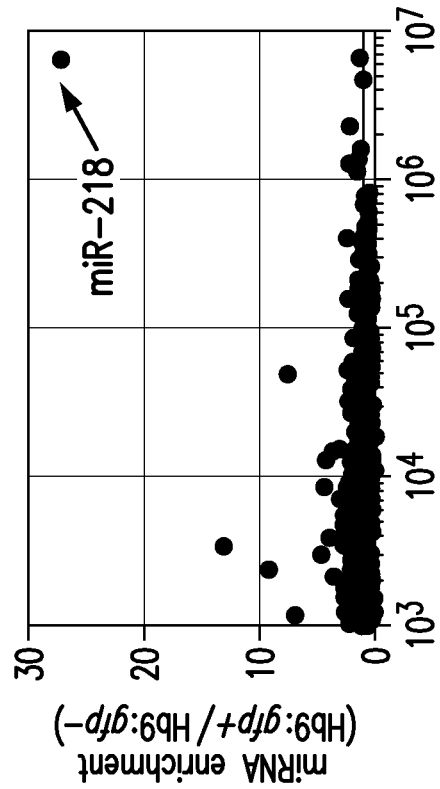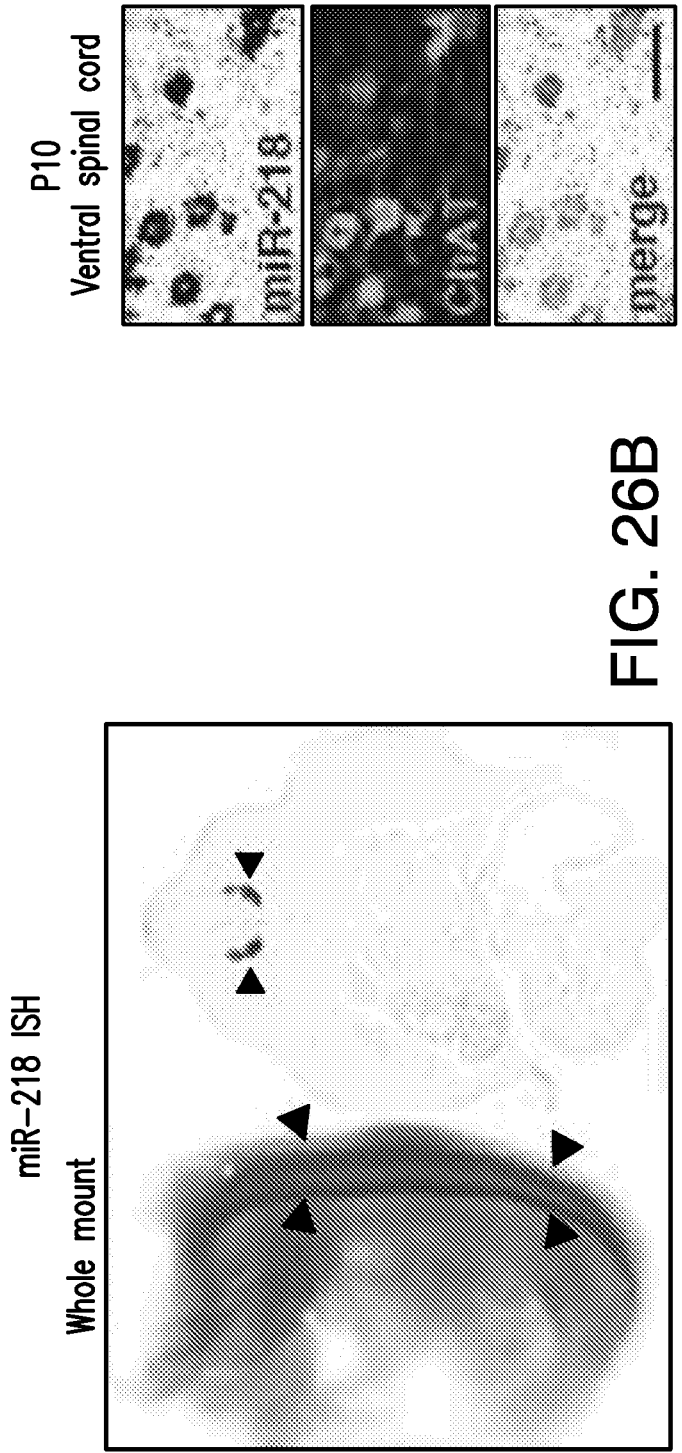
FIG. 26A
FIG. 26B
FIG. 26C

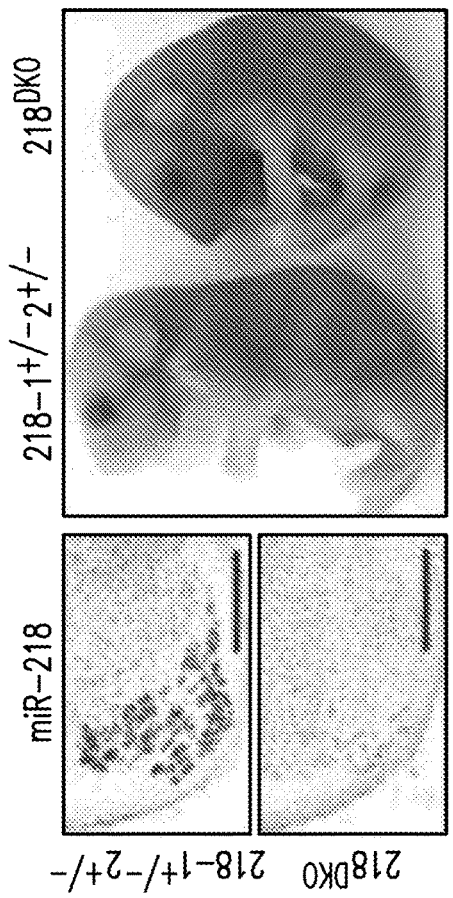
FIG. 27C
FIG. 27B
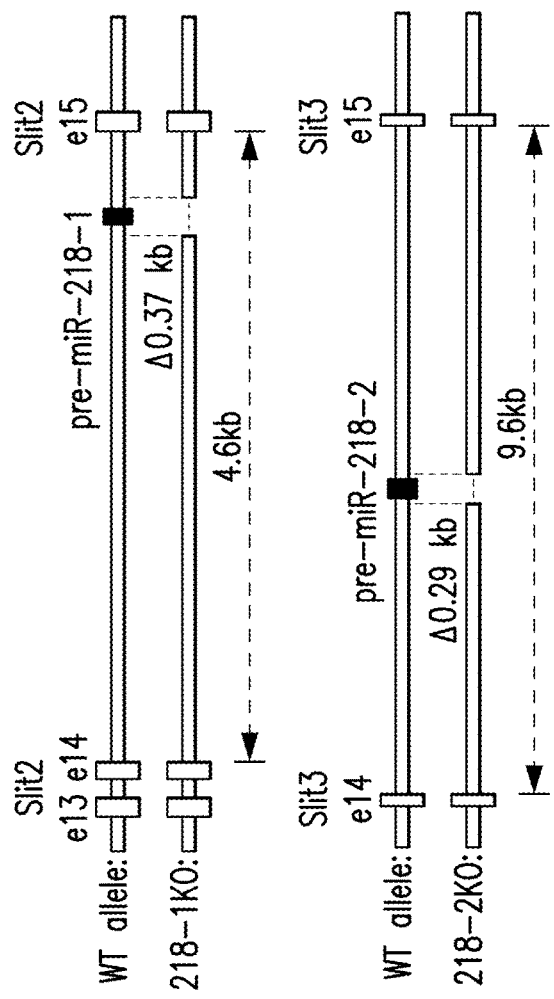
FIG. 27A

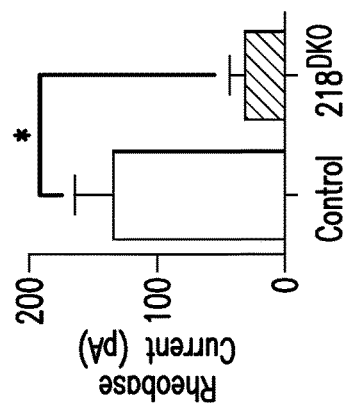
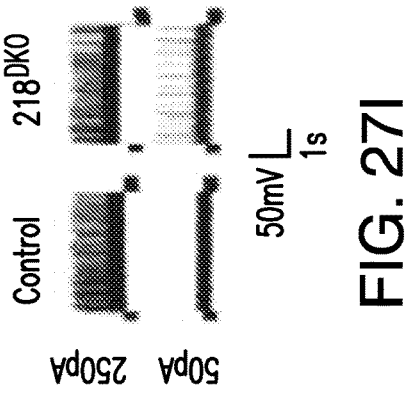
FIG. 27I
FIG. 27J
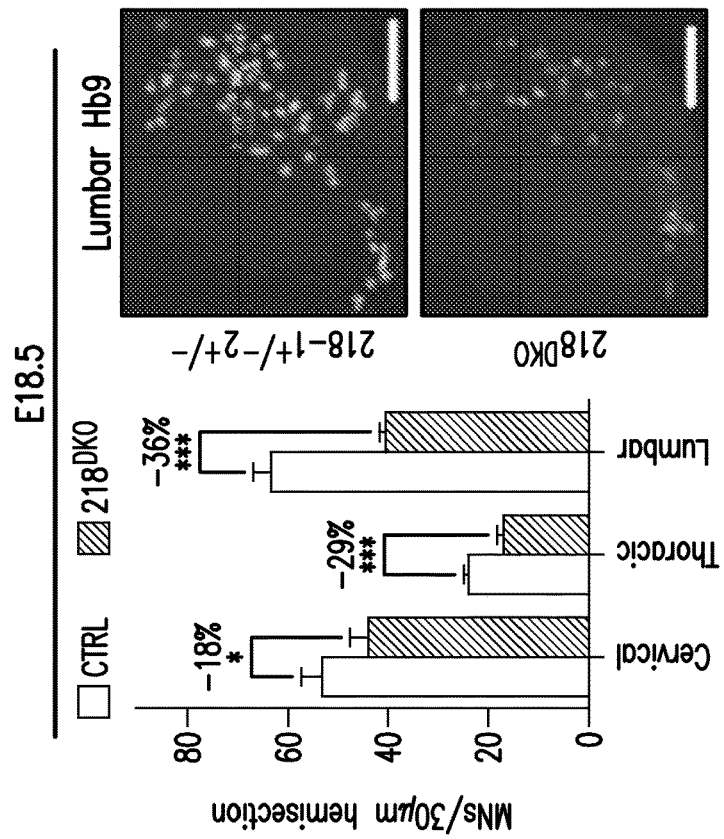
FIG. 27H
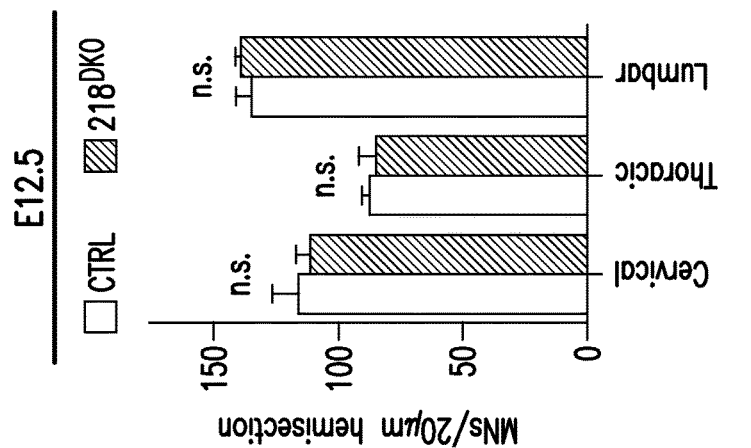
FIG. 27G

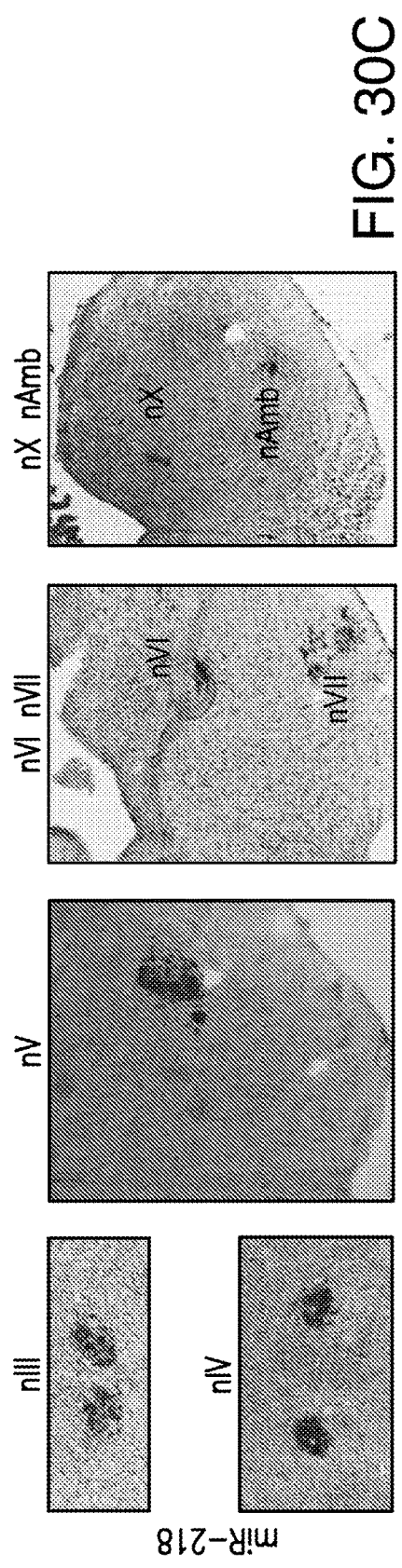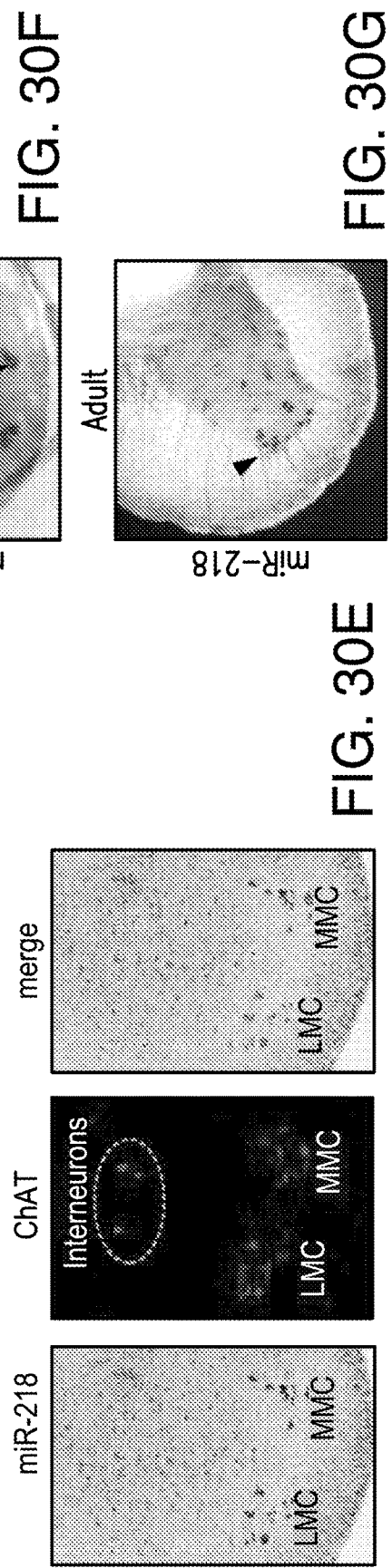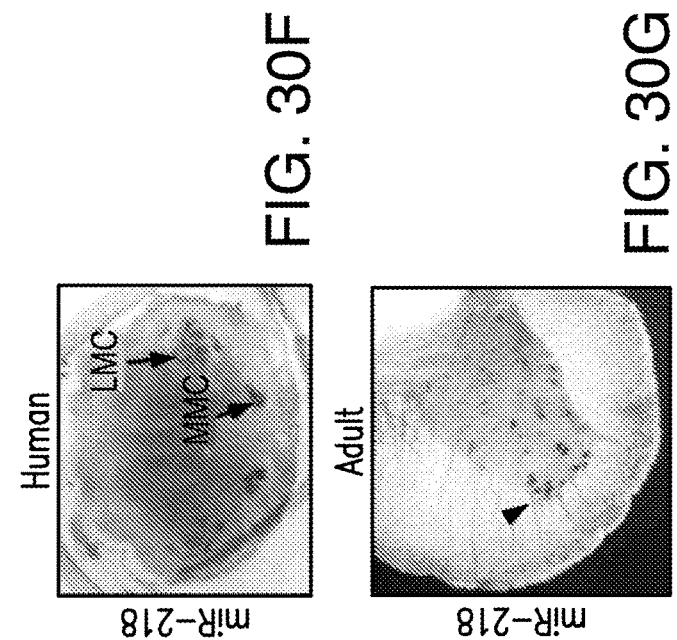

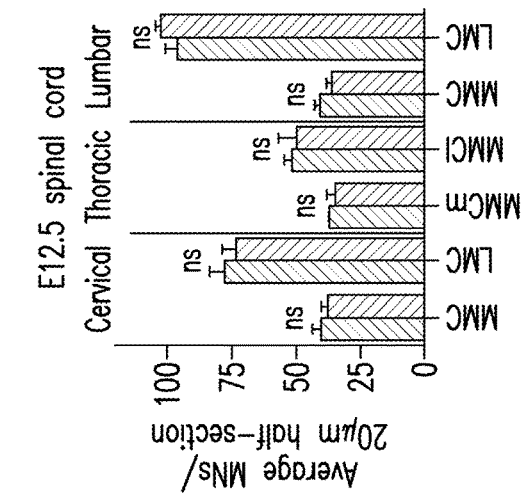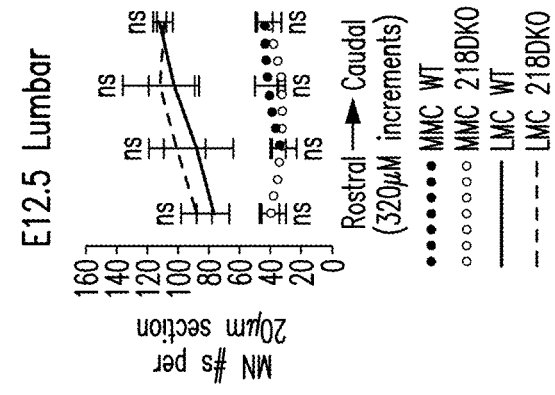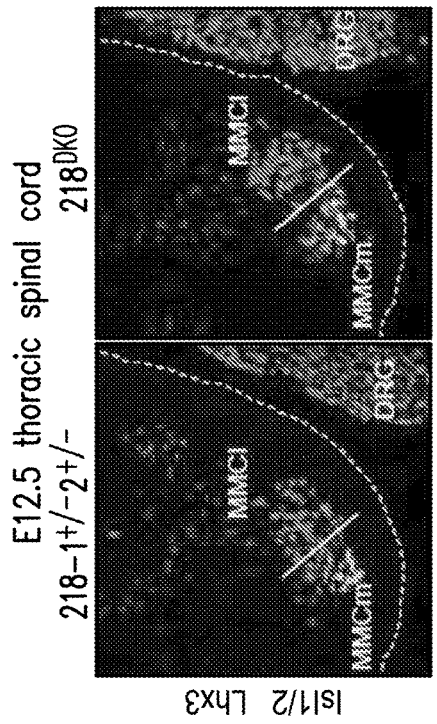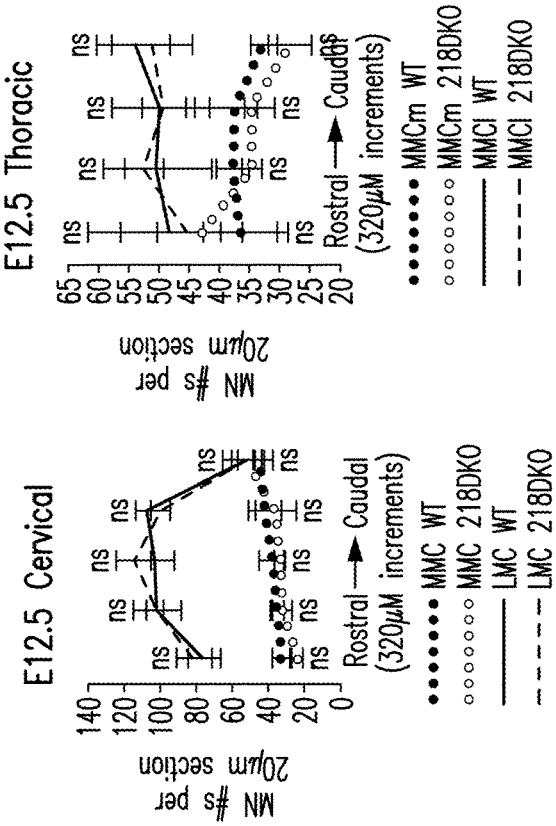

| miR-218-1$^{-/-}$2$^{+/-}$ x miR-218-1$^{-/-}$2$^{+/-}$ | | | | |
|---|---|---|---|---|
| | # pups observed | observed frequency | expected frequency | response rate to tail pinch 20min after C-section |
| miR-218-1$^{-/-}$2$^{+/+}$ | 13 | 0.29 | 0.25 | 13/13 |
| miR-218-1$^{-/-}$2$^{+/-}$ | 20 | 0.44 | 0.50 | 20/20 |
| miR-218-1$^{-/-}$2$^{-/-}$ (218$^{DKO}$) | 12 | 0.27 | 0.25 | 0/12 |

Chi Square Test, p=0.993

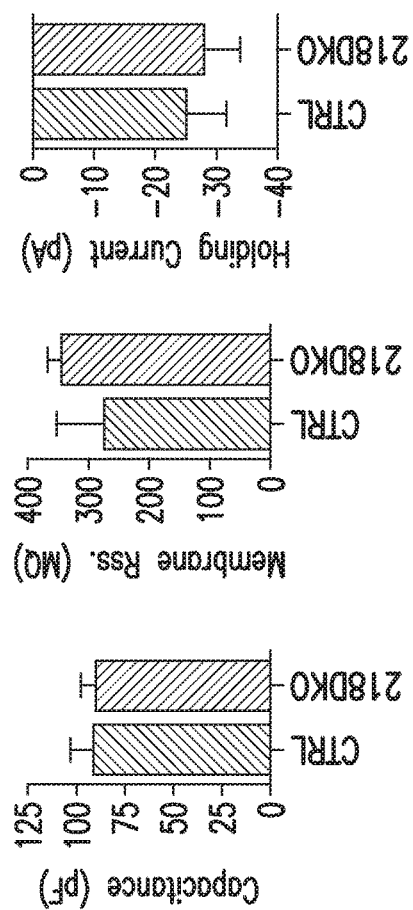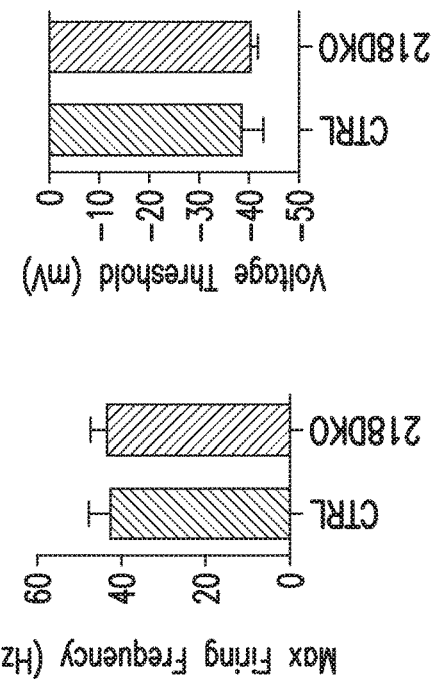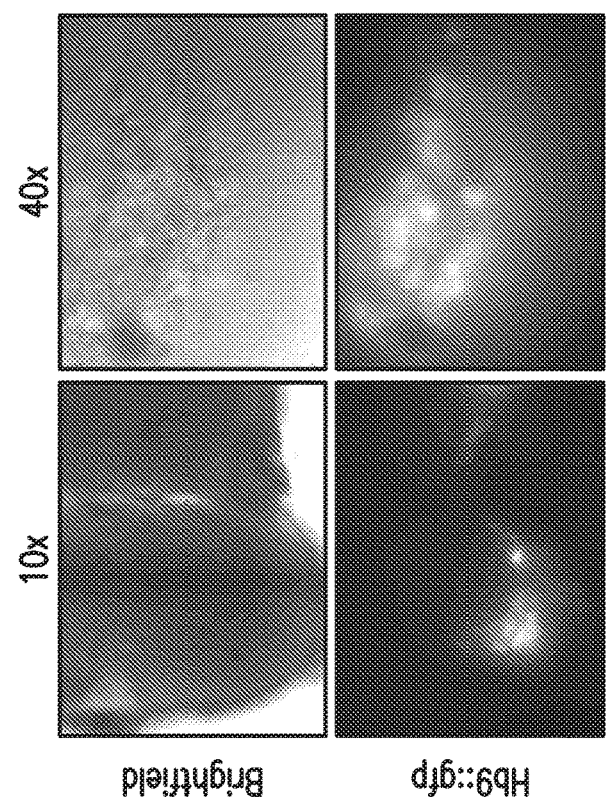

○ miR-218 context+ score <-0.15 and p<0.05
● All other genes (with minimum NRPK>10)

miR-218: 5' UUGUGCUUGAUCUAACCAUGU (G) 3'
miR-218: 3' (G) UGUACCAAUCUAGUUCGUGUU 5'
                              ||||||||
3' UTR:                       ||||||||
8mer      match:         AAGCACAA
7mer      match:         AAGCACA
7mer-1A   match:          AGCACAA
6mer      match:          AGCACA
6mer-1A   match:           GCACAA
6mer-6A   match:         AAGCAC Enriched gene ontology terms in target$^{218}$ genes

| Description | P-value | Enrichment | # of genes |
|---|---|---|---|
| regulation of cellular process | 1.1E-04 | 1.22 | 187 |
| regulation of biological process | 1.8E-04 | 1.2 | 193 |
| negative regulation of synaptic transmission | 1.9E-04 | 5.76 | 7 |
| biological regulation | 2.1E-04 | 1.19 | 199 |
| regulation of primary metabolic process | 2.9E-04 | 1.32 | 119 |
| regulation of cellular metabolic process | 3.3E-04 | 1.3 | 122 |
| neurotransmitter transport | 5.7E-04 | 4.24 | 8 |
| regulation of macromolecule metabolic process | 6.0E-04 | 1.3 | 118 |
| regulation of signaling | 6.2E-04 | 1.48 | 66 |
| Kit signaling pathway | 6.7E-04 | 38.69 | 2 |

FIG. 38F

| negative regulation of synaptic transmission | |
|---|---|
| Shank2 | sh3/ankyrin domain gene 2 |
| Grik2 | glutamate receptor, ionotropic, kainate 2 (beta 2) |
| Gnai2 | guanine nucleotide binding protein (g protein), alpha inhibiting 2 |
| Stxbp1 | syntaxin binding protein 1 |
| Park2 | parkinson disease (autosomal recessive, juvenile) 2; parkin |
| Slc6a1 | solute carrier family 6 (neurotransmitter transporter, gaba), member 1 |
| Celf4 | cugbp, elav like family member 4 |
| neurotransmitter transport | |
| Syt13 | synaptotagmin xiii |
| Stx3 | syntaxin 3 |
| Stxbp1 | syntaxin binding protein 1 |
| Park2 | parkinson disease (autosomal recessive, juvenile) 2, parkin |
| Slc6a1 | solute carrier family 6 (neurotransmitter transporter, gaba), member 1 |
| Sv2a | synaptic vesicle glycoprotein 2 a |
| Nrxn3 | neurexin iii |
| Slc6a17 | solute carrier family 6 (neurotransmitter transporter), member 17 |

FIG. 38G

| Neuronal population | Genetic reporter mouse line |
|---|---|
| Motor neurons | Hb9:gfp |
| V1 interneurons | En1:Cre, LSL:tdtomato |
| V2a inerneurons | Chx10:Cre; LSL:tdtomato |
| V3 interneurons | Sim1:Cre; LSL:tdtomato |
| Progenitors | Genetic reporter embryonic stem cell line |
|---|---|
| NP | (unsorted) neurospheres on d4 of differentiation |
| pMN | Olig2:Cre x LSL:tdtomato sorted on d4 of differentiation |
FIG. 39A
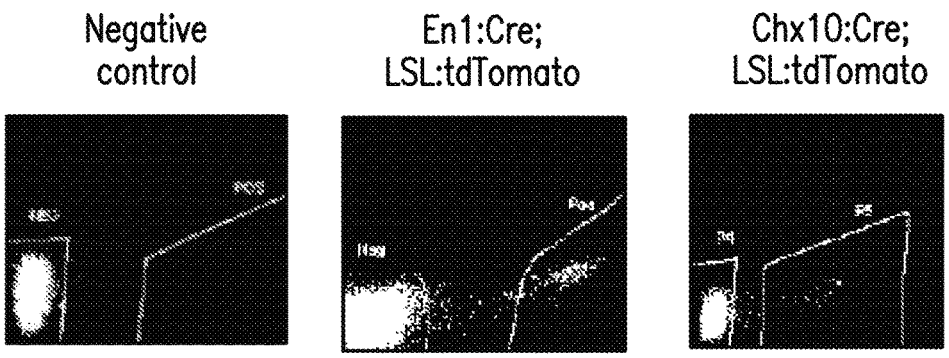
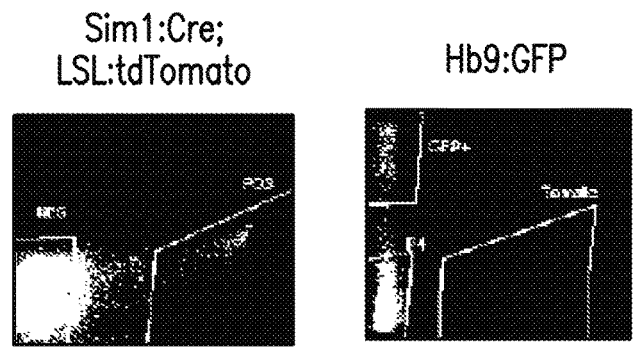
FIG. 39B

| TARGET218 gene list Gene Symbol | Context+ score | NRPK WT MNs | NRPK 218DKO MNs | Fold increase |
|---|---|---|---|---|
| Slc1a2 | -0.43 | 136.2 | 499.0 | 266% |
| Slc6a1 | -0.35 | 161.0 | 585.2 | 264% |
| Itm2c | -0.23 | 198.8 | 634.9 | 219% |
| 2510009E07Rik | -0.75 | 102.3 | 318.9 | 212% |
| Kif21b | -0.28 | 661.8 | 2004.6 | 203% |
| Syt13 | -0.42 | 69.9 | 207.3 | 197% |
| Chl1 | -0.22 | 266.4 | 751.0 | 182% |
| Cetn2 | -0.15 | 140.9 | 394.0 | 180% |
| Plgrkt | -0.37 | 144.0 | 397.0 | 176% |
| Mdfic | -0.28 | 3.9 | 10.8 | 174% |
| Yeats4 | -0.31 | 509.8 | 1357.5 | 166% |
| Scrt1 | -0.39 | 326.0 | 849.1 | 160% |
| Slc6a17 | -0.15 | 95.2 | 247.7 | 160% |
| 6330403A02Rik | -0.16 | 18.5 | 47.5 | 157% |
| Lrrc39 | -0.22 | 18.1 | 44.6 | 146% |
| Rassf2 | -0.40 | 86.5 | 212.5 | 146% |
| 2010107G23Rik | -0.29 | 100.4 | 242.0 | 141% |
| Sertad4 | -0.23 | 40.7 | 97.9 | 141% |
| Psap | -0.15 | 1840.8 | 4279.0 | 132% |
| Prrg3 | -0.15 | 94.1 | 217.5 | 131% |
| Prkx | -0.21 | 142.1 | 325.3 | 129% |
| Zmat4 | -0.16 | 71.7 | 162.4 | 127% |
| Necab1 | -0.18 | 9.1 | 20.6 | 126% |
| Syne1 | -0.16 | 6.9 | 15.5 | 125% |
| Gpr153 | -0.29 | 117.6 | 259.2 | 120% |
| Cdkn2aip | -0.35 | 140.2 | 307.2 | 119% |
| Snx4 | -0.55 | 301.8 | 660.2 | 119% |
| Pex2 | -0.30 | 102.4 | 223.0 | 118% |
| Scai | -0.20 | 106.2 | 230.8 | 117% |
| AU041133 | -0.41 | 37.6 | 81.7 | 117% |
| Slit2 | -0.18 | 1800.9 | 3911.8 | 117% |
| Mcf2 | -0.21 | 15.8 | 34.1 | 116% |
| Ankrd44 | -0.16 | 61.7 | 132.5 | 115% |
| Vav3 | -0.17 | 81.9 | 175.4 | 114% |
| Tub | -0.23 | 332.9 | 710.5 | 113% |
| Sec61a1 | -0.23 | 441.0 | 931.6 | 111% |
| Pold3 | -0.37 | 81.9 | 171.8 | 110% |
| Serinc5 | -0.22 | 111.4 | 233.4 | 110% |
| Lmo3 | -0.34 | 225.1 | 467.3 | 108% |
| Zbtb11 | -0.30 | 93.2 | 193.3 | 107% |
| Bmi1 | -0.31 | 283.3 | 586.0 | 107% |
| N28178 | -0.32 | 204.8 | 423.2 | 107% |
| Fam65b | -0.30 | 30.6 | 62.4 | 104% |
| Lypd6b | -0.35 | 59.8 | 121.2 | 102% |
| Fam63b | -0.29 | 82.8 | 166.6 | 101% |
| Epha7 | -0.41 | 164.8 | 331.3 | 101% |
| Sh3rf1 | -0.32 | 210.8 | 423.4 | 101% |

FIG. 40

| | | | | |
|---|---|---|---|---|
| Gucy1a2 | -0.29 | 60.1 | 119.9 | 100% |
| Tmem25 | -0.33 | 67.6 | 134.7 | 99% |
| Paip2b | -0.19 | 365.0 | 719.1 | 97% |
| Clcc1 | -0.25 | 56.8 | 111.3 | 96% |
| Brdt | -0.22 | 27.5 | 53.6 | 95% |
| Lin28b | -0.32 | 47.8 | 92.8 | 94% |
| Pik3c2a | -0.25 | 61.9 | 119.8 | 94% |
| Snapc2 | -0.32 | 171.7 | 329.4 | 92% |
| Nav3 | -0.32 | 105.1 | 201.4 | 92% |
| Insig1 | -0.17 | 655.4 | 1254.0 | 91% |
| Plxnc1 | -0.32 | 116.5 | 222.8 | 91% |
| Ptprk | -0.38 | 66.5 | 126.8 | 91% |
| Herpud1 | -0.32 | 313.1 | 596.2 | 90% |
| Reln | -0.36 | 279.6 | 531.0 | 90% |
| Cacnb4 | -0.27 | 77.2 | 146.2 | 89% |
| Fam118a | -0.45 | 108.8 | 203.5 | 87% |
| Clec2g | -0.39 | 5.9 | 10.9 | 86% |
| Park2 | -0.31 | 17.9 | 33.3 | 86% |
| Dach2 | -0.20 | 40.4 | 75.0 | 85% |
| Pclo | -0.17 | 150.7 | 278.9 | 85% |
| B3gat1 | -0.28 | 817.5 | 1512.7 | 85% |
| Fcho2 | -0.29 | 98.6 | 182.2 | 85% |
| Rabgap1l | -0.74 | 250.5 | 460.9 | 84% |
| Rabep1 | -0.25 | 427.9 | 786.4 | 84% |
| Jmy | -0.32 | 80.3 | 147.6 | 84% |
| Kit | -0.19 | 49.0 | 89.9 | 84% |
| Stx3 | -0.15 | 55.9 | 102.5 | 83% |
| Them6 | -0.47 | 34.5 | 62.7 | 82% |
| Pdzd4 | -0.24 | 591.9 | 1070.8 | 81% |
| Zcchc9 | -0.18 | 97.9 | 177.1 | 81% |
| Prune2 | -0.17 | 24.9 | 44.8 | 80% |
| Gng3 | -0.28 | 1660.8 | 2984.2 | 80% |
| Rnf165 | -0.22 | 388.0 | 696.7 | 80% |
| Arhgef12 | -0.20 | 364.0 | 653.4 | 79% |
| Samd8 | -0.23 | 140.3 | 249.8 | 78% |
| Adrbk2 | -0.18 | 75.7 | 134.6 | 78% |
| Phc3 | -0.21 | 87.1 | 154.4 | 77% |
| Pkd2l2 | -0.18 | 56.1 | 99.0 | 77% |
| Nox4 | -0.18 | 10.7 | 18.9 | 76% |
| Gabra5 | -0.17 | 135.7 | 236.3 | 74% |
| B630005N14Rik | -0.29 | 124.3 | 216.1 | 74% |
| G2e3 | -0.15 | 78.8 | 136.4 | 73% |
| Specc1l | -0.29 | 254.0 | 438.4 | 73% |
| Sfmbt1 | -0.29 | 53.6 | 92.4 | 72% |
| Mob1b | -0.29 | 85.9 | 147.8 | 72% |
| Gadd45a | -0.27 | 109.5 | 188.5 | 72% |
| Fam178 a | -0.15 | 208.3 | 358.2 | 72% |
| Mtmr1 | -0.30 | 109.9 | 188.8 | 72% |
| Vat1 | -0.34 | 1125.0 | 1930.9 | 72% |
| St18 | -0.20 | 145.1 | 248.8 | 71% |
| Satb2 | -0.32 | 81.1 | 138.8 | 71% |
| Sgsm1 | -0.19 | 111.0 | 190.0 | 71% |
| Dnal1 | -0.20 | 60.7 | 103.8 | 71% |

FIG. 40 Continued

| | | | | |
|---|---|---|---|---|
| Glce | -0.51 | 82.4 | 140.5 | 71% |
| Sv2a | -0.20 | 959.5 | 1632.9 | 70% |
| Rnf103 | -0.43 | 155.9 | 265.1 | 70% |
| Kirrel3 | -0.36 | 95.9 | 162.7 | 70% |
| Csmd3 | -0.20 | 64.3 | 109.0 | 69% |
| Serpini1 | -0.22 | 835.7 | 1413.6 | 69% |
| Mxd1 | -0.16 | 154.6 | 259.4 | 68% |
| Adarb1 | -0.22 | 65.5 | 109.8 | 68% |
| Celf4 | -0.26 | 924.5 | 1544.5 | 67% |
| Irak1bp1 | -0.16 | 124.5 | 207.3 | 67% |
| Ugt8a | -0.15 | 25.4 | 42.2 | 66% |
| Chuk | -0.15 | 206.6 | 342.6 | 66% |
| Enoph1 | -0.15 | 156.8 | 259.0 | 65% |
| Prkar2b | -0.32 | 892.0 | 1469.2 | 65% |
| Sh3d19 | -0.19 | 43.6 | 71.5 | 64% |
| Caskin1 | -0.21 | 303.0 | 496.3 | 64% |
| Kdm5a | -0.26 | 107.9 | 176.7 | 64% |
| Lrrfip1 | -0.17 | 191.7 | 313.9 | 64% |
| Eif2ak3 | -0.40 | 137.2 | 224.6 | 64% |
| Dcbld2 | -0.25 | 271.6 | 444.0 | 64% |
| Stam2 | -0.37 | 229.2 | 373.0 | 63% |
| Ccp110 | -0.19 | 295.8 | 480.6 | 62% |
| Ankrd45 | -0.29 | 82.6 | 133.9 | 62% |
| Hectd2 | -0.42 | 47.1 | 76.3 | 62% |
| Cntnap2 | -0.22 | 270.7 | 438.3 | 62% |
| Elmo1 | -0.18 | 178.2 | 287.5 | 61% |
| Rnasel | -0.17 | 237.5 | 383.1 | 61% |
| Sh3rf3 | -0.21 | 20.4 | 32.7 | 61% |
| Myt1l | -0.27 | 647.8 | 1040.7 | 61% |
| Rcbtb1 | -0.27 | 303.3 | 487.1 | 61% |
| Prox2 | -0.28 | 8.0 | 12.9 | 60% |
| Pum2 | -0.28 | 555.1 | 890.0 | 60% |
| Klhl13 | -0.17 | 524.1 | 838.1 | 60% |
| B3gat2 | -0.27 | 102.3 | 163.6 | 60% |
| Tmpo | -0.17 | 543.8 | 868.8 | 60% |
| Kctd9 | -0.68 | 56.3 | 89.9 | 60% |
| Hdac7 | -0.24 | 243.7 | 387.0 | 59% |
| Mpv17 | -0.21 | 181.1 | 286.7 | 58% |
| Rmdn2 | -0.19 | 26.3 | 41.5 | 58% |
| Mdga2 | -0.32 | 86.3 | 135.5 | 57% |
| Eogt | -0.15 | 38.2 | 59.9 | 57% |
| Rab43 | -0.21 | 62.5 | 98.0 | 57% |
| Tspan5 | -0.23 | 587.1 | 920.5 | 57% |
| Trhde | -0.24 | 49.3 | 77.3 | 57% |
| L3hypdh | -0.24 | 39.2 | 61.3 | 56% |
| Kcnh1 | -0.41 | 15.8 | 24.5 | 56% |
| Ipp | -0.34 | 48.2 | 75.0 | 56% |
| Slc24a3 | -0.16 | 301.3 | 466.5 | 55% |
| Nrxn3 | -0.16 | 199.5 | 308.7 | 55% |
| Skil | -0.17 | 232.6 | 359.7 | 55% |
| Ptp4a1 | -0.27 | 371.1 | 573.5 | 55% |
| 1600012H06Rik | -0.42 | 87.3 | 134.5 | 54% |
| Asxl2 | -0.16 | 57.8 | 89.0 | 54% |

FIG. 40 Continued

| | | | | |
|---|---|---|---|---|
| Zeb2 | -0.37 | 164.6 | 253.5 | 54% |
| Synm | -0.18 | 83.0 | 127.7 | 54% |
| Sde2 | -0.17 | 194.6 | 299.2 | 54% |
| Snai2 | -0.19 | 10.6 | 16.2 | 54% |
| Robo2 | -0.31 | 700.5 | 1074.9 | 53% |
| Edem1 | -0.34 | 51.5 | 78.9 | 53% |
| Zfp810 | -0.26 | 146.2 | 223.8 | 53% |
| Rock1 | -0.19 | 181.3 | 277.2 | 53% |
| Ap4e1 | -0.15 | 105.4 | 161.0 | 53% |
| Onecut2 | -0.79 | 129.7 | 196.5 | 52% |
| Golt1b | -0.17 | 234.2 | 354.9 | 52% |
| Tmem132b | -0.17 | 97.8 | 148.2 | 51% |
| Snx13 | -0.17 | 95.4 | 144.6 | 51% |
| Zmiz2 | -0.24 | 906.9 | 1372.9 | 51% |
| Snx8 | -0.17 | 184.7 | 279.0 | 51% |
| Adipor2 | -0.26 | 277.3 | 418.5 | 51% |
| Galnt13 | -0.28 | 59.8 | 90.3 | 51% |
| Camkk2 | -0.28 | 295.9 | 445.3 | 50% |
| Abca3 | -0.18 | 447.5 | 672.5 | 50% |
| Aacs | -0.18 | 314.6 | 471.6 | 50% |
| Jtb | -0.18 | 205.9 | 307.3 | 49% |
| Tenm3 | -0.29 | 212.2 | 316.4 | 49% |
| Sash1 | -0.19 | 74.1 | 110.3 | 49% |
| Tspan3 | -0.15 | 1659.4 | 2467.3 | 49% |
| Rhobtb1 | -0.30 | 51.0 | 75.8 | 49% |
| Clk3 | -0.15 | 391.1 | 580.2 | 48% |
| Lmnb1 | -0.17 | 790.3 | 1170.7 | 48% |
| Ing3 | -0.18 | 64.7 | 95.8 | 48% |
| Sdccag3 | -0.15 | 546.3 | 803.8 | 47% |
| Ppp2r5a | -0.21 | 28.4 | 41.8 | 47% |
| Fam161b | -0.18 | 107.7 | 158.3 | 47% |
| Actn1 | -0.27 | 54.9 | 80.7 | 47% |
| Piezo2 | -0.70 | 11.0 | 16.2 | 47% |
| Heca | -0.28 | 151.1 | 220.6 | 46% |
| Ubr3 | -0.34 | 364.3 | 530.9 | 46% |
| Fam196a | -0.26 | 63.9 | 93.1 | 46% |
| Crtc3 | -0.23 | 51.3 | 74.7 | 46% |
| Ick | -0.16 | 327.0 | 475.9 | 46% |
| Itga9 | -0.15 | 65.4 | 95.1 | 45% |
| Ranbp10 | -0.23 | 176.7 | 256.8 | 45% |
| Rpl7l1 | -0.21 | 226.8 | 329.3 | 45% |
| Ubqln2 | -0.25 | 1313.9 | 1905.2 | 45% |
| Rnf114 | -0.20 | 518.1 | 751.0 | 45% |
| Gemin6 | -0.15 | 47.0 | 68.1 | 45% |
| Shisa6 | -0.37 | 50.2 | 72.5 | 45% |
| Nmral1 | -0.31 | 209.3 | 302.1 | 44% |
| Med4 | -0.17 | 267.6 | 385.9 | 44% |
| Ermp1 | -0.47 | 89.2 | 128.6 | 44% |
| Socs6 | -0.23 | 140.8 | 202.6 | 44% |
| Zbtb10 | -0.27 | 136.7 | 196.2 | 44% |
| Pbx2 | -0.25 | 435.4 | 622.4 | 43% |
| Hoxd10 | -0.25 | 785.2 | 1121.7 | 43% |
| Morc4 | -0.16 | 23.4 | 33.5 | 43% |

FIG. 40 Continued

| | | | | |
|---|---|---|---|---|
| Dph6 | -0.17 | 61.6 | 87.6 | 42% |
| Slc36a4 | -0.20 | 229.7 | 325.8 | 42% |
| Camkmt | -0.37 | 67.9 | 96.0 | 41% |
| Vamp7 | -0.24 | 171.8 | 242.1 | 41% |
| Tyw3 | -0.23 | 28.1 | 39.6 | 41% |
| 2010315B03Rik | -0.29 | 57.0 | 79.9 | 40% |
| Aff4 | -0.25 | 415.1 | 581.6 | 40% |
| Necap2 | -0.21 | 123.4 | 172.5 | 40% |
| Uhrf1bp1l | -0.22 | 145.4 | 202.9 | 40% |
| Pkn2 | -0.25 | 86.8 | 121.0 | 39% |
| Agpat3 | -0.15 | 234.6 | 325.7 | 39% |
| Prosc | -0.21 | 231.4 | 320.2 | 38% |
| Net1 | -0.30 | 33.3 | 46.0 | 38% |
| Sema6b | -0.16 | 205.9 | 284.0 | 38% |
| D17H6S53E | -0.16 | 44.3 | 60.9 | 38% |
| Gabpa | -0.16 | 96.7 | 132.6 | 37% |
| Sh3gl1 | -0.20 | 320.7 | 440.0 | 37% |
| Cstf2t | -0.22 | 339.3 | 463.9 | 37% |
| Epha5 | -0.20 | 234.7 | 320.0 | 36% |
| Fam86 | -0.24 | 21.5 | 29.3 | 36% |
| Pou3f3 | -0.15 | 332.0 | 452.6 | 36% |
| Pcgf2 | -0.30 | 502.4 | 684.1 | 36% |
| Nufip2 | -0.19 | 101.5 | 138.2 | 36% |
| Gnai2 | -0.20 | 932.1 | 1267.9 | 36% |
| Lgr4 | -0.55 | 68.5 | 92.6 | 35% |
| Mast4 | -0.18 | 240.1 | 324.0 | 35% |
| Srxn1 | -0.24 | 82.3 | 110.9 | 35% |
| Zfp521 | -0.19 | 293.1 | 395.0 | 35% |
| Wnt2b | -0.29 | 9.6 | 12.9 | 35% |
| Ebf3 | -0.17 | 369.4 | 497.4 | 35% |
| Cab39l | -0.25 | 57.8 | 77.7 | 35% |
| Rap1gap | -0.23 | 371.3 | 499.2 | 34% |
| Tmem206 | -0.28 | 106.2 | 142.4 | 34% |
| Fam45a | -0.39 | 144.7 | 194.1 | 34% |
| 9830147E19Rik | -0.31 | 43.2 | 57.9 | 34% |
| Mier3 | -0.44 | 98.7 | 132.3 | 34% |
| Smchd1 | -0.24 | 163.2 | 218.5 | 34% |
| Hecw1 | -0.20 | 274.2 | 366.2 | 34% |
| Gca | -0.24 | 12.1 | 16.1 | 33% |
| Jrkl | -0.35 | 62.3 | 82.6 | 33% |
| Kdm1b | -0.18 | 173.9 | 230.1 | 32% |
| Rrp1b | -0.25 | 97.3 | 128.6 | 32% |
| Col4a3bp | -0.29 | 192.2 | 253.8 | 32% |
| Rab36 | -0.17 | 64.0 | 84.4 | 32% |
| Mtx3 | -0.15 | 138.8 | 183.1 | 32% |
| Emc4 | -0.15 | 663.5 | 874.5 | 32% |
| Pcnp | -0.19 | 993.7 | 1309.1 | 32% |
| Epc1 | -0.16 | 605.2 | 795.3 | 31% |
| Ahctf1 | -0.18 | 180.1 | 236.5 | 31% |
| Gpr155 | -0.24 | 89.8 | 117.8 | 31% |
| Grik2 | -0.26 | 112.3 | 147.2 | 31% |
| Zbtb26 | -0.17 | 64.3 | 84.0 | 31% |

FIG. 40 Continued

| | | | | |
|---|---|---|---|---|
| Pld5 | -0.27 | 105.0 | 137.0 | 30% |
| Mtmr12 | -0.39 | 54.0 | 70.4 | 30% |
| Uvssa | -0.26 | 44.9 | 58.5 | 30% |
| Kalrn | -0.27 | 300.4 | 390.2 | 30% |
| Nol7 | -0.25 | 330.7 | 427.8 | 29% |
| Pde7a | -0.24 | 290.8 | 375.6 | 29% |
| Arf6 | -0.24 | 235.3 | 303.8 | 29% |
| Mmp24 | -0.16 | 560.4 | 723.5 | 29% |
| Dnajc1 | -0.25 | 58.1 | 74.8 | 29% |
| Tgfbrap1 | -0.30 | 140.5 | 180.9 | 29% |
| Iba57 | -0.20 | 52.8 | 67.9 | 29% |
| Creb1 | -0.18 | 217.9 | 280.2 | 29% |
| Wipi2 | -0.18 | 273.9 | 352.0 | 28% |
| Zfp719 | -0.23 | 47.8 | 61.4 | 28% |
| Tmem150c | -0.25 | 178.7 | 229.0 | 28% |
| Srsf6 | -0.30 | 1194.9 | 1531.3 | 28% |
| Rcc1 | -0.21 | 133.7 | 171.0 | 28% |
| Cacna1g | -0.24 | 440.9 | 563.6 | 28% |
| Uck1 | -0.15 | 310.6 | 396.8 | 28% |
| Onecut3 | -0.30 | 79.7 | 101.4 | 27% |
| Zfp445 | -0.23 | 836.0 | 1062.0 | 27% |
| Opn3 | -0.23 | 40.4 | 51.3 | 27% |
| Zfp202 | -0.28 | 72.2 | 91.4 | 27% |
| Insr | -0.25 | 288.6 | 365.4 | 27% |
| Sqstm1 | -0.20 | 1748.2 | 2212.5 | 27% |
| Pex5l | -0.28 | 98.4 | 124.4 | 26% |
| Lasp1 | -0.16 | 954.5 | 1204.0 | 26% |
| Smim19 | -0.15 | 165.4 | 208.1 | 26% |
| Shprh | -0.23 | 173.2 | 216.4 | 25% |
| Efcab2 | -0.29 | 38.4 | 47.8 | 24% |
| Agap1 | -0.20 | 418.1 | 518.5 | 24% |
| Rint1 | -0.36 | 114.1 | 141.5 | 24% |
| Lmo7 | -0.31 | 12.7 | 15.8 | 24% |
| Twsg1 | -0.17 | 211.0 | 261.4 | 24% |
| Gpr45 | -0.31 | 51.5 | 63.7 | 24% |
| Prr14l | -0.18 | 85.5 | 105.5 | 23% |
| Rassf5 | -0.23 | 30.3 | 37.3 | 23% |
| Zscan29 | -0.19 | 54.1 | 66.7 | 23% |
| Shank2 | -0.22 | 205.1 | 252.7 | 23% |
| Rnf24 | -0.17 | 283.8 | 348.8 | 23% |
| Birc6 | -0.27 | 236.4 | 289.7 | 23% |
| Gfpt1 | -0.26 | 370.7 | 453.1 | 22% |
| Golga7 | -0.19 | 1070.3 | 1306.1 | 22% |
| Prmt6 | -0.16 | 202.1 | 246.6 | 22% |
| Hars2 | -0.23 | 170.8 | 208.0 | 22% |
| Tomm5 | -0.23 | 395.8 | 480.3 | 21% |
| Gnb1 | -0.18 | 5447.6 | 6607.9 | 21% |
| Araf | -0.17 | 1419.0 | 1718.2 | 21% |
| Stxbp1 | -0.17 | 2311.1 | 2795.0 | 21% |
| Cbx5 | -0.21 | 835.5 | 1010.3 | 21% |
| Sertad2 | -0.28 | 110.8 | 133.4 | 20% |
| Ctnnd2 | -0.28 | 403.7 | 484.4 | 20% |
| Rnf219 | -0.22 | 165.5 | 198.4 | 20% |

FIG. 40 Continued

| | | | | |
|---|---|---|---|---|
| Psmd14 | -0.18 | 778.4 | 933.0 | 20% |
| 4930402H24Rik | -0.18 | 946.3 | 1129.1 | 19% |
| Rnf19b | -0.17 | 596.7 | 711.0 | 19% |
| Ncan | -0.30 | 692.4 | 823.6 | 19% |
| D230025D16Rik | -0.28 | 148.3 | 175.8 | 19% |
| Sec62 | -0.27 | 563.8 | 666.2 | 18% |
| Rnf41 | -0.32 | 299.7 | 352.9 | 18% |
| C77080 | -0.17 | 99.4 | 116.4 | 17% |
| Acox1 | -0.21 | 534.8 | 626.1 | 17% |
| Pum1 | -0.16 | 552.1 | 644.2 | 17% |
| Micall1 | -0.22 | 376.8 | 438.6 | 16% |
| Tmem129 | -0.24 | 78.6 | 90.7 | 15% |
| Tmem110 | -0.17 | 89.2 | 101.8 | 14% |
| Fert2 | -0.15 | 193.2 | 218.8 | 13% |
| Acsl1 | -0.30 | 126.9 | 143.4 | 13% |
| Ppp2r4 | -0.21 | 783.8 | 884.2 | 13% |
| Papola | -0.21 | 596.0 | 669.2 | 12% |
| L3mbtl3 | -0.34 | 172.1 | 193.2 | 12% |
| Tmub2 | -0.23 | 453.7 | 502.1 | 11% |
| Gmeb1 | -0.40 | 141.6 | 154.9 | 9% |
| Cdc42se2 | -0.20 | 575.6 | 626.2 | 9% |
| Gpatch2l | -0.27 | 206.2 | 222.9 | 8% |

FIG. 40 Continued

Primer and sequence information.

| Promoter Cloning | Forward primer | Reverse primer | Promoter size |
|---|---|---|---|
| pri-mir218-2 7.4kb promoter | agatcggtaccgagaaatacctccgctctg | agatcgaccggtgaaggctccatcttcaatgc | 7442bp |

CRISPR gRNA sequences

| | | gRNA target sequence | PAM |
|---|---|---|---|
| mir-218-1 | Left guide (5') | tatgatcatacacaatctgc | ggg |
| mir-218-1 | Right guide (3') | ggagaataacaaatgtccgt | agg |
| mir-218-2 | Left guide (5') | gactctgaccagttgccgcg | ggg |
| mir-218-2 | Right guide (3') | taatgtggatactcgaagca | cgg |
| pri-miR-218-2 promoter | Left guide (5') | tgtctccatgcattgttacg | tgg |
| pri-miR-218-2 promoter | Right guide (3') | caggcgagcgagcgaccaa | agg | oligos for px330 vector

| Forward | Reverse |
|---|---|
| cacc g tatgatcatacacaatctgc | aaac gcagattgtgtatgatcata c |
| cacc g ggagaataacaaatgtccgt | aaac acggacatttgttattctcc |
| cacc g gactctgaccagttgccgcg | aaac cgcggcaactggtcagagtc |
| cacc g taatgtggatactcgaagca | aaac tgcttcgagtatccacatta c |
| cacc g tgtctccatgcattgttacg | aaac cgtaacaatgcatggagaca |
| cacc g caggcgagcgagcgcaccaa | aaac ttggtgcgctcgctcgcctg |

T7-sgRNA PCR

| T7 Primer | Reverse T7 Primer |
|---|---|
| taatacgactcactatagg | aaaagcaccgactcggtgcc |
| tatgatcatacacaatctgc | |
| taatacgactcactata | |
| ggagaataacaaatgtccgt | aaaagcaccgactcggtgcc |
| taatacgactcactatag | |
| gactctgaccagttgccgcg | aaaagcaccgactcggtgcc |
| taatacgactcactatagg | |
| taatgtggatactcgaagca | aaaagcaccgactcggtgcc |
| taatacgactcactatagg | |
| tgtctccatgcattgttacg | aaaagcaccgactcggtgcc |
| taatacgactcactatagg | |
| caggcgagcgagcgcaccaa | aaaagcaccgactcggtgcc |

| Genotyping | Forward primer | Reverse primer | Band Sizes | Deletion size |
|---|---|---|---|---|
| miR-218-2 genotyping | ggcagtcctgtgtcacaaag | tggatatcggggttcatcgg | WT: 998bp/KO: 712bp | 286bp deletion |
| miR-218-1 genotyping | accctcttttcaatccctga | ctttctgctgatccgatttctg | WT: 841bp/KO: 482bp | 359bp deletion |

FIG. 41

MOTOR NEURON-SPECIFIC EXPRESSION VECTORS

CROSS REFERENCE TO RELATED APPLICATIONS

The present application is a National Stage Entry of PCT/US2016/033914, filed May 24, 2016, which claims priority to U.S. Provisional Application No. 62/166,677 filed May 26, 2015, U.S. Provisional Application No. 62/168,755 filed May 30, 2015, and U.S. Provisional Application No. 62/268,357 filed Dec. 16, 2015, priority to each of which is claimed, and the contents of each of which are incorporated by reference in their entireties herein.

GRANT INFORMATION

This invention was made with government support under grant R37 NS037116 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 10, 2020, is named 49550-708 831 SL.txt and is 22,675 bytes in size.

1. INTRODUCTION

The present invention relates to motor neuron-specific expression vectors and their use in expressing genes specifically in motor neuron cells.

2. BACKGROUND OF THE INVENTION

2.1 Motor Neuron Disease

Motor neuron diseases are diseases which lead to impairment of motor nerve functions due to the loss of motor neuron cells, or reduction of motor neuron cell function, and degenerative changes in the motor pathways of the central nervous system. Such diseases are different from other neurodegenerative diseases such as Alzheimer's disease, which are caused by the destruction of neurons other than motor neurons. Typically, motor neuron diseases are developmental or progressive, degenerative disorders that affect nerves in the upper or lower parts of the body. Motor neuron diseases include, in addition to amyotrophic lateral sclerosis (also known as Lou Gehrig's disease), diseases which are classified into primary lateral sclerosis (PLS) affecting only motor neurons located in the cortex such as pyramidal neurons (i.e., upper motor neurons), progressive muscular atrophy (PMA) affecting only lower motor neurons (e.g., motor neurons located in spinal cord and brainstem), progressive bulbar palsy (PBP) affecting lower motor neurons of the brainstem, spinal muscular atrophy (SMA), and the like. Symptoms may include difficulty swallowing, limb weakness, slurred speech, impaired gait, facial weakness and muscle cramps. Respiration may be affected in the later stages of these diseases, frequently resulting in death. The cause(s) of most motor neuron diseases are not known, but environmental, toxic, viral or genetic factors are all suspects.

Motor neurons regulate all muscles, stimulating them to contract. Motor neurons originating in the cerebral cortex (e.g., upper motor neurons) send fibers through the brainstem and the spinal cord, and are involved in controlling lower motor neurons. Motor neurons located in spinal cord and brainstem (e.g., lower motor neurons) send fibers out to muscles. Lower motor neuron diseases are diseases involving lower motor neuron degeneration. When a lower motor neuron degenerates, the muscle fibers it normally activates become disconnected from the neuron, and do not contract, causing muscle weakness and diminished reflexes. Loss of either type of neurons results in weakness. Muscle atrophy (wasting) and painless weakness are the clinical hallmarks of motor neuron diseases. Amyotrophic Lateral Sclerosis (ALS) is a fatal motor neuron disease characterized by a loss of pyramidal cells in the cerebral motor cortex (i.e., giant Betz cells), anterior spinal motor neurons and brainstem motor neurons. ALS shows, from a clinical aspect, both upper motor neuron and lower motor neuron signs, and shows rapid clinical deterioration after onset of the disease, thus leading to death within a few years.

A small percentage (about 10%-15%) of ALS is inherited. Genetic epidemiology of ALS has revealed at least six chromosome locations accountable for the inheritance of disease (ALS1 to ALS6). Among these, three genes have been identified. The first gene identified was the cytosolic Cu/Zn superoxide dismutase (SOD-1) gene that accounts for 20% of the autosomal dominant form of ALS (Rosen et al., 1993, Nature, 1993 Mar. 4; 362(6415):59-62). The second was named as Alsin (ALS2), a potential guanine-nucleotide exchange factor (GEF) responsible for the juvenile recessive form of ALS. The third is ALS4 that encodes for a DNA/RNA helicase domain containing protein called Senataxin, identified to be linked to the autosomal dominant form of juvenile ALS. Mutations in several other genes, including the C9orf72, TARDBP, FUS, ANG, SETX, and VAPB genes, have been associated with causing familial ALS and contributing to the development of sporadic ALS.

The only safe drug used for treating ALS is riluzole, which has an antagonistic effect against glutamate, and has been approved by the US Food and Drug Administration (FDA) for commercialization. However, this drug shows unsatisfactory efficacy, which means currently there is no definite therapy for ALS that can improve rapidly deteriorating clinical conditions. Accordingly, therapeutic agents that target motor neurons would be beneficial for treating ALS and any other motor neuron specific disease.

SMA is an inherited disorder, caused by mutations in the survival of motor neuron 1 gene, SMN1. This disease preferentially affects lower motor neurons, while sparing upper motor neurons. There are many types of SMA which range in severity and onset of symptoms, with the most severe forms affecting patients neonatally resulting in death in just a couple of years. Other less severe forms of SMA compromise motor function leaving many patients wheelchair bound.

2.2 microRNAs microRNAs are appreciated as important post-transcriptional modifiers of gene expression in a variety of mammalian biological contexts. microRNAs target the 3' UTR of mRNA transcripts via complementary binding of their 'seed sequence' in complex with Argonaute proteins, thereby inducing mRNA degradation and translational repression. Many groups have profiled microRNA expression in specific tissues, including the developing mammalian central nervous system (CNS). However, it is not well understood if specific cell types (such as developmentally defined neuronal subtypes) have unique microRNA expression patterns.

Identifying a microRNA that exhibits motor neuron cell-type specificity and contributes dramatically to motor neuron identity may provide a means to express therapeutic and diagnostic agents specifically in motor neurons.

3. SUMMARY OF THE INVENTION

The present disclosure relates to a brainstem and spinal motor neuron-specific nucleic acid promoter sequence, compositions comprising said promoter sequence, and methods of using such compositions for treating a motor neuron disease in a subject in need thereof. The motor neuron-specific nucleic acid promoter sequence is able to express genes specifically in culture and in vivo. The present disclosure is based at least in part, on the discovery that the motor neuron-specific nucleic acid promoter sequence described herein by SEQ ID NO:1 was successful in expressing genes in motor neurons in vivo.

In certain non-limiting embodiments, the present invention provides for a nucleic acid sequence of SEQ ID NO:1. In one embodiment, the nucleic acid further comprises one or more additional nucleic acids that is operably linked to the nucleic acid of SEQ ID NO:1.

In one embodiment, the one or more additional nucleic acid is selectively expressible in motor neurons.

In certain non-limiting embodiments, the present invention provides for a recombinant expression vector comprising a nucleic acid sequence of SEQ ID NO:1, wherein the vector further comprises one or more additional nucleic acids operably linked to the nucleic acid of SEQ ID NO:1, and wherein the exogenous nucleic acids are selectively expressible in a motor neuron.

In one embodiment, the nucleic acid sequence of SEQ ID NO:1 is a fragment of SEQ ID NO:1 that is sufficient to express a nucleic acid operatively linked to the fragment in a motor neuron.

In one embodiment, the nucleic acid operatively linked to the nucleic acid sequence of SEQ ID NO:1, or fragment thereof, comprises a miR-218 nucleic acid sequence, or a nucleic acid comprising a miR-218 seed sequence. In one embodiment, the nucleic acid operatively linked to the nucleic acid sequence of SEQ ID NO:1, or fragment thereof, comprises a nucleic acid encoding a transcription factor protein selected from the group consisting of Isl1, Isl2, Lhx3, Isl1-Lhx3 fusion proteins, Phox2a, and a combination thereof. In one embodiment, the nucleic acid operatively linked to the nucleic acid sequence of SEQ ID NO:1, or fragment thereof, comprises a nucleic acid encoding an RNAi molecule, shRNA molecule, antisense RNA, catalytic RNA, or catalytic DNA specific for a miR-218 target nucleic acid, for example, a nucleic acid described by FIGS. 38 and 40.

The present disclosure also provides for compositions that can increase miR-218 expression, for example, miR-218 expression in a motor neuron, and methods of using such compositions for treating a motor neuron disease in a subject in need thereof. In certain embodiments, the composition comprises a miR-218 nucleic acid, or a nucleic acid comprising a miR-218 seed sequence. In certain embodiments, the composition comprises a transcription factor protein selected from the group consisting of Isl1, Isl2, Lhx3, Isl1-Lhx3 fusion proteins, Phox2a, and a combination thereof, or one or more nucleic acid encoding said proteins.

The present disclosure also provides for compositions that can decrease expression of a miR-218 target nucleic acid, for example, a nucleic acid described by FIGS. 38 and 40. In certain embodiments, a miR-218 target nucleic acid is a nucleic acid that hybridizes to a miR-218 seed sequence. In certain embodiments, the composition comprises an RNAi molecule, shRNA molecule, antisense RNA, catalytic RNA, catalytic DNA, or antibody specific for the miR-218 target nucleic acid, or protein encoded therefrom.

In one embodiment, the motor neuron is a spinal motor neuron. In one embodiment, the motor neuron is a brainstem motor neuron.

In another embodiment, the nucleic acids and/or expression vectors comprising the nucleic acids described herein, are comprised in a viral vector, for example, an adenovirus.

In certain non-limiting embodiments, the present disclosure provides for a method of introducing a nucleic acid or composition described herein into a motor neuron cell comprising administering, to the motor neuron cell, a composition or nucleic acid described herein, for example, a nucleic acid sequence of SEQ ID NO:1, or a vector comprising said nucleic acid, wherein the nucleic acid or expression vector further comprises an expressible nucleic acid.

In certain non-limiting embodiments, the present disclosure provides for a method for treating a subject diagnosed with or at risk of having a motor neuron disease, and/or reducing the severity of a motor neuron disease, comprising administering, to a subject in need of such treatment, an effective amount of a composition or nucleic acid described herein, for example, a nucleic acid sequence of SEQ ID NO:1, or a vector comprising said nucleic acid, wherein the nucleic acid or expression vector further comprises a therapeutic nucleic acid or gene.

In certain embodiments, the present disclosure provides for a cell in vitro comprising the nucleic acid of SEQ ID NO:1. In other embodiments, the disclosure provides for a transgenic animal comprising the nucleic acid of SEQ ID NO:1 operably linked to a nucleic acid or gene, for example in a recombinant vector. In certain embodiments, the nucleic acid or gene expresses a detectable protein, such as a fluorescent protein.

The present disclosure further provides for kits comprising one or more of the compositions or nucleic acids described herein, for example, a nucleic acid of SEQ ID NO:1, and/or a recombinant vector comprising the nucleic acid of SEQ ID NO:1. In certain embodiments, the kit further comprises instructions for administering the compositions or nucleic acids described herein for treating a subject diagnosed with or at risk for having a motor neuron disease.

The foregoing has outlined rather broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

4. BRIEF DESCRIPTION OF THE FIGURES

FIG. 1 shows the nucleic acid sequence of the motor neuron-specific promoter (SEQ ID NO:1) of the present disclosure.

FIG. 2A-B shows brightfield (A) and fluorescence (B) images of an E11.5 transgenic mouse embryo expressing the 908 bp miR-218-promoter:eGFP transgene (218p:eGFP short). eGFP was expressed in both the cell bodies (arrow) and axons (bracket) of motor neurons in the spinal cord. eGFP was also expressed in brainstem motor nuclei of the embryos (arrowhead).

FIG. 3A-B shows brightfield and fluorescence images of an E12.5 transgenic mouse embryo expressing the 7.6 kb miR-218 promoter:eGFP transgene (218p:eGFP long), or a homeobox gene (Hb9) promoter:GFP transgene (Hb9:GFP). eGFP was expressed in motor neurons in the spinal cord from both transgenes (A, B). GFP expression from the 218p:eGFP long transgene was stronger than from the Hb9:GFP transgene (A).

FIG. 4A-C shows brightfield (BF) and fluorescence (GFP) images of an E18.5 transgenic mouse embryo expressing the 7.6 kb miR-218 promoter:eGFP transgene (218p:eGFP long). eGFP was expressed in the brain and spinal cord of the mouse central nervous system (A). (B) shows expression of the eGFP construct in motor neurons in the cervical, thoracic and lumbar regions of the spinal cord. (C) shows expression of the eGFP transgene in brainstem motor neurons (MNs).

Figure 7:
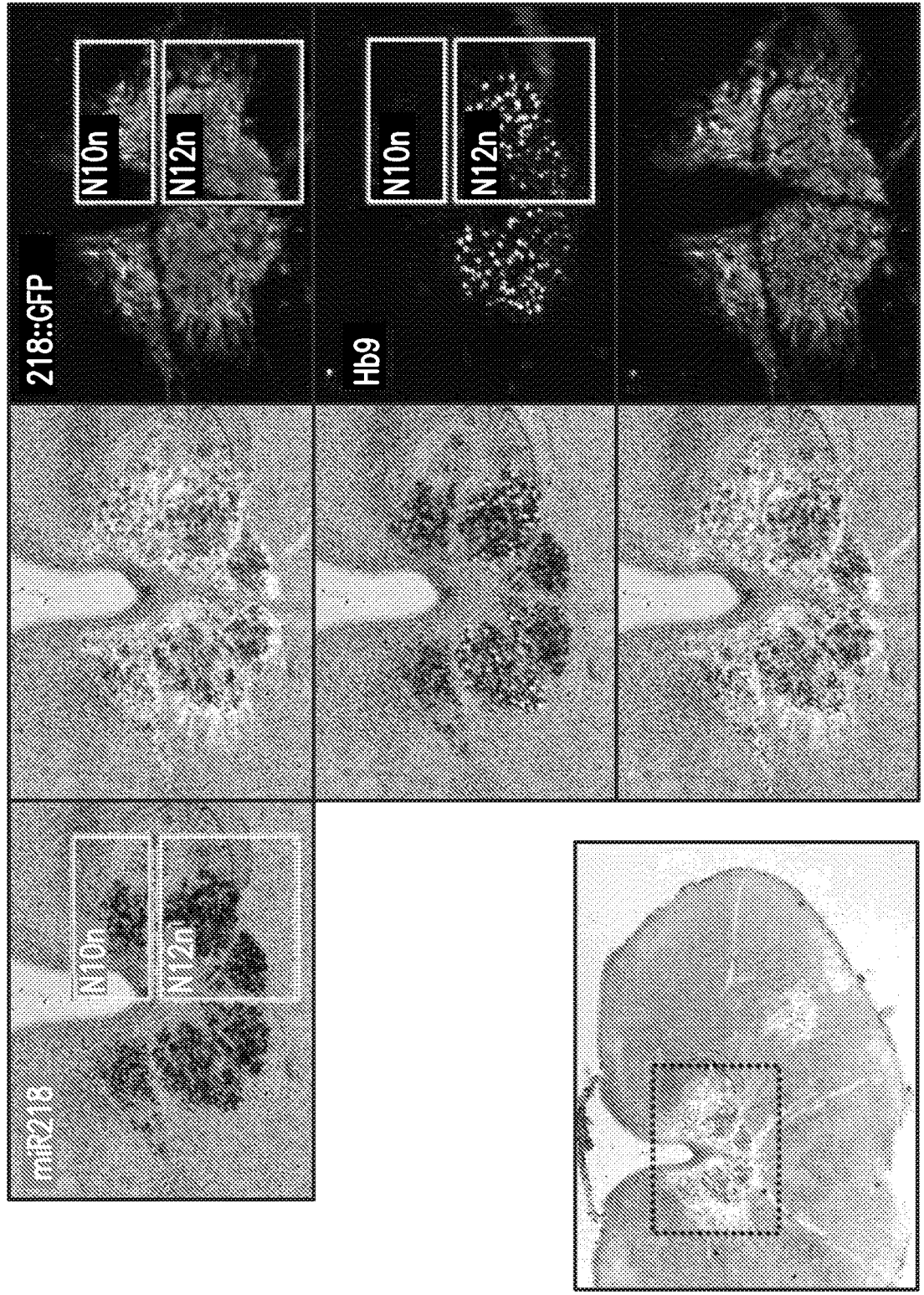

FIG. 7 shows expression of GFP in brainstem motor neuron nuclei in E18.5 transgenic mice expressing the 7.6 kb miR-218 promoter:eGFP transgene (218p::eGFP) or homeobox gene (Hb9) promoter:GFP transgene (Hb9), as compared to expression of miR-218 mRNA. miR-218 mRNA was detected by in situ hybridization. miR-218 mRNA and 218p::eGFP were expressed in N10 and N12 brainstem motor neuron nuclei, while Hb9 was expressed in N12 brainstem motor neuron nuclei.

Figure 8:
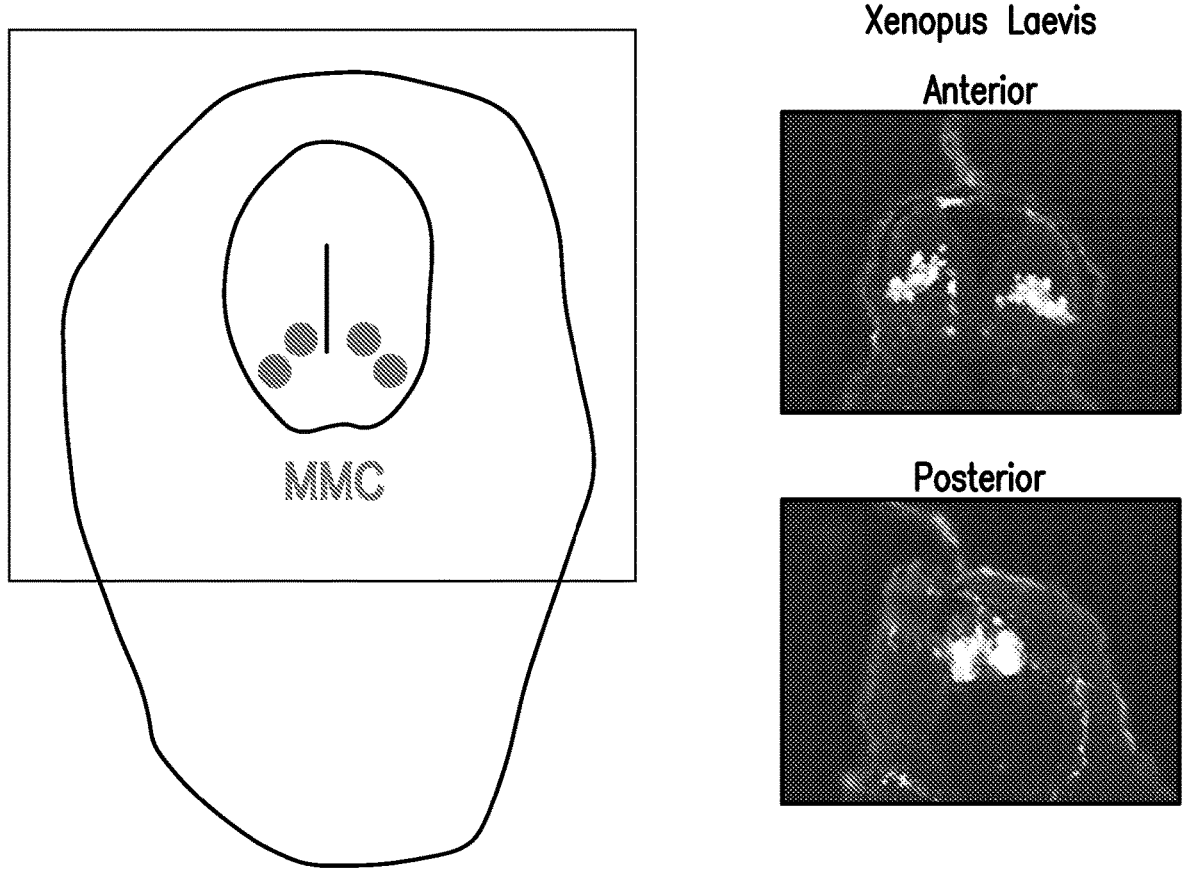

FIG. 8 shows expression of GFP in posterior motor neurons of transgenic *Xenopus laevis* swimming tadpoles. The transgenic animals expressed the *Xenopus laevis* homolog of the 7.6 kb miR-218 promoter operatively linked to GFP.

Figure 9:
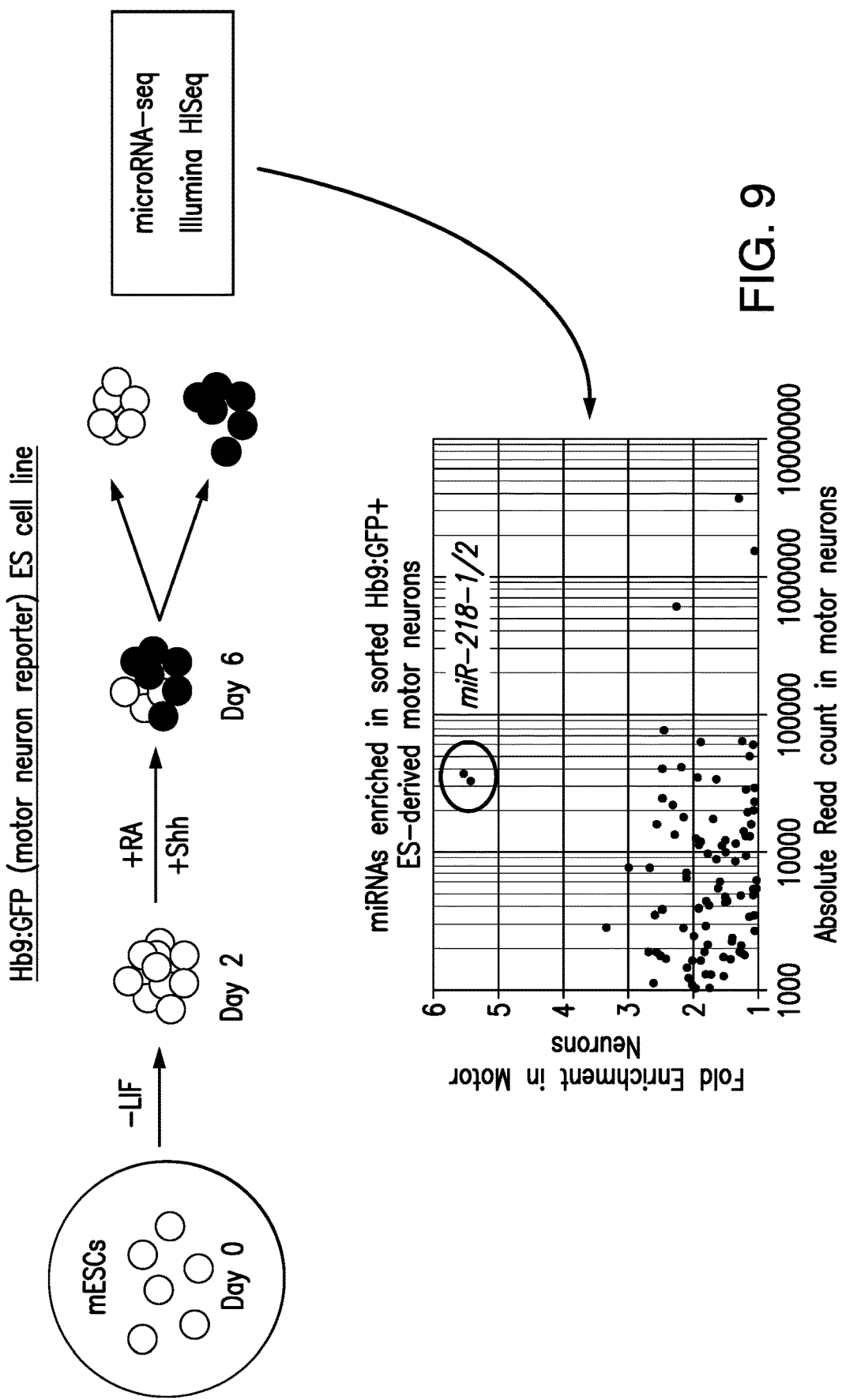

FIG. 9 shows the differentiation of mouse embryonic stem cells (mESCs) expressing a homeobox gene (Hb9) promoter:GFP transgene (Hb9:GFP) into ES-derived motor neurons, wherein miR-218 was enriched in the motor neurons expressing Hb9:GFP.

Figure 10:
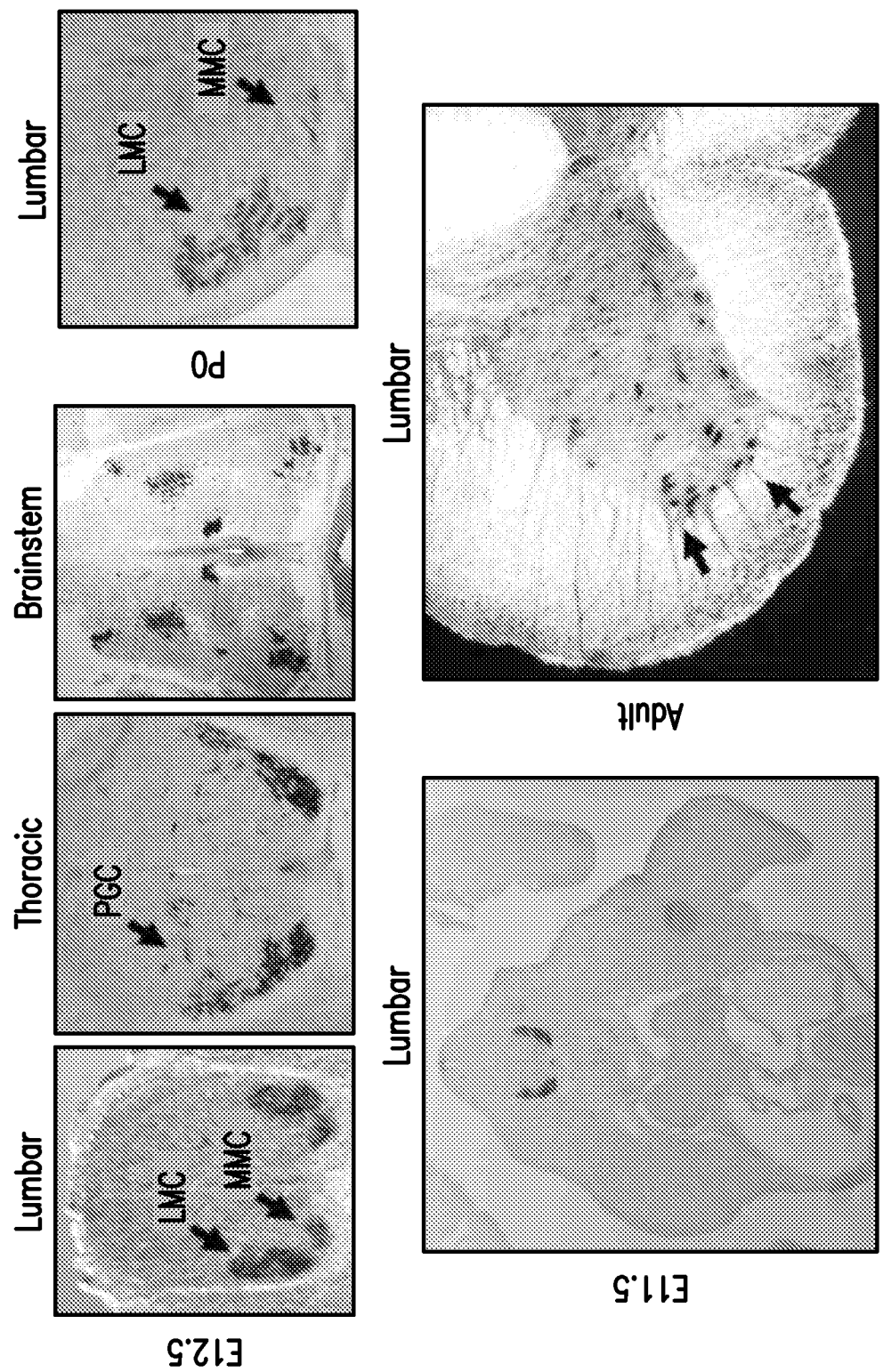
Figure 10:
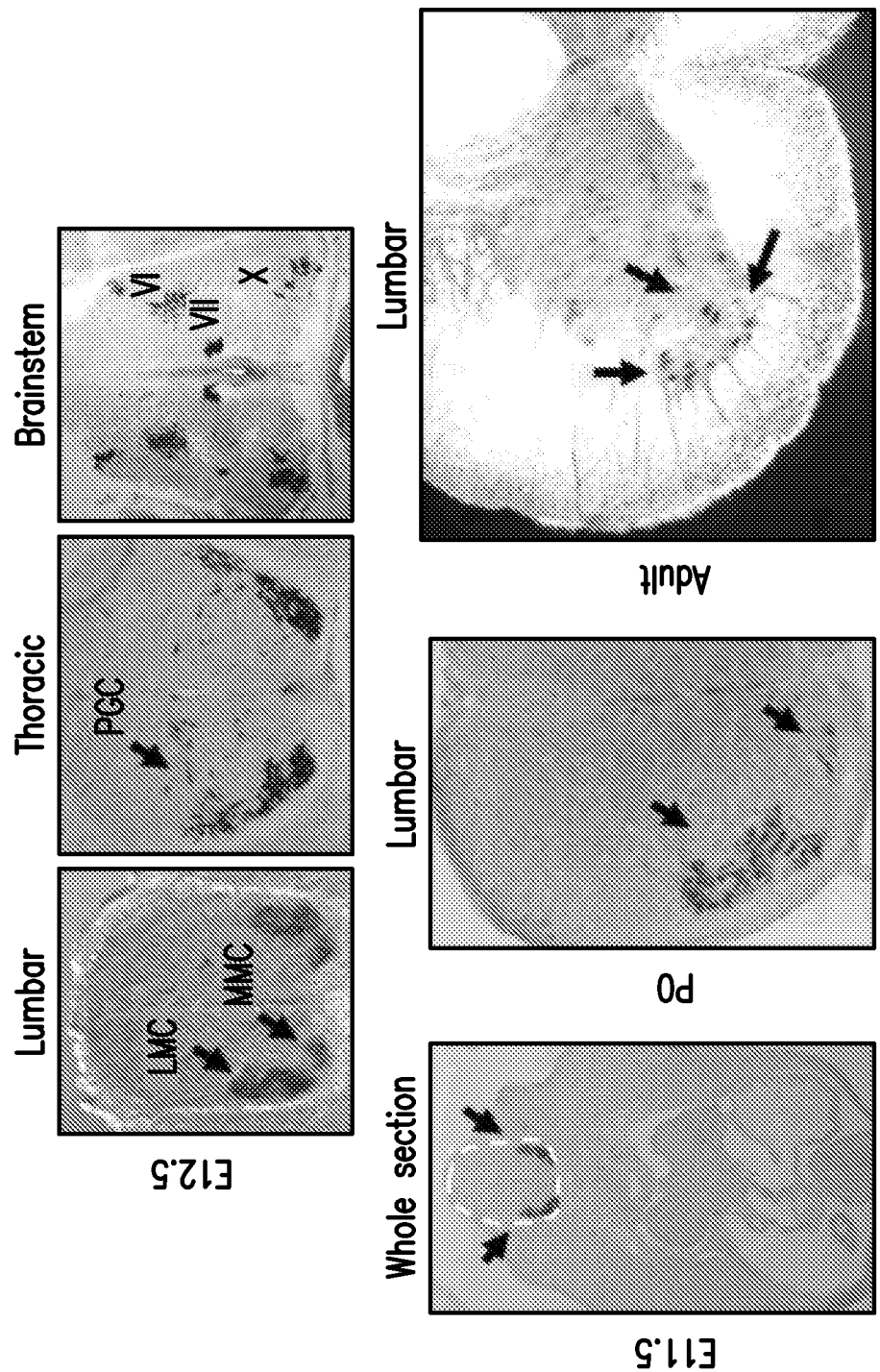

FIG. 10 shows miR-218 mRNA expression in lumbar spinal cord region of E11.5 mouse embryos; in lumbar and thoracic regions of spinal cord, as well as in brainstem, of E12.5 embryos; in lumbar spinal cord region of PO mice; and in lumbar spinal cord region of adult mice.

FIG. 11 shows miR-218 mRNA expression in motor neurons of E11.5 mice wherein the mRNA was expressed in motor neuron cells that migrated into the ventro-lateral spinal cord. Cells migrating into the ventro-lateral spinal cord were identified by expression of a homeobox gene (Hb9) promoter:GFP transgene (Hb9:GFP).

Figure 12:
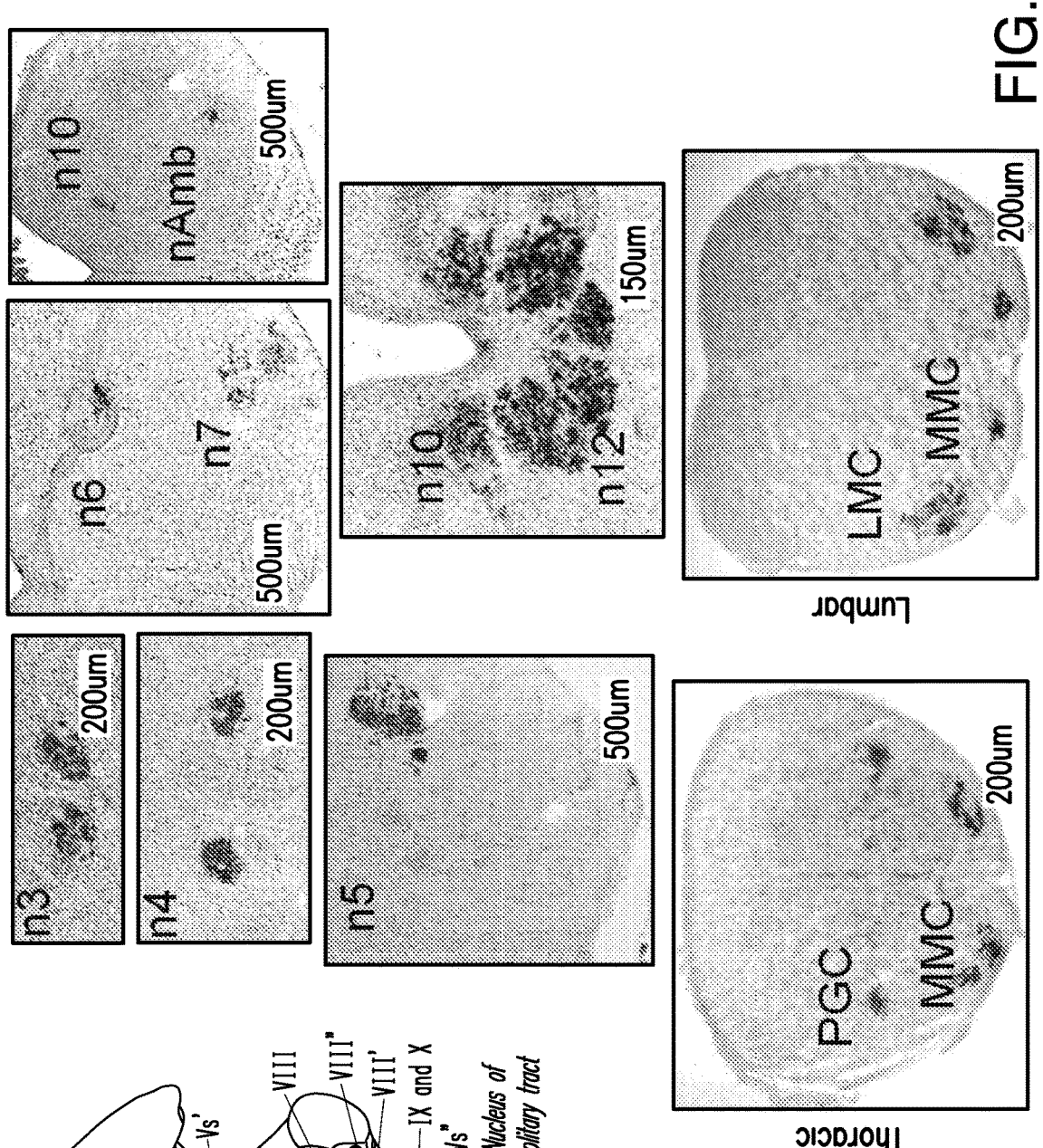

FIG. 12 shows miR-218 mRNA expression in brainstem and spinal motor neurons in the PO mouse central nervous system.

Figure 13:
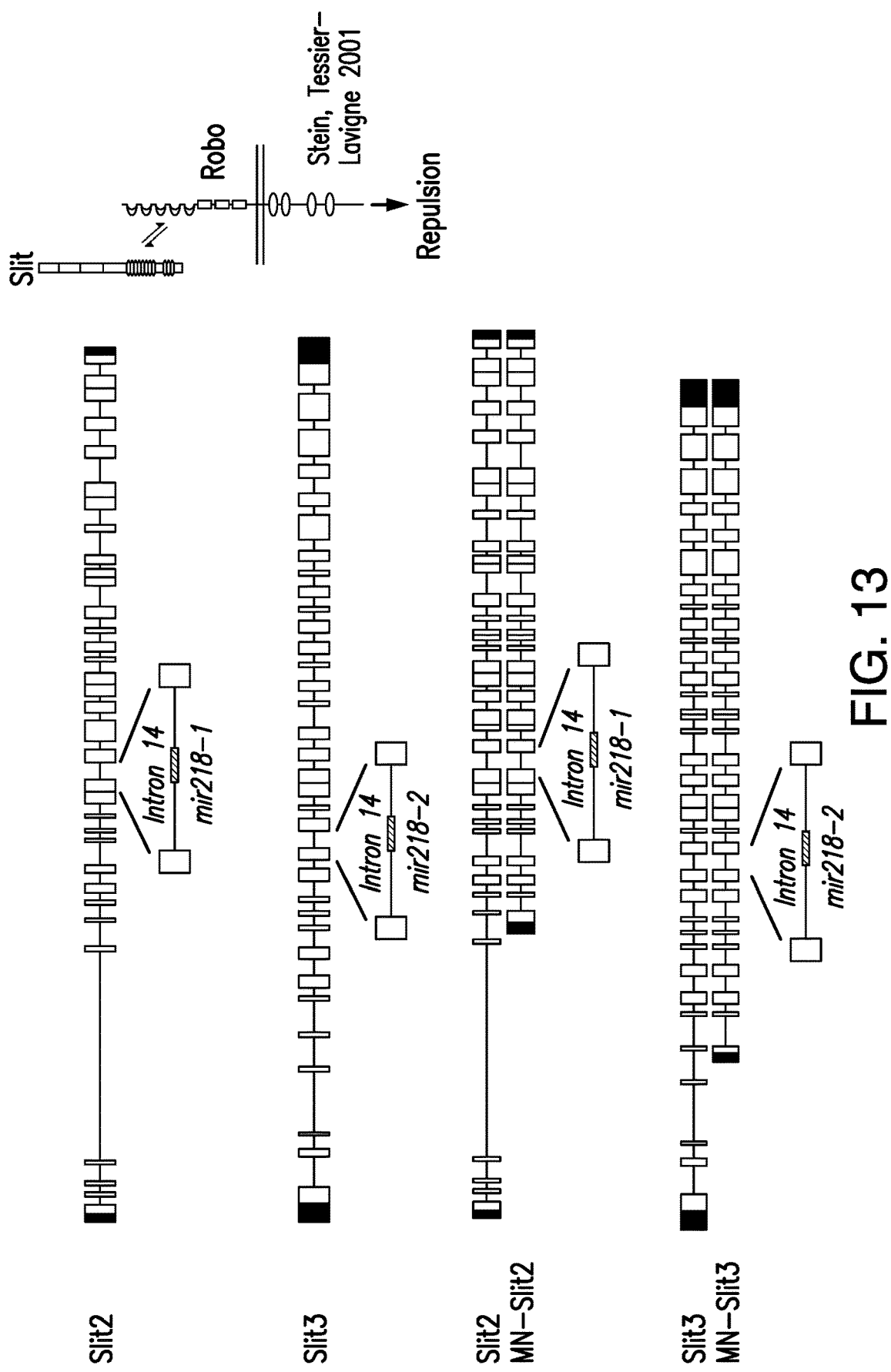

FIG. 13 Shows that miR-218 is encoded within intron 14, and upstream of exon 6, of the Slit2 and Slit3 genes, and that miR-218 expression is driven by a promoter independently of Slit2/3 expression.

Figure 14:
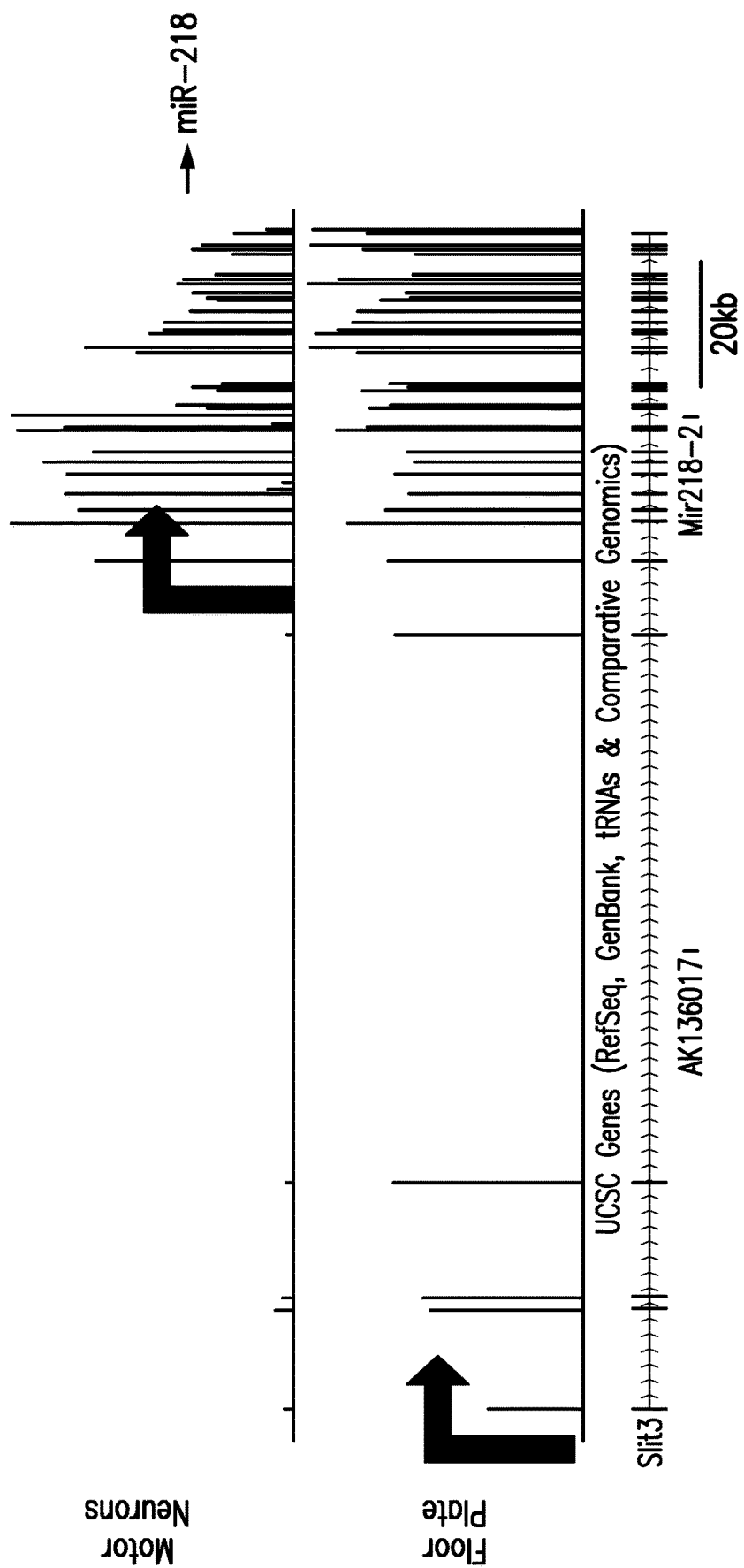
Figure 14:
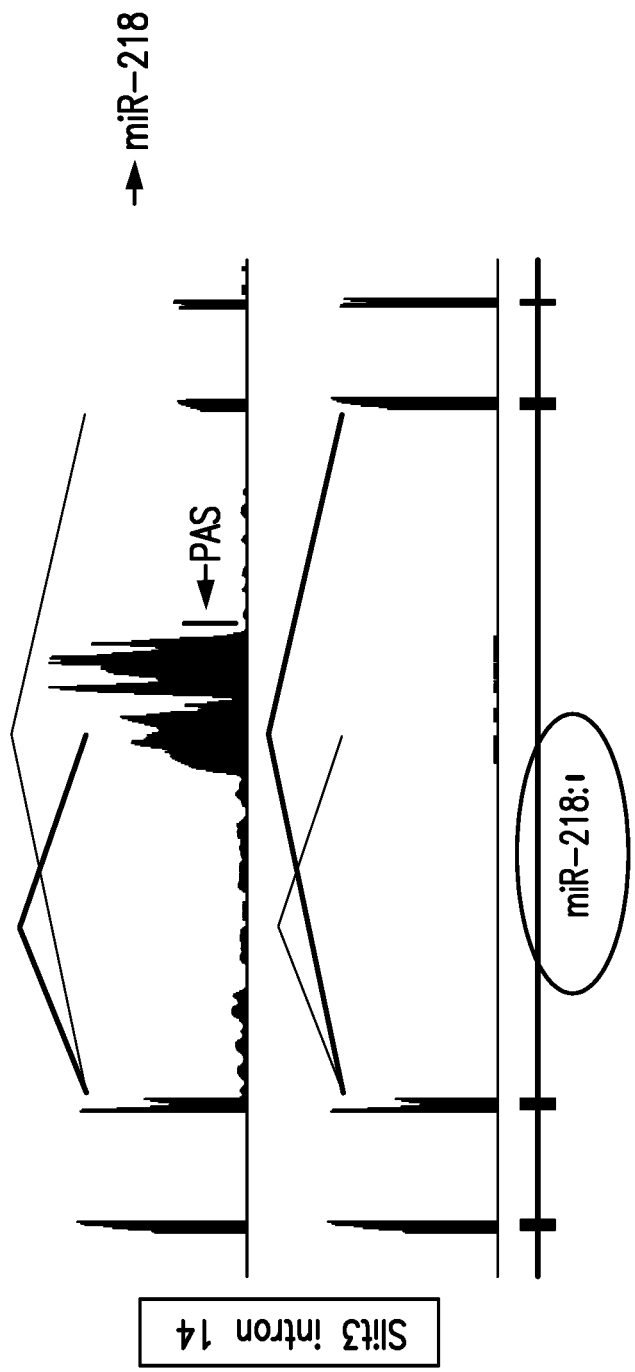
Figure 14:
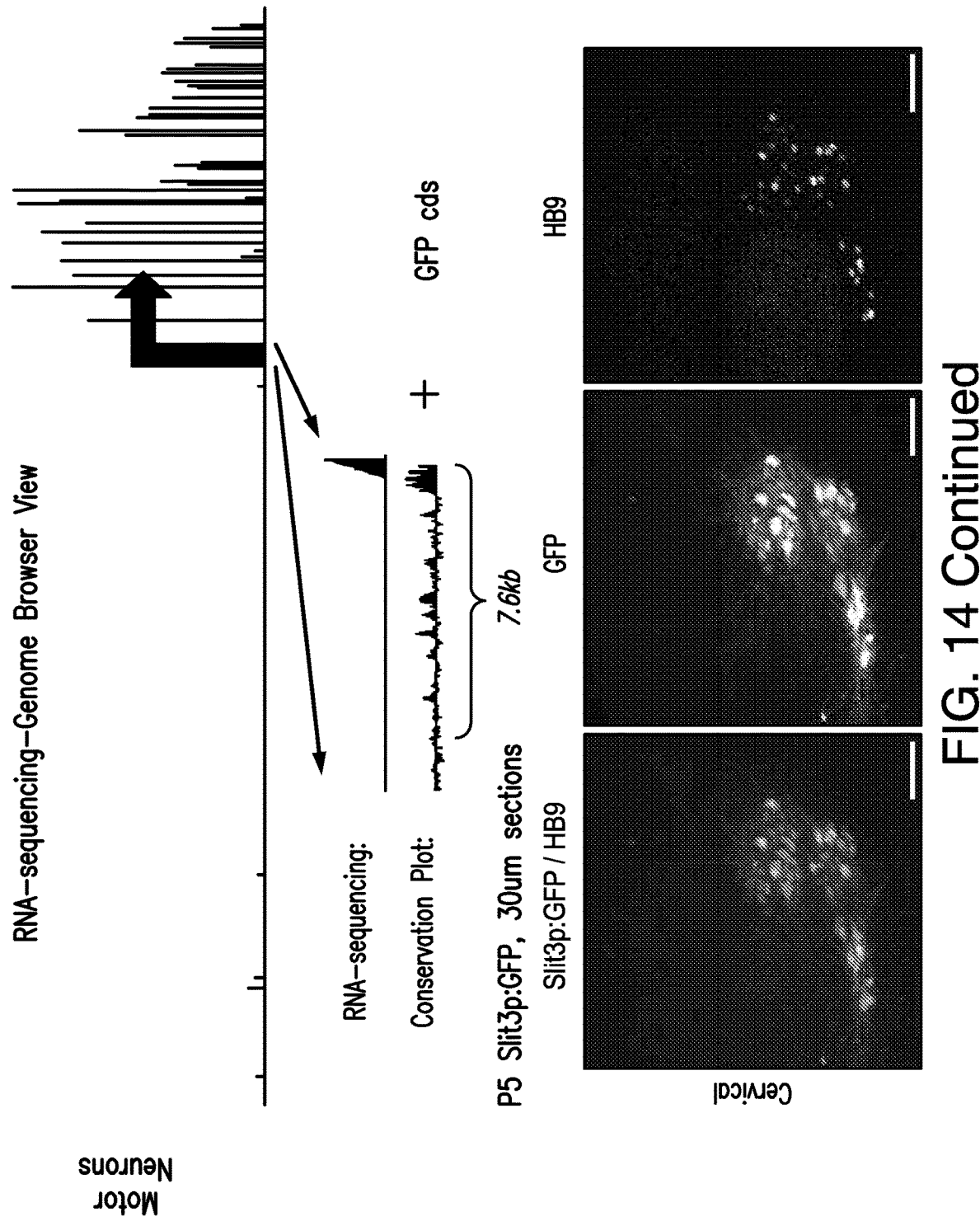
Figure 14:
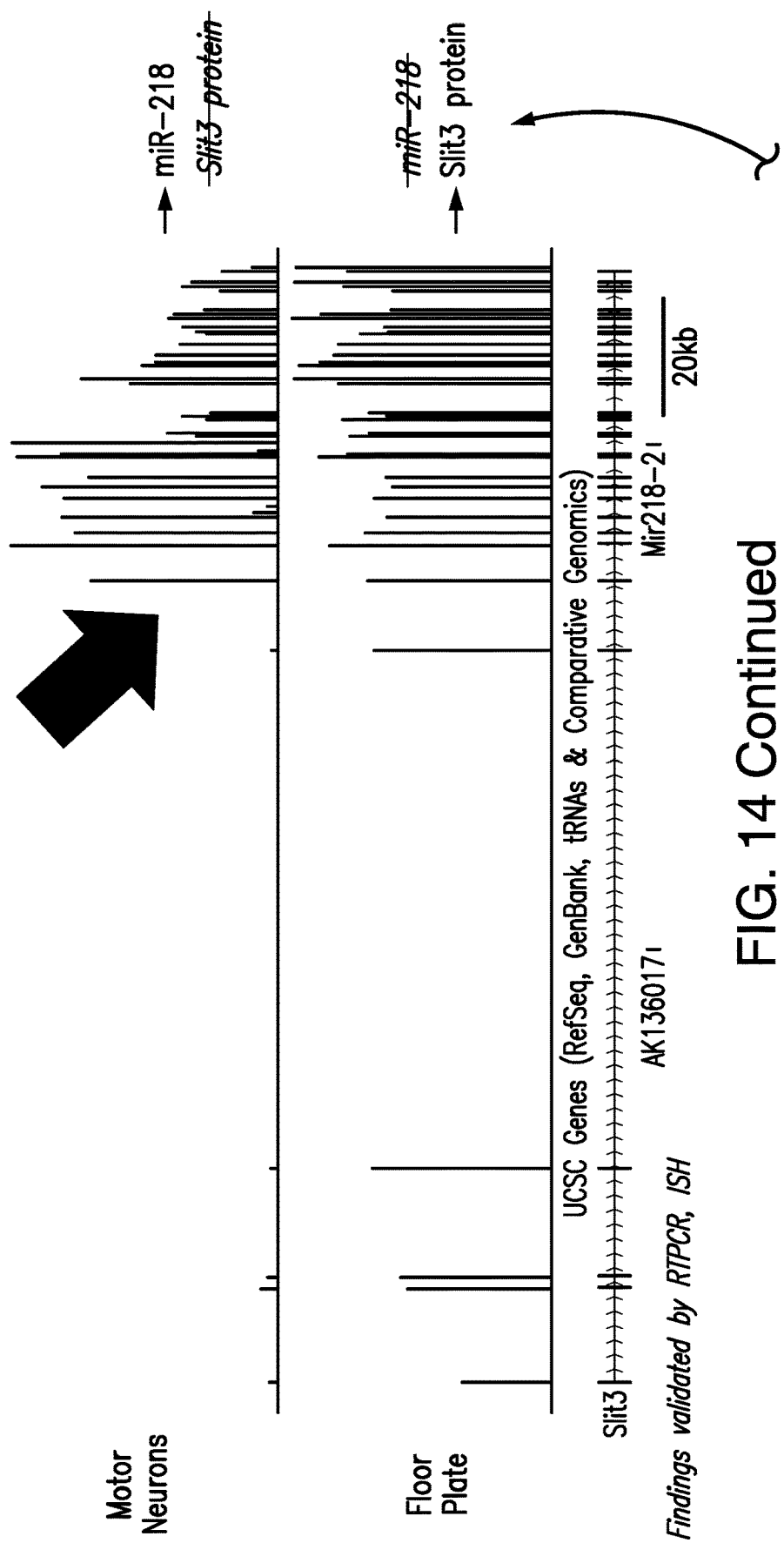
Figure 14:
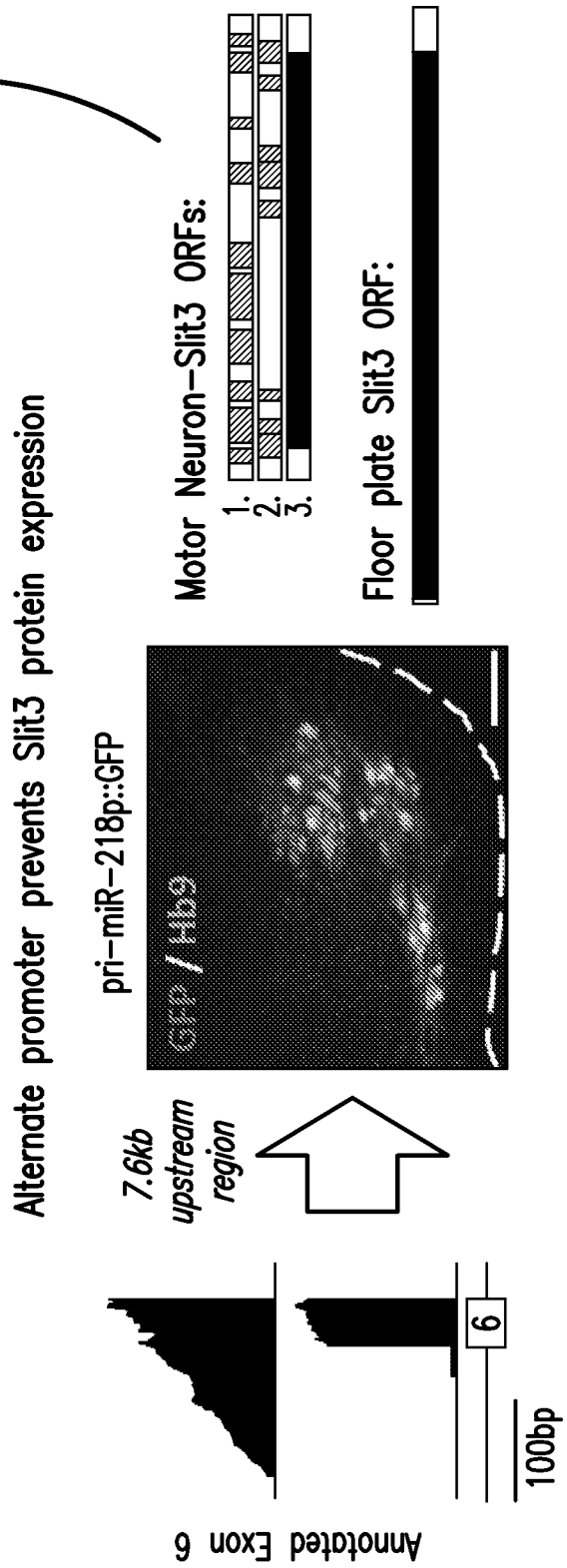

FIG. 14 shows that miR-218 promoter expression is motor neuron specific.

Figure 15:
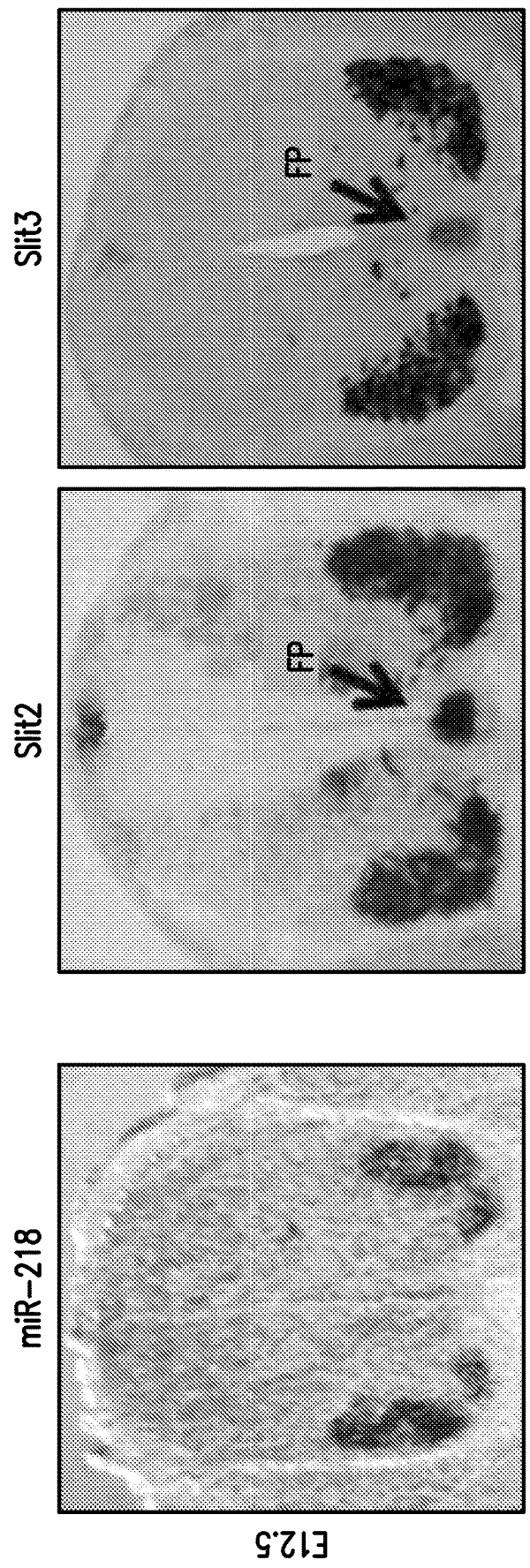
Figure 15:
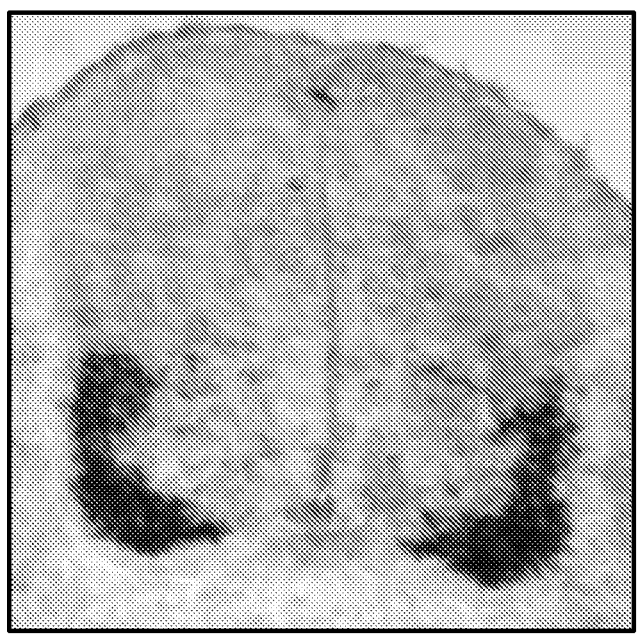

FIG. 15 shows that expression of miR-218 is more specific than Slit 2/3 in motor neurons of E12.5 mouse embryos. miR-218 was also expressed in motor neurons of Slit2$^{-/-}$ mice.

Figure 16:
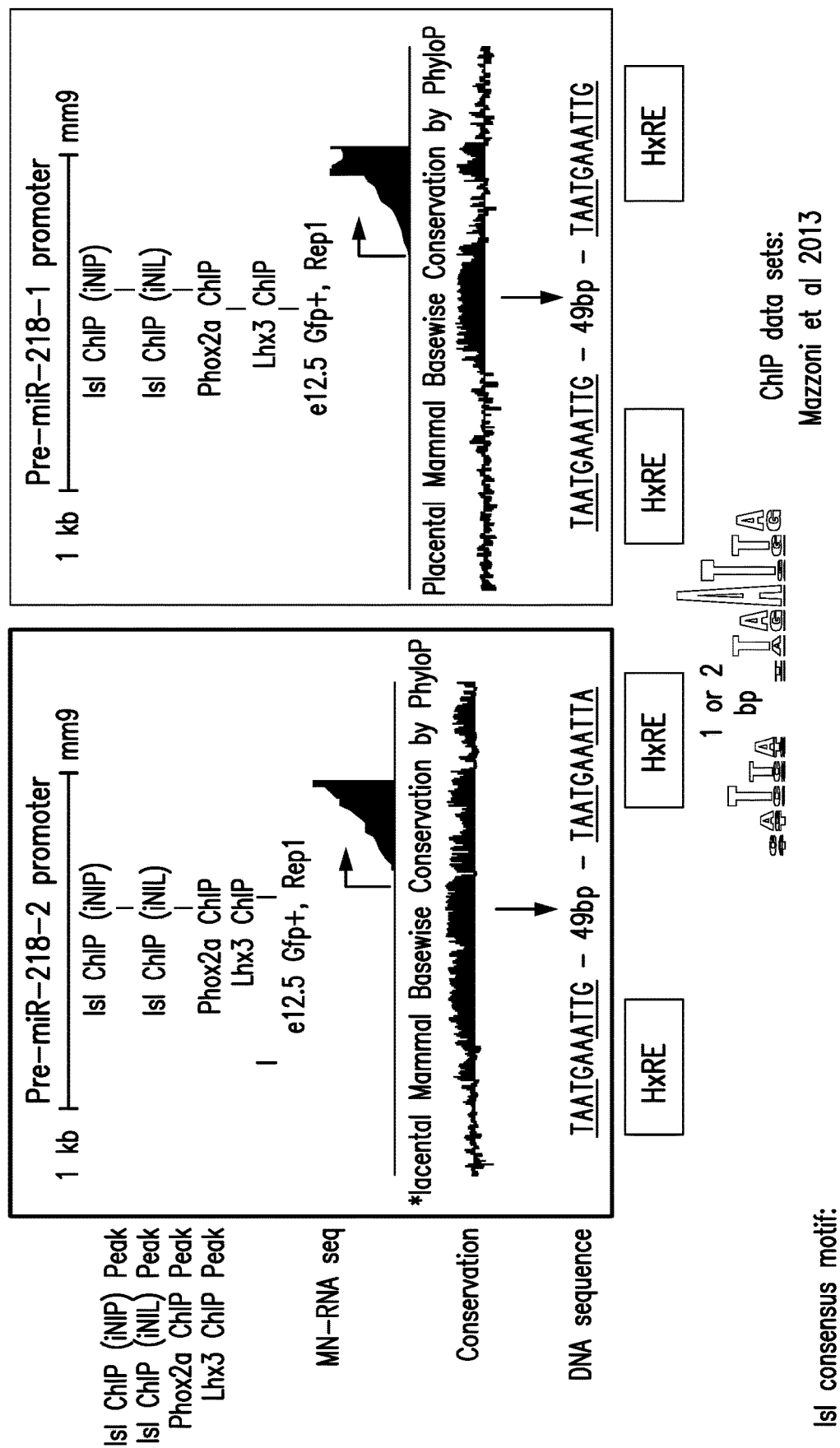

FIG. 16 shows that Isl-Lhx3 and Isl-Phox2a transcription factors bind to HxREs (HOX responsive elements) located within the proximal region of both miR-218-1 and miR-218-2 promoters to drive miR-218 expression. FIG. 16 discloses SEQ ID NOS 121-122, respectively, in order of appearance.

Figure 17:
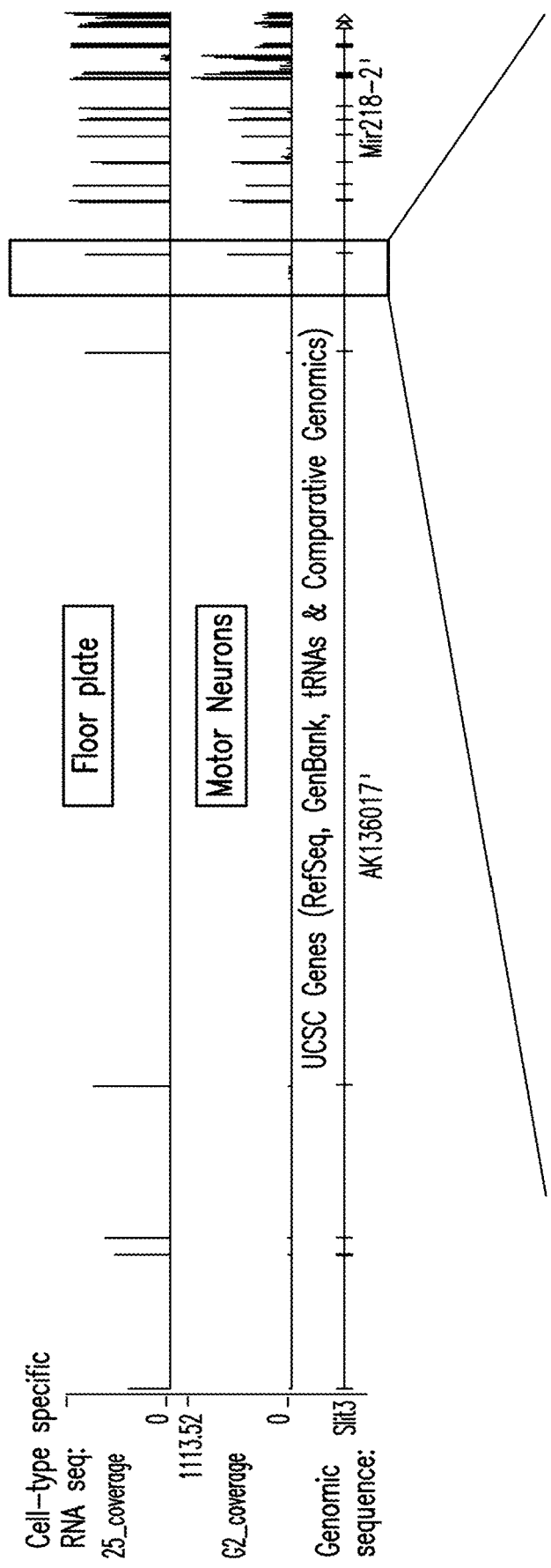
Figure 17:
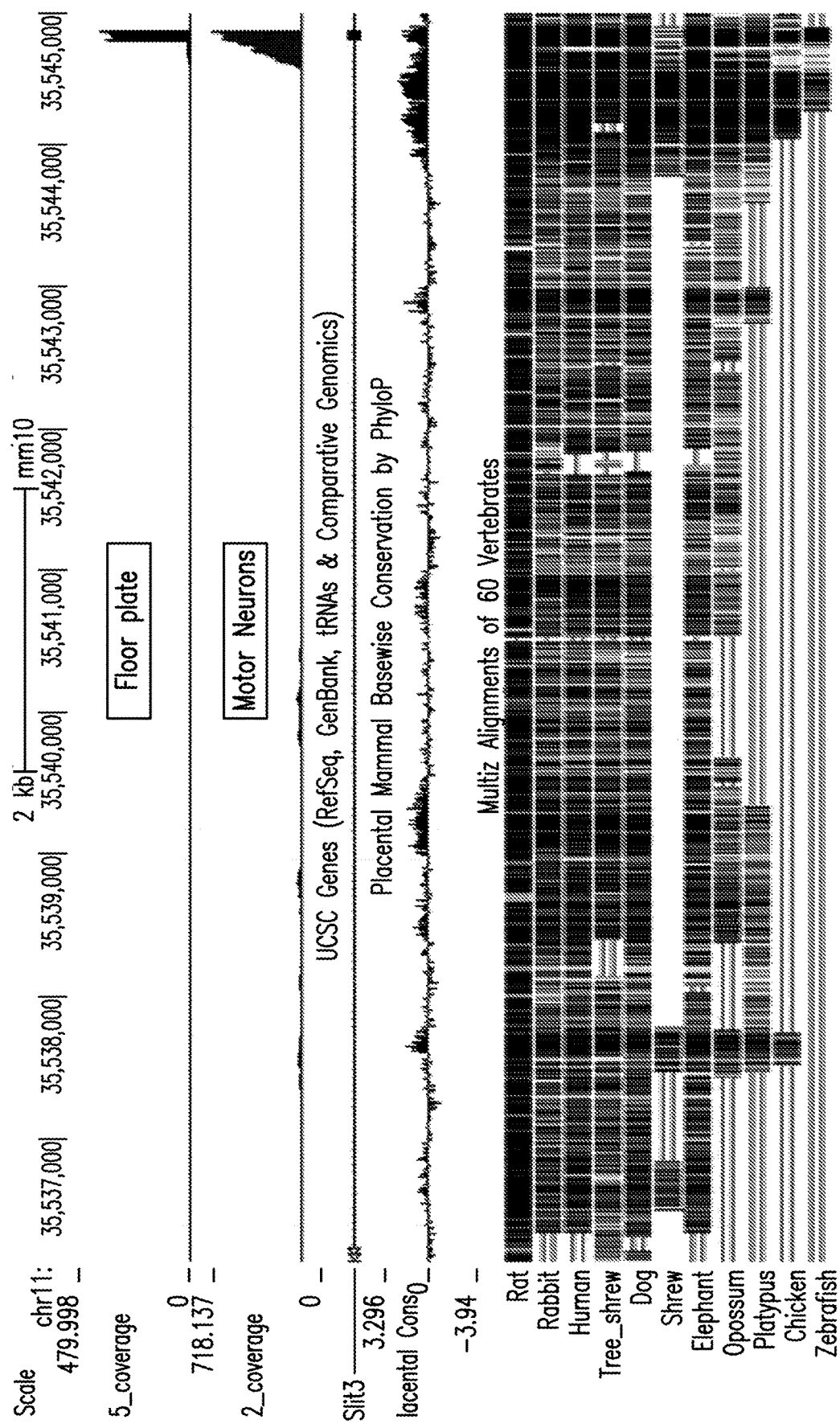

FIG. 17 shows sequence alignment of the 7.6 kb and 908 hp miR-218 promoters from various vertebrate species.

Figure 18:
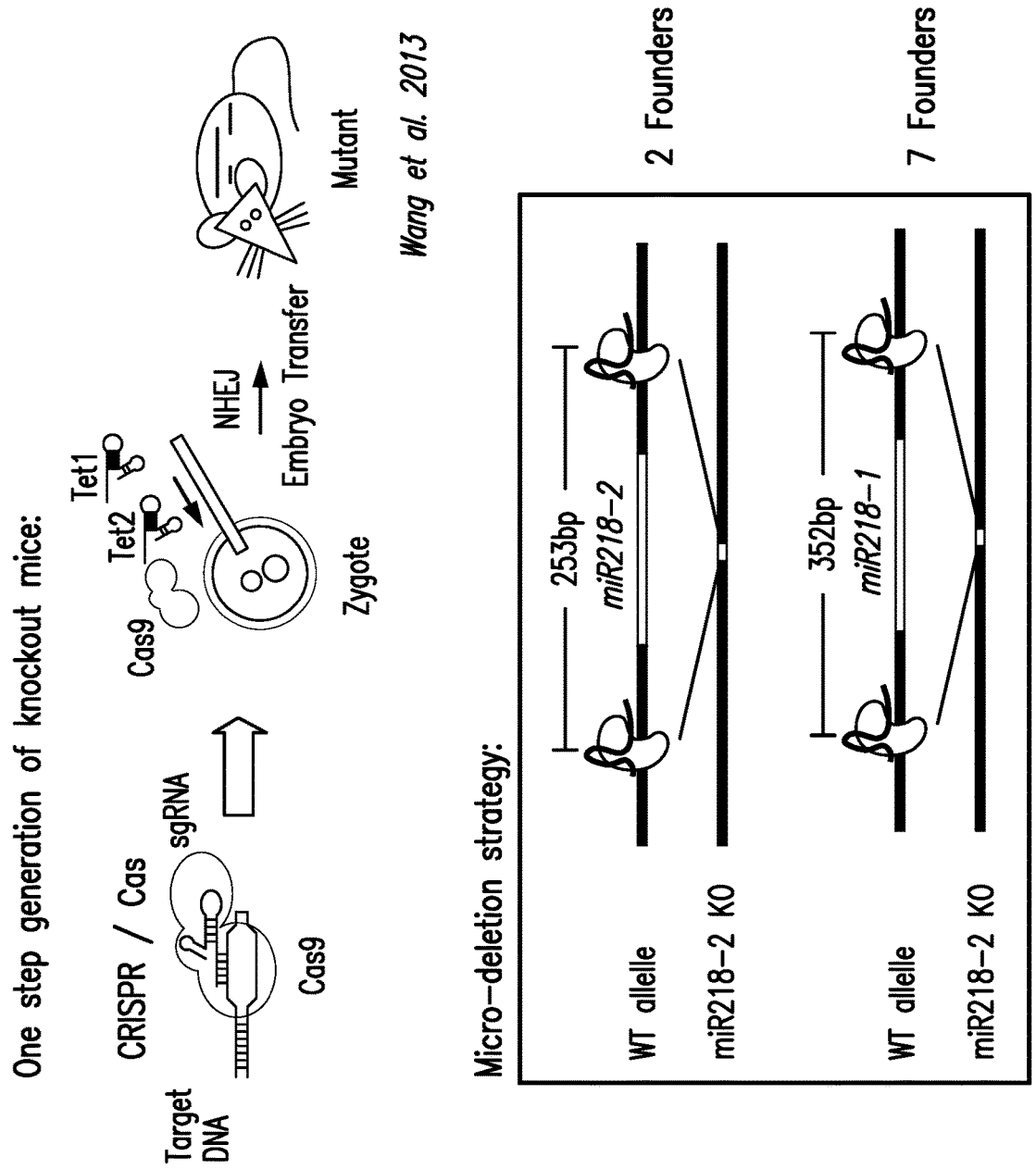

FIG. 18 shows the in vivo CRISPR-mediated micro-deletion of miR-218. miR-218 knockout (KO) mice and embryonic stem (ES) cells were generated.

Figure 19:
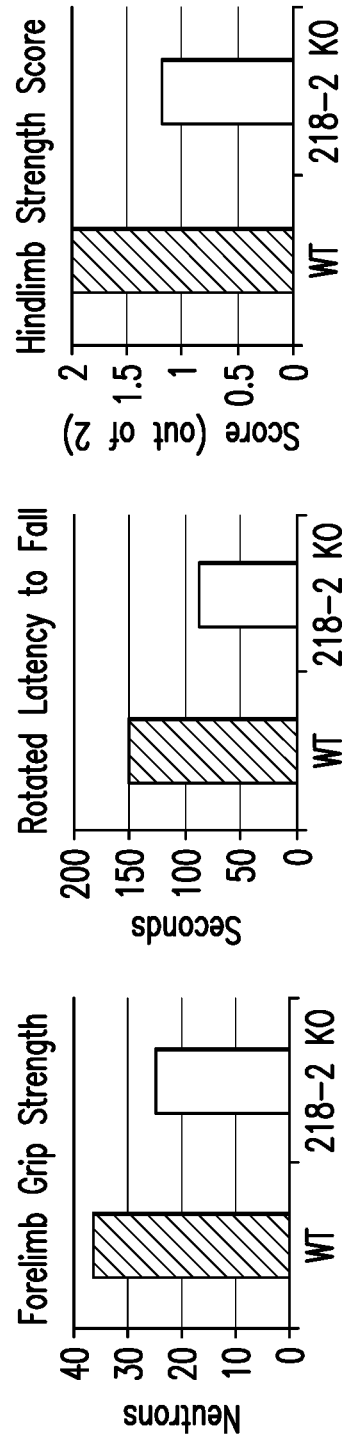
Figure 19:
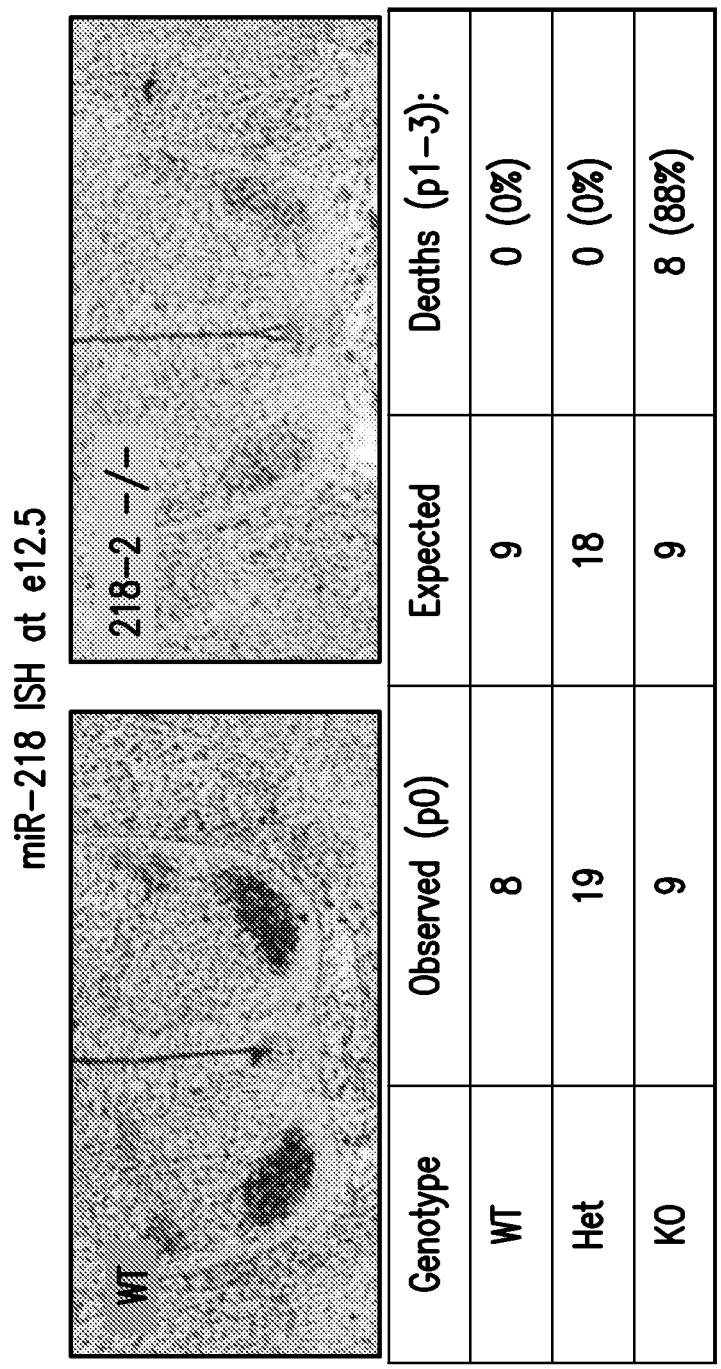

FIG. 19 shows that miR-218 knockout mice exhibited decreased viability and motor weakness.

Figure 20:
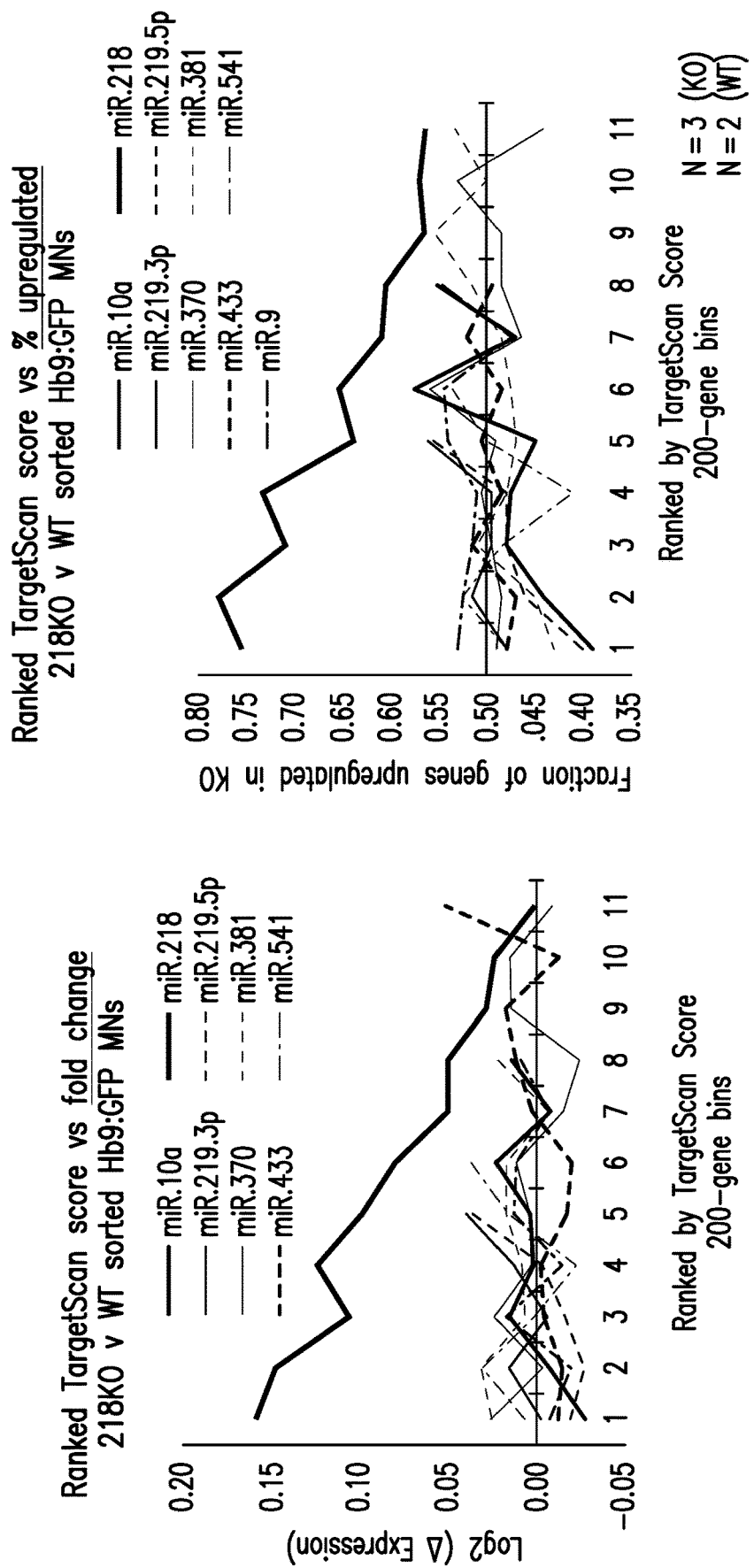

FIG. 20 shows that gene expression profiling of miR-218 KO motor neurons (E12.5) reveals de-repression of miR-218 predicted targets.

Figure 21:
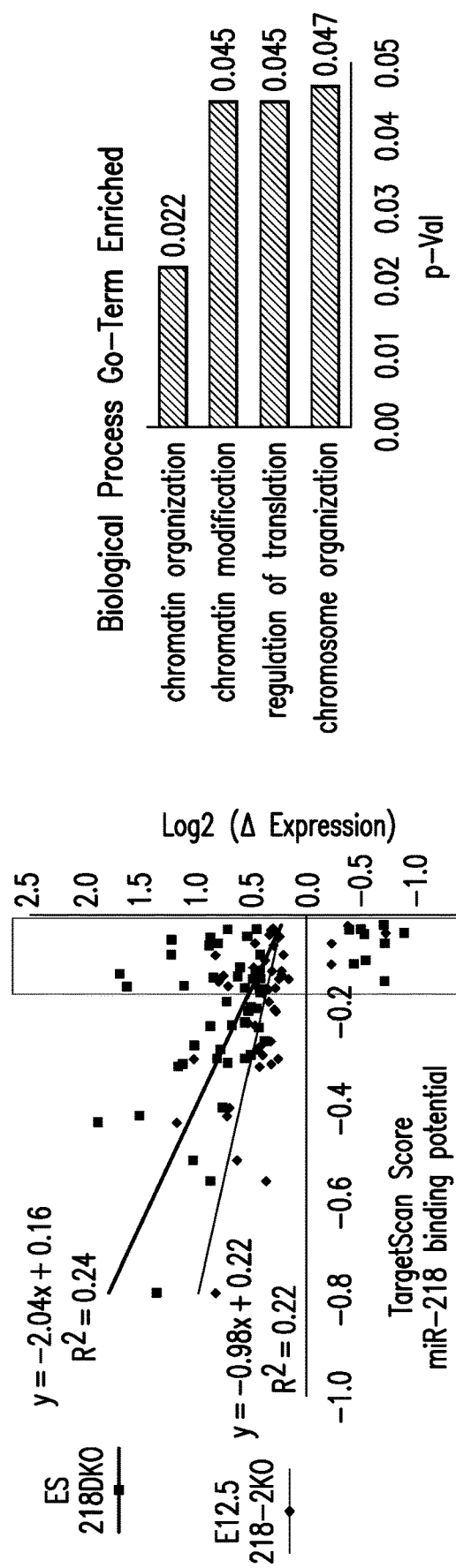

FIG. 21 shows that fifty-five miR-218 predicted targets are statistically misregulated in both in vivo KO mice (E12.5 mouse embryos) and in vitro KO cells (ES-derived motor neurons).

Figure 22:
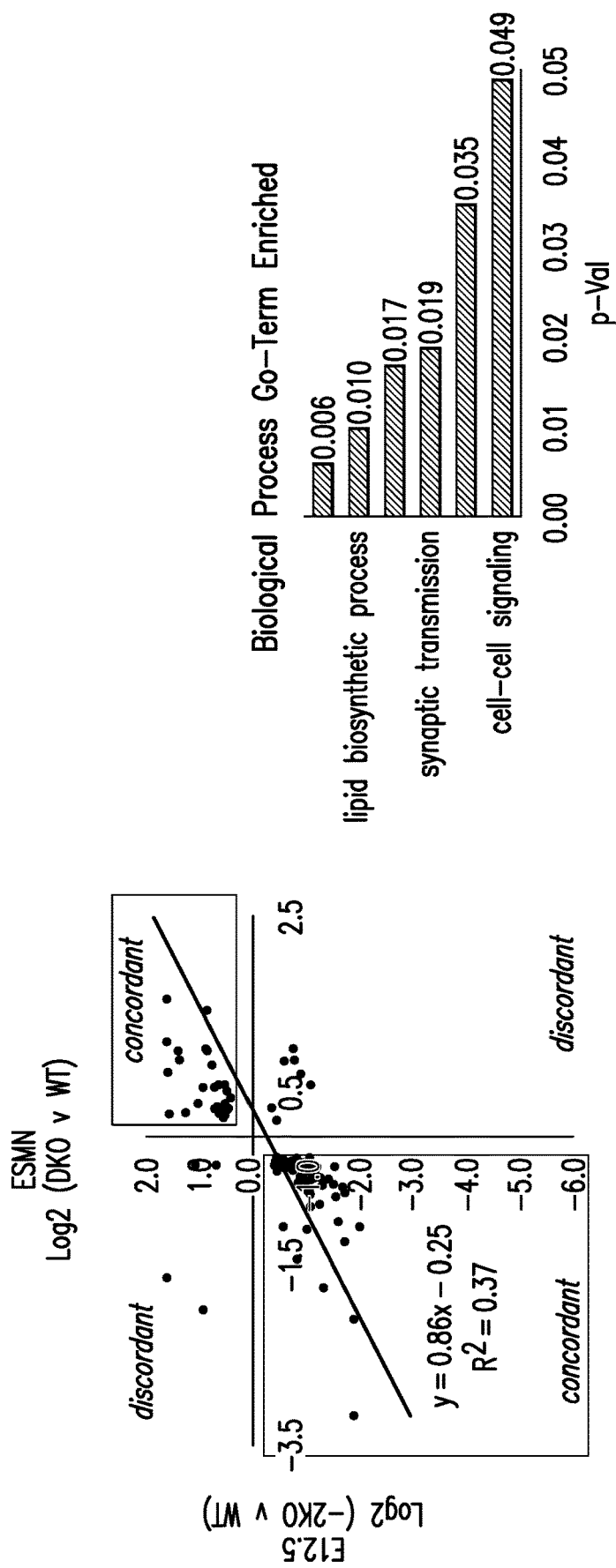

FIG. 22 shows that miR-218 indirectly activates genes involved in synaptic transmission.

FIG. 23 shows that miR-218 KO motor neuron transcriptome shifts towards a generic ventral interneuron identity.

Figure 24:
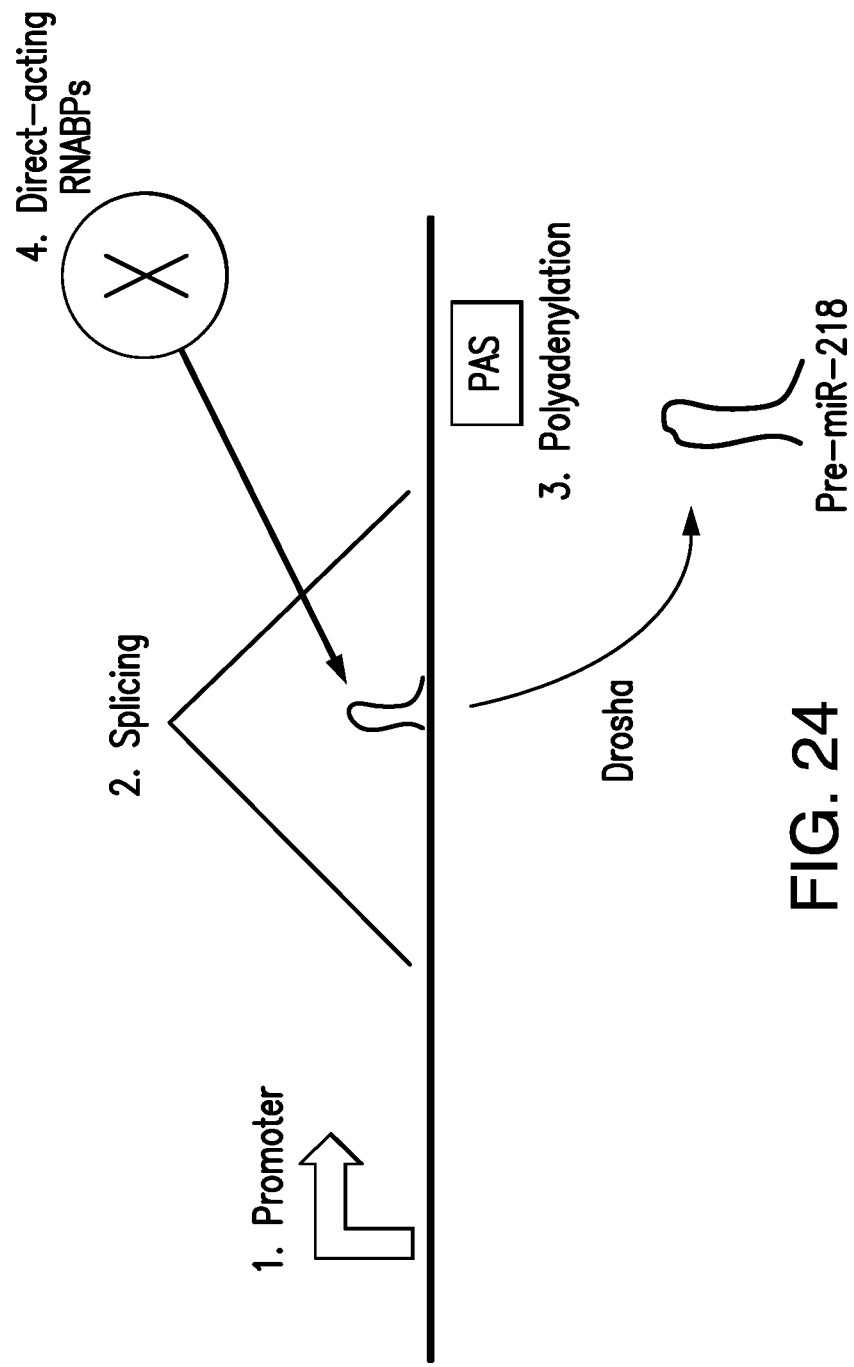

FIG. 24 shows proposed inter-relationships of alternative miR-218 (also referred to as pri-miR-218) processing in motor neurons.

Figure 25:
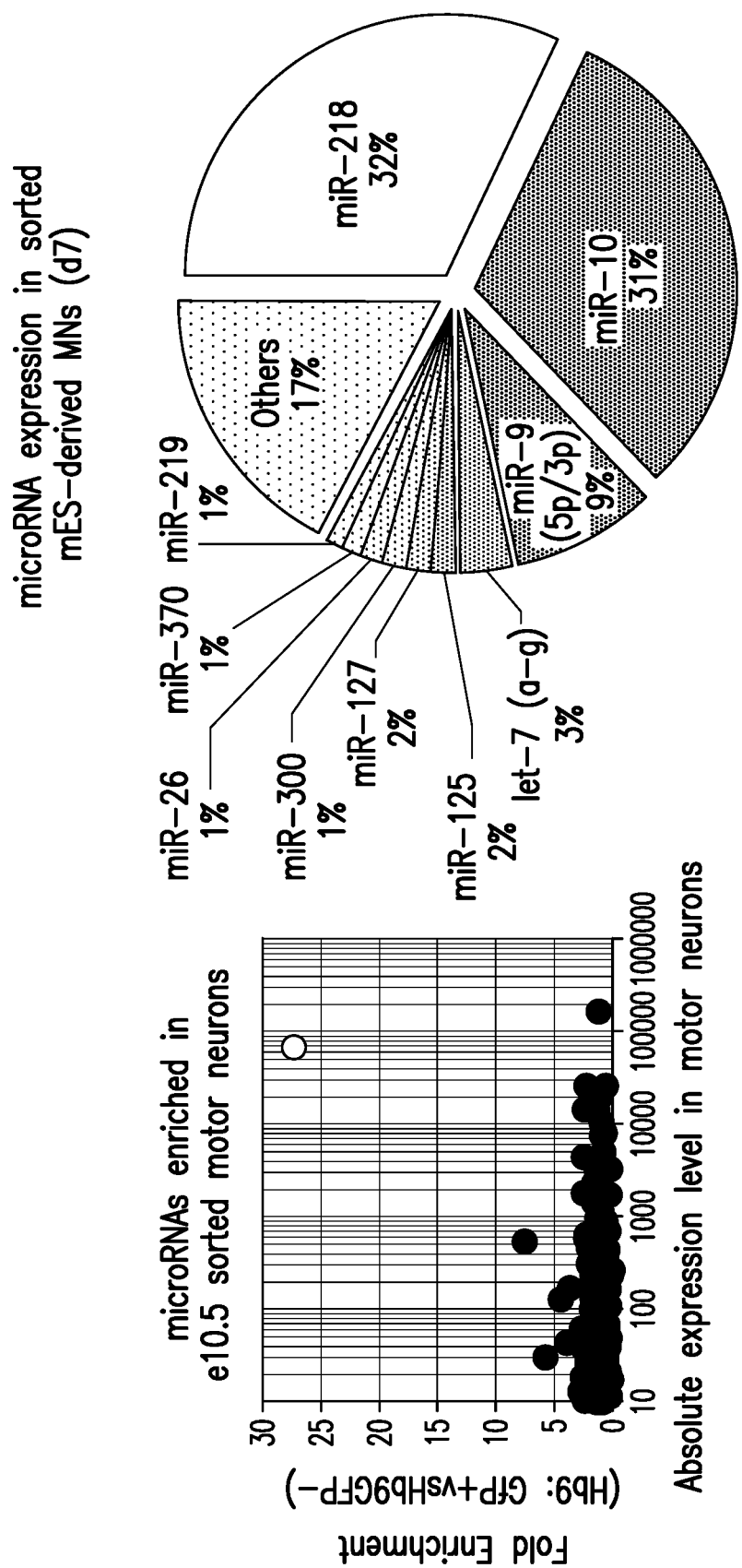

FIG. 25 shows microRNA profiling of Hb9:GFP-F motor neurons by RNA-seq.

Figure 26D:
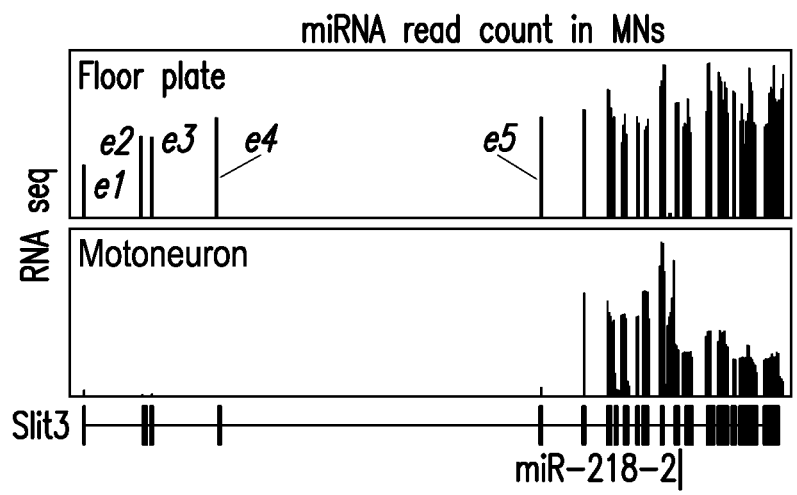
Figure 26E:
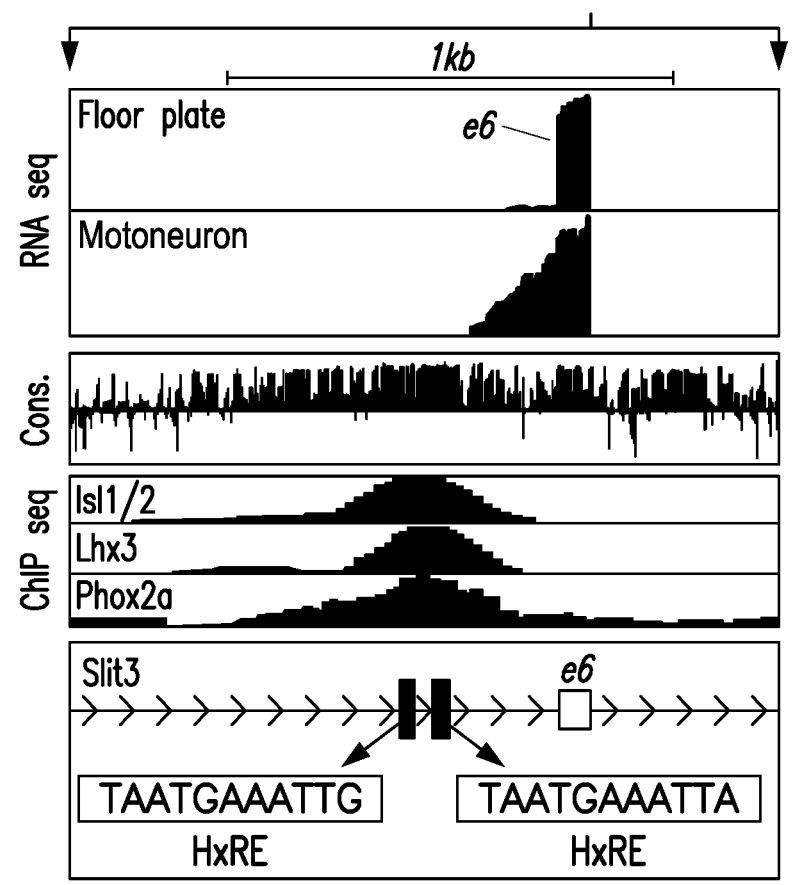

FIG. 26A-H shows abundant and specific expression of miR-218 in spinal and cranial motoneuron subtypes. (A) Murine microRNA expression (x-axis) versus enrichment (Hb9::gfp+motoneurons versus Hb9: :gfp− non-motoneurons, y-axis) (n=2). (B) miR-218 in situ hybridization in whole mount and transverse section at El 1.5 (arrowheads identify motor columns). (C) miR-218 co-localizes with ChAT+motoneurons at P10. (D, E) PolyA+RNAseq reads from E12.5 floor plate and motoneurons and motoneuron-specifying transcription factor ChIP peaks and HxRE DNA binding motifs at the Slit3 locus containing pre-miR-218-2. FIG. 26E discloses SEQ ID NOS 74 and 75, respectively, in order of appearance. (F) Transcription of miR-218 in motoneurons by alternative promoters. (G, H) tg(218-2:: eGFP) mice. (G) Expression of eGFP in spinal and brainstem motoneurons of the CNS, and (H) in miR-218+motor nuclei nX and nXII. Scale bars: (C) 50 μm (I) 200 μm.

FIG. 27A-J shows Loss of miR-218 results in systemic neuromuscular failure, and motoneuron cell loss and hyper-excitability. (A) CRISPR/Cas9-mediated multiplexed micro-deletions of pre-miR-218-1 and pre-miR-218-2 from the mouse genome. (B) miR-218 in situ hybridization signal in control and 218$^{DKO}$ E18.5 spinal cords. (C) Cesarean-delivered 218$^{DKO}$ E18.5 embryos exhibit flaccid paralysis and die within minutes. (D) Decreased intramuscular branching (arrows) of E14.5 motor nerves in tg(218-2::eGFP); 218$^{DKO}$ embryos (deep peroneal nerve). (E and F) In 218$^{DKO}$ embryos, (E) NMJs exhibit abnormal morphology, and (F) most limb AChR$^+$ clusters are aneural (n=3). (G and H) Motoneuron counts at E12.5 (n=4 and 3), and E18.5 (n=4) across spinal segments. (I and J) (I) Representative traces of control and 218$^{DKO}$ motoneurons after intracellular current injection, and (J) rheobase quantification (n=9 and 5). Statistics: (F, G, H) standard deviation and results of two-tailed t-test are shown. (J) SEM shown, non-parametric Mann-Whitney t-test results shown. * and *** denotes p-value<0.05 and p-value<0.001. n.s. denotes not significant. Scale bars: (B, D and H) 150 µm, (E) 50 µm.

FIG. 28A-E shows miR-218 represses an extensive genetic network in motoneurons. (A) Volcano plot (mRNA fold difference versus p-value) of 218$^{DKO}$ versus wild type motoneurons of genes with predicted miR-218 binding sites (TargetScan6, n=6 and 2). 333 of these genes (designated TARGET$^{218}$ genes) are significantly de-repressed in 218$^{DKO}$ motoneurons. TARGET$^{218}$ genes involved in neurotransmitter transport are labelled. (B) Motoneurons and VI, V2a, and V3 interneuron subpopulations derive from adjacent progenitor domains (p1, p2, pMN, p3) and were labelled with transgenes or Cre-reporters for FACS-isolation and RNA sequencing. (C) TARGET$^{218}$ genes are expressed at low levels in motoneurons relative to each of V1, V2a and V3 interneurons. (D) Most TARGET$^{218}$ genes are expressed lower in motoneurons compared to all three of V1, V2a and V3 interneurons. (E) Hierarchical clustering of TARGET$^{218}$ gene expression in wild type motoneuron (WT MN, six replicates), 218$^{DKO}$ motoneuron (218$^{DKO}$ MN, two replicates) and interneuron subpopulations (V1 IN, V2a IN, V3 IN).

Figure 29A:
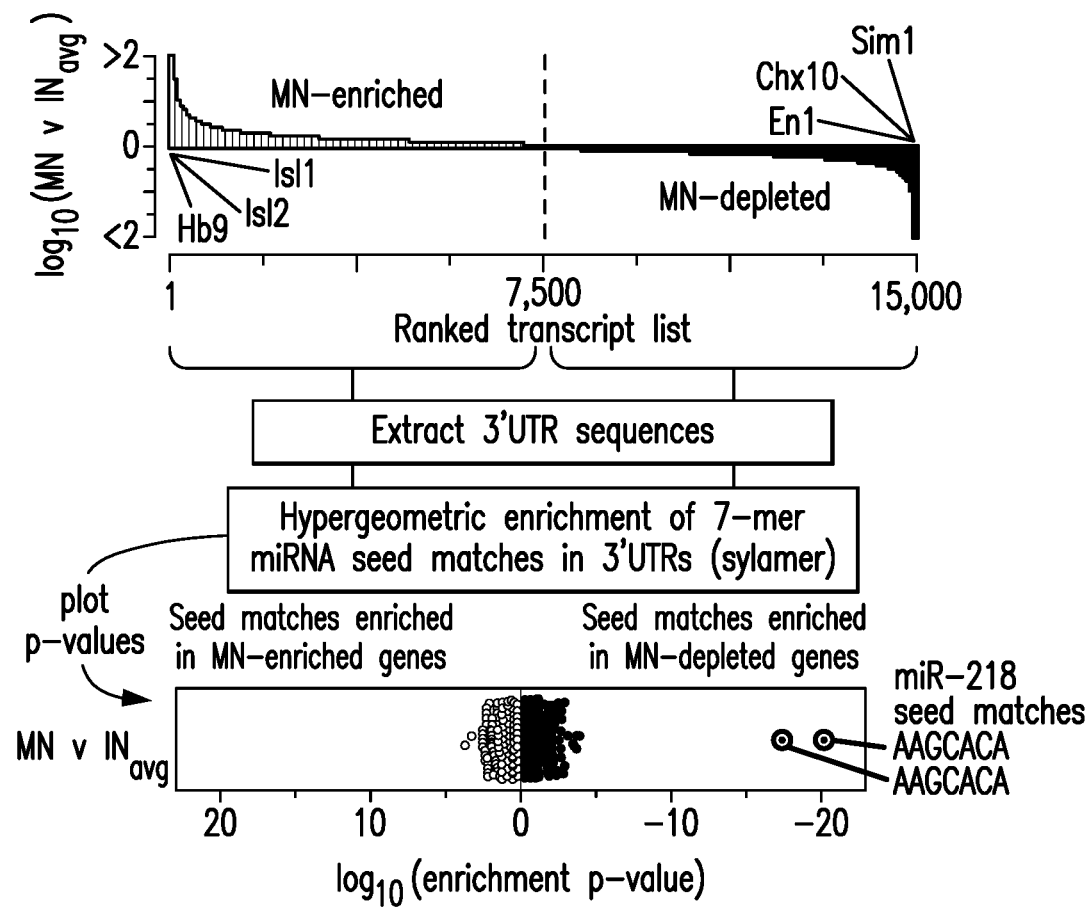
Figure 29B:
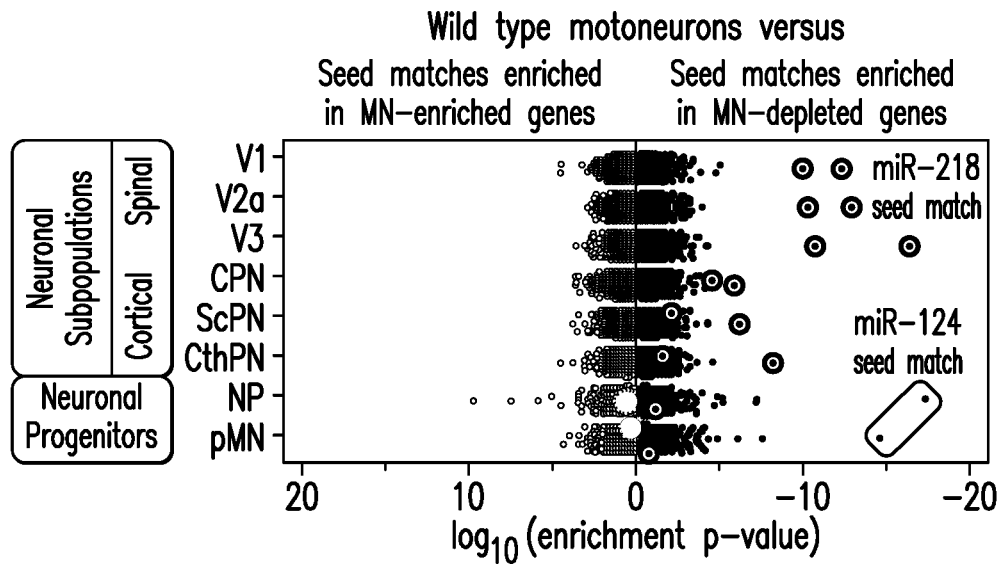
Figure 29C:
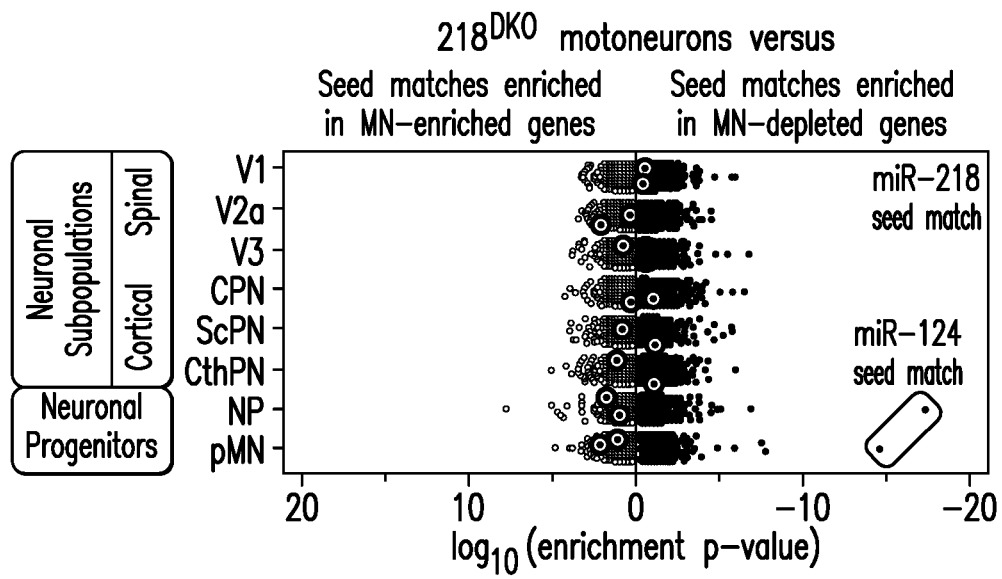
Figure 30A:
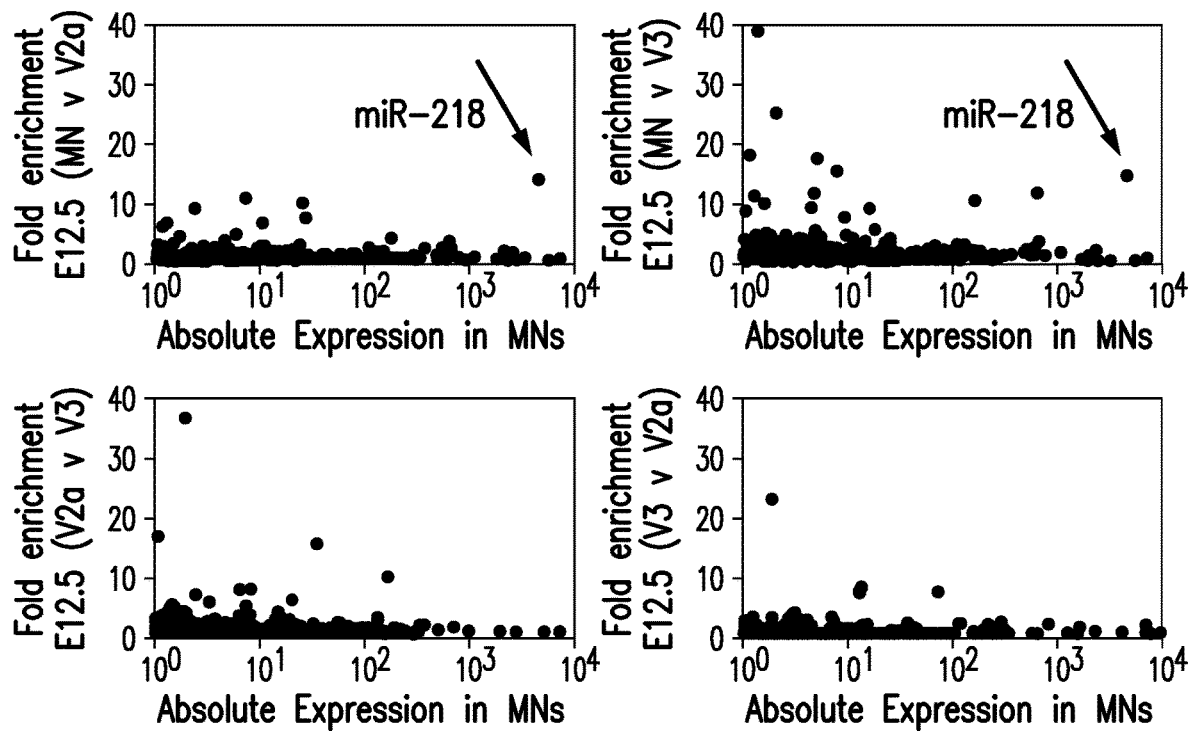
Figure 30B:
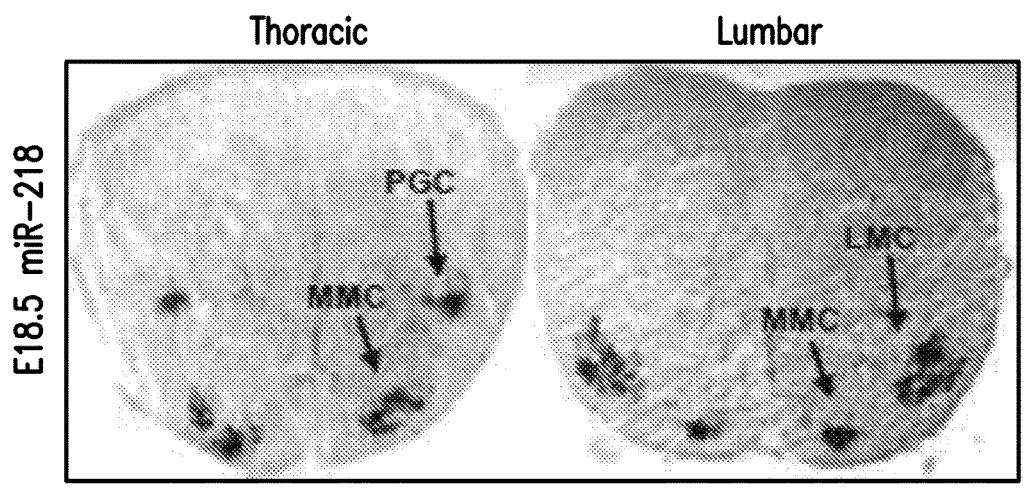

FIG. 29A-C shows miR-218 represses a neuronal-gene network in motoneurons. (A) 7mer seed matches for miR-218 (AGCACAA (SEQ ID NO: 70) and AAGCACA (SEQ ID NO: 69), red circles), but not those of other microRNAs, are significantly and specifically enriched in the 3'UTRs of genes expressed low in motoneurons relative to an average of V1/V2a/V3 interneuron populations (IN$_{avg}$). (B) Genes expressed lower in wild type motoneurons versus individual spinal and cortical (24) neuronal subpopulations were most enriched for miR-218 seed matches. (C) miR-218 seed matches are not enriched in genes expressed higher or lower in 218$^{DKO}$ motoneurons versus other neuronal populations. Genes expressed lower in wild type (B) or 218$^{DKO}$ (C) motoneurons versus neuronal progenitors were most enriched for the seed match to miR-124 (GTGCCTT). CPN, callosal, ScPN, subcerebral, CthPN subplate neurons, NP, mES-derived neuronal progenitors, pMN, FACS-purified Olig2$^+$mES-derived neuronal progenitors.

FIG. 30A-G shows miR-218 is abundantly and specifically expressed across motoneuron subtypes. (A) miRNA sequencing was performed on FACS-isolated motoneurons (Hb9:gfp), V2a interneurons (Chx10:Cre; Rosa:LNL:tdtomato) and V3 interneurons (Siml:Cre; Rosa:LNL:tdtomato) from E12.5 dissected spinal cord tissue. No other miRNAs show comparable enrichment and abundance as miR-218 in motoneurons. (B and C) Sectioning and miR-218 in situ hybridization of the spinal cord (B) and brainstem (C) at E18.5. miR-218 was detected in the medial motor column (MMC), lateral motor column (LMC), preganglionic motor column (PGC), and all cranial motor nuclei: nuclei III (nIII), nuclei IV (nIV), nuclei V (nV), nuclei VI (nVI), nuclei VII (nVII), nuclei X (nX), and the ambiguous nucleus (nAmb). Staining of cranial nuclei XII (nXII) is displayed in FIG. 1H. (D) miR-218 is expressed in both α-(NeuN+,ChAT+) and γ-(NeuN−,ChAT+, black arrowheads) motoneurons located in the ventrolateral spinal cord at P10, as determined by dual immunohistochemistry and in situ hybridization. (E) miR-218 is not detected in ChAT+ interneurons (arrows) located in the dorsal spinal cord at P10. (F) miR-218 expression is detected in motoneurons of the human embryonic spinal cord (LMC and MMC shown here). (G) miR-218 expression is detected in the adult spinal cord in ventrolateral motoneurons.

Figure 31A:
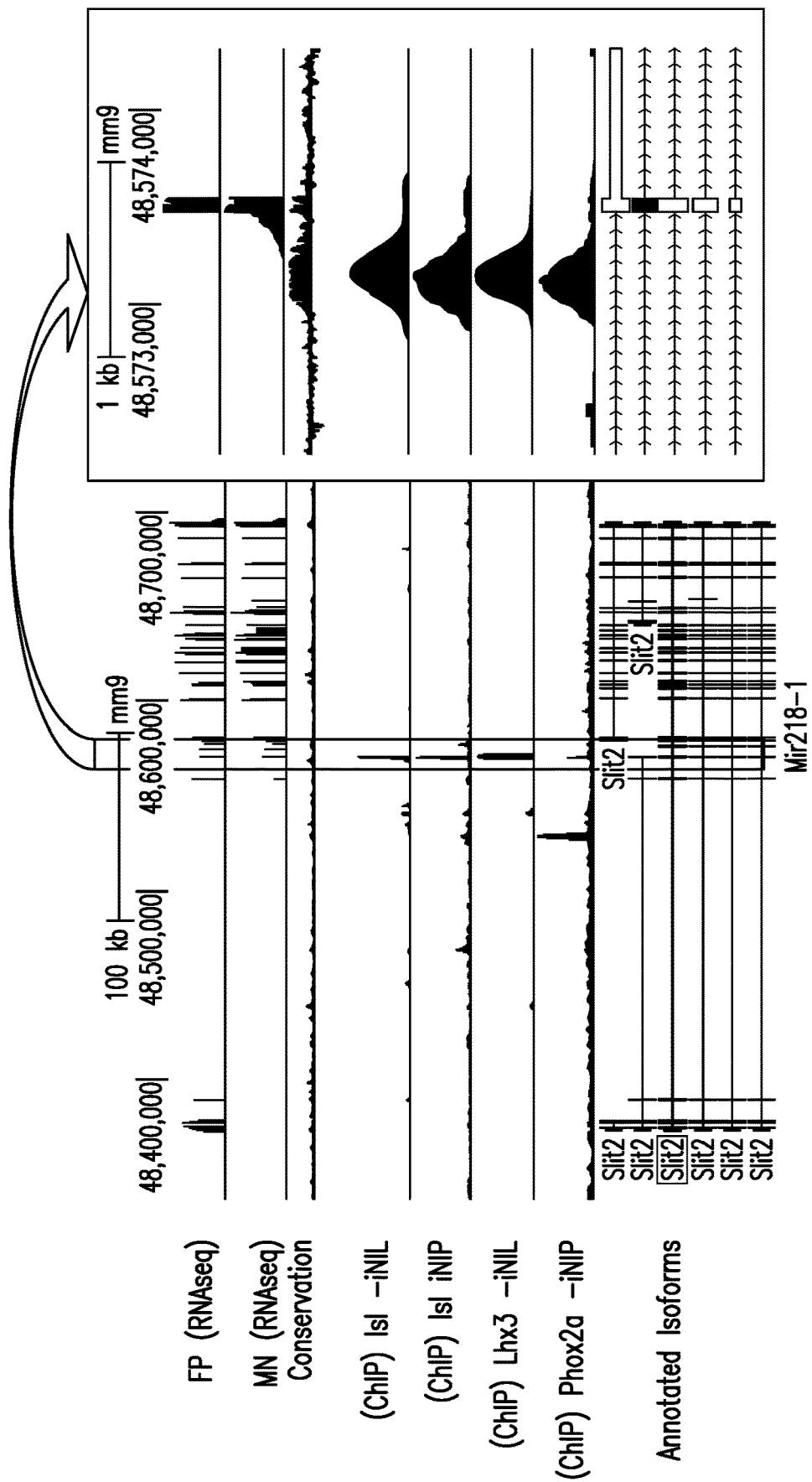
Figure 31B:
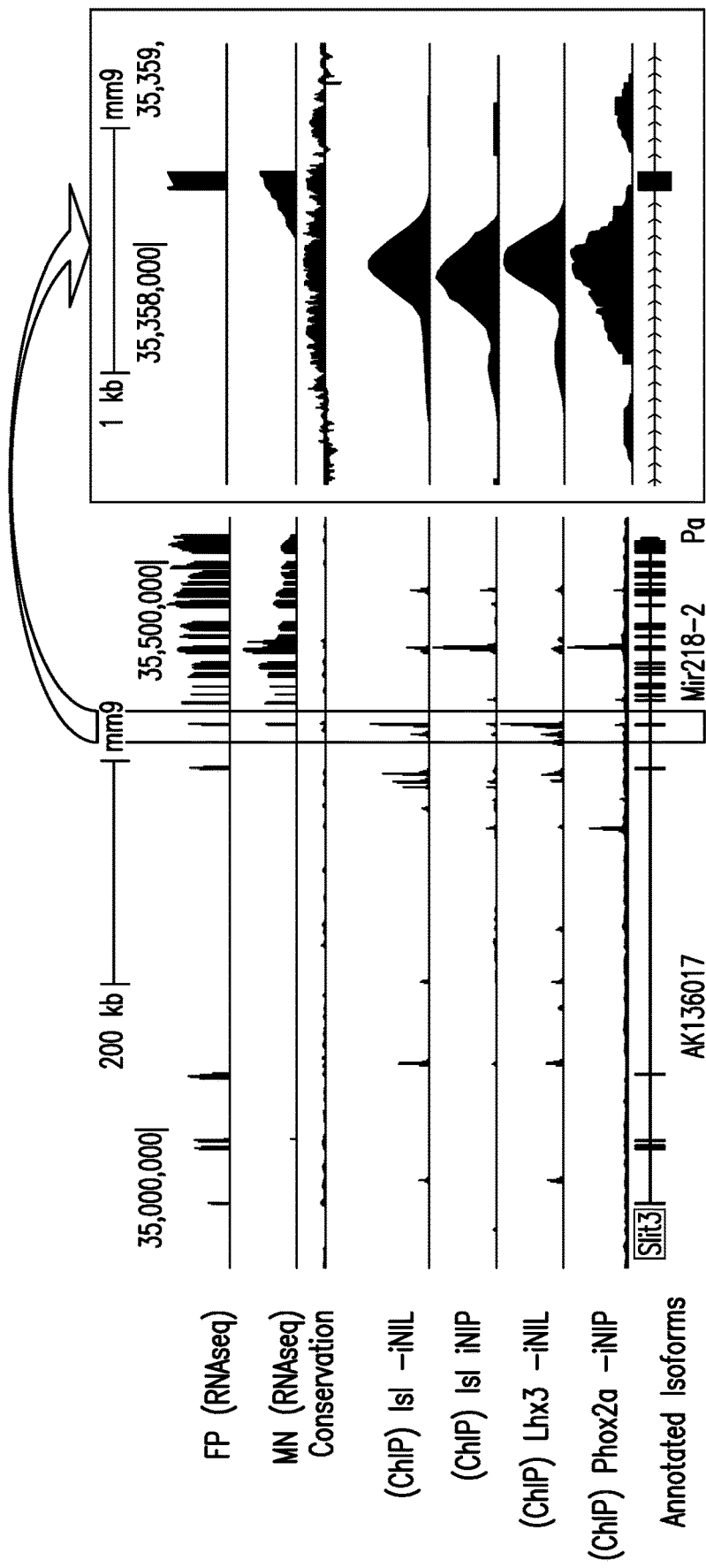
Figure 31C:
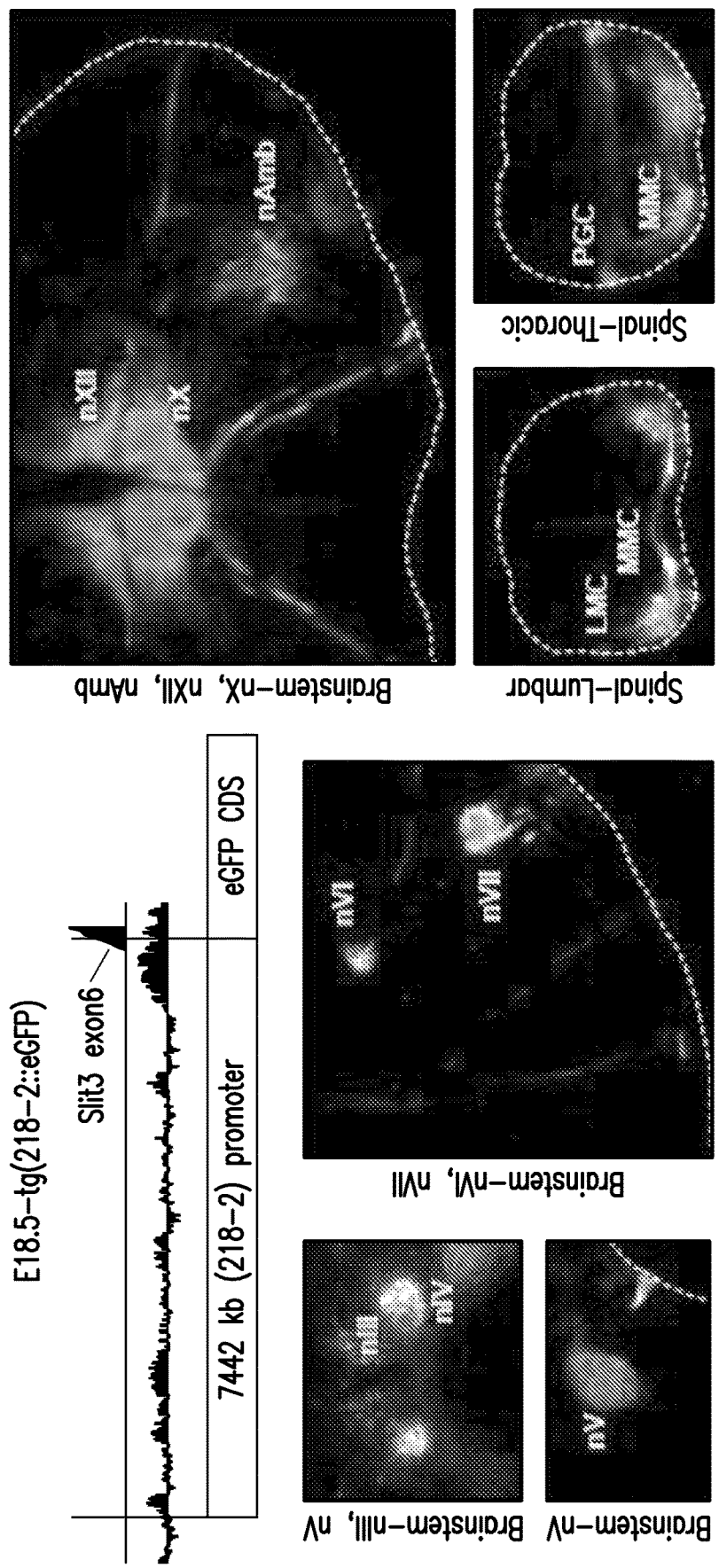

FIG. 31A-C shows Alternative, motoneuron-specific promoters drive transcription of miR-218-1 and miR-218-2. (A and B) UCSC genome browser views of Slit2 (A) and Slit3 (B) genomic loci showing (sequentially from top to bottom) RNA sequencing reads from the floor plate and motoneurons, evolutionary conservation, ChIP sequencing data (9) of Is11, Lhx3 and Phox2a in ES-derived cranial (iNIP) and spinal (iNIL) motoneurons, and annotated gene isoforms. Large ChIP sequencing peaks for Is11, Lhx3, and Phox2a are found upstream of exon 6 of both Slit2 and Slit3. (C) The 7.6 kb genomic region upstream of Slit3-exon 6 contains many evolutionarily conserved regions which are putative Is11/Lhx3/Phox2-responsive enhancer and promoter elements. This segment was cloned into a promoter-less vector upstream of the coding sequence of eGFP. A transgenic mouse line generated from this construct tg(218-2::eGFP) specifically expresses eGFP in cranial motor nuclei and spinal motor columns (shown here at E18.5).

Figure 32B:
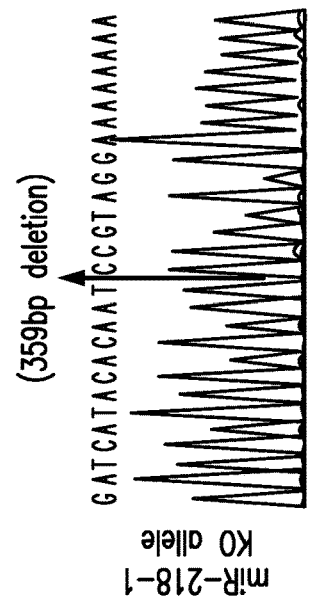
Figure 32A:
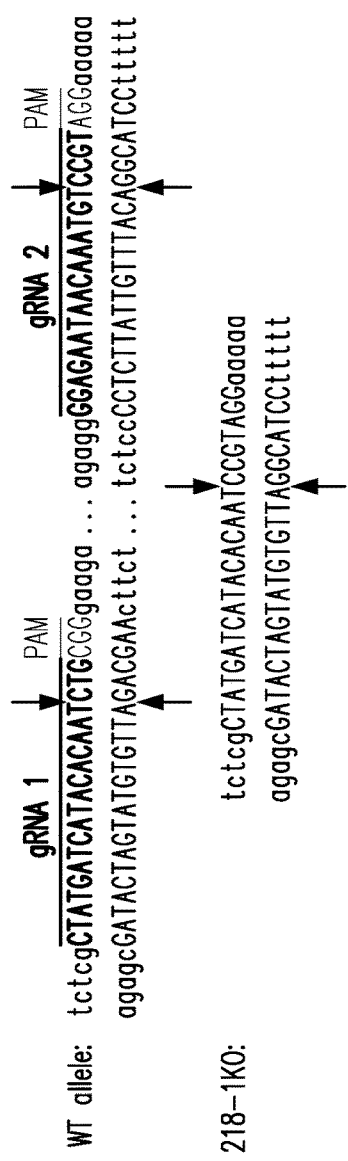
Figure 32D:
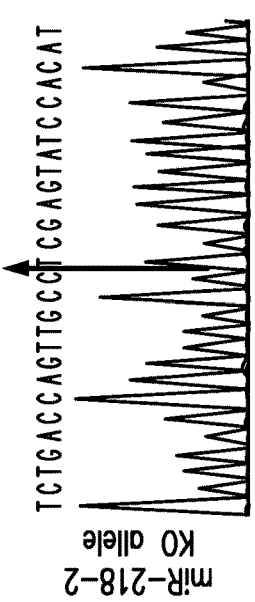
Figure 32C:
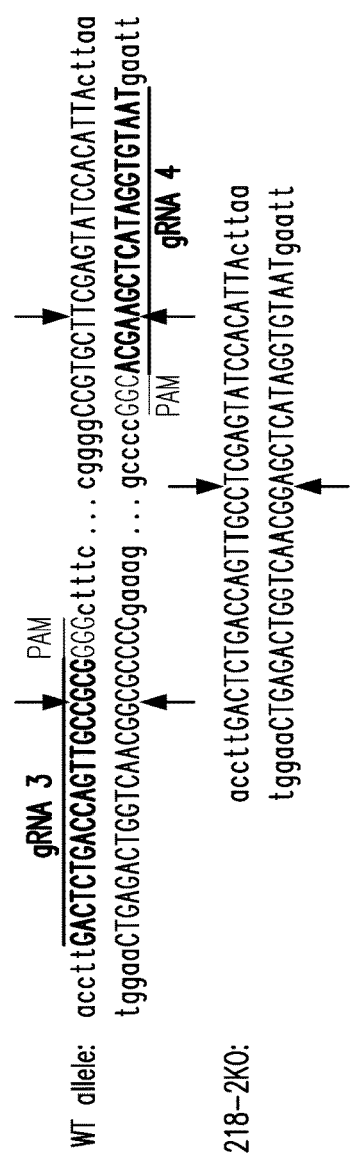
Figures 32E, 32F:
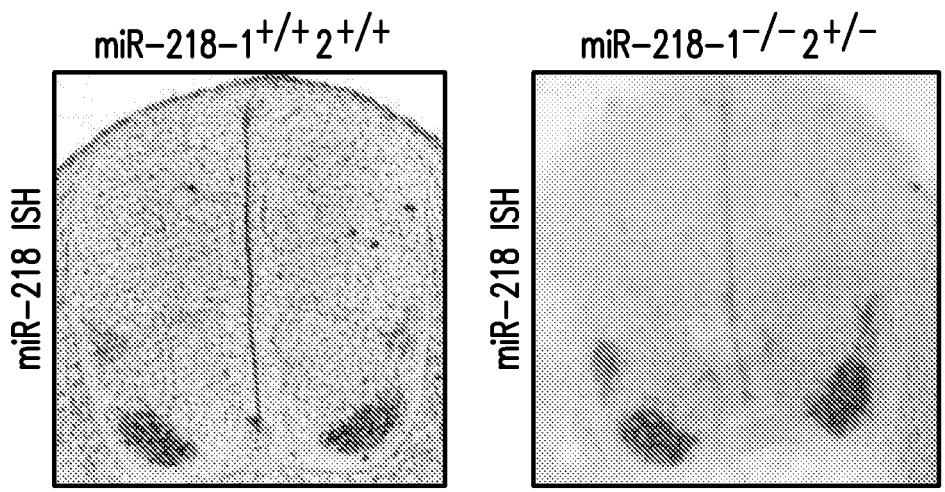
Figures 32G, 32H:
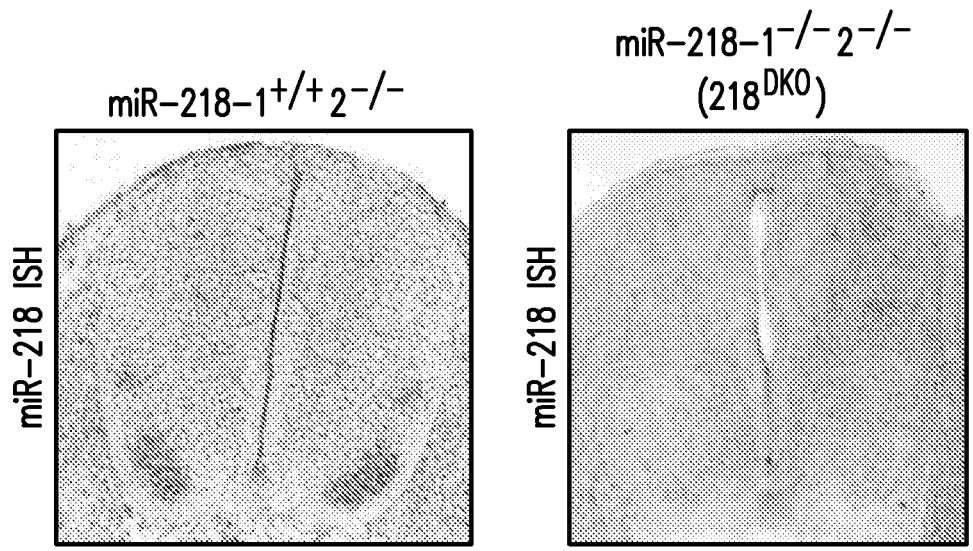

FIG. 32A-H shows CRISPR/Cas9-mediated knockout of miR-218. (A-D) Design and validation of knockout mice. Guide RNA (gRNA) sequences (blue) and PAM sequences (red) used to generate deletions of miR-218-1 (A) and miR-218-2 (C) are highlighted. Induced double stranded break points are indicated with arrows and multiplexed deletions resulted in end joining. FIG. 32A discloses SEQ ID NOS 76-81 and FIG. 32C discloses SEQ ID NOS 83-88, all respectively, in order of appearance. (B, D) CRISPR/Cas9 mediated genomic deletions were screened by PCR and validated by Sanger sequencing. FIG. 32B discloses SEQ ID NO: 82 and FIG. 32D discloses SEQ ID NO: 89. (E-H) In situ hybridization was performed on miR-218 mutants. While deletion of both miR-218-1 alleles and one miR-218-2 allele (F) has little to no effect on signal intensity, deletion of both miR-218-2 alleles (G) results in a clearly identifiable reduction of in situ hybridization signal intensity. (H) However, complete signal loss is only seen when all four miR-218 alleles (218$^{DKO}$) are genetically ablated.

FIG. 33A-I shows Early motoneuron developmental stages are unaffected in 218$^{DKO}$ mutants. (A and B) Representative sections of the thoracic (A) and lumbar (B) spinal cords of control and 218$^{DKO}$ E12.5 embryos stained with transcription factor markers of motoneuron subpopulations. MMC (Lhx+,Hb9+), LMC (Lhx3−,Hb9+), MMCm (Lhx3+, Is11/2-), and MMC1 (Lhx3+,Is11/2+) motoneurons were identified by immunolabelling in 20 um cryosections across cervical, thoracic and lumbar segments. 218$^{DKO}$ motoneuron cell bodies are positioned in the ventrolateral spinal cord indistinguishably from controls. dorsal root ganglion cells outside the spinal cord are Is11/2+(DRG). (C-E) Motoneurons in hemicords were manually counted in cryosections rostrocaudally spaced apart in 320 um intervals across spinal segments. The number of each of these motoneuron subtypes is unaffected in 218$^{DKO}$ embryos (n=4 and 3 animals, standard deviation is shown). (F) Average numbers of motoneurons of each identified subtype in 20 um cryosections of control and 218$^{DKO}$ hemi-spinal cords No significant change in motoneuron numbers is noted across each of these spinal cord regions at E12.5. (G) Hb9::gfp control and $218^{DKO}$ E12.5 embryos were glycerol cleared and flat mounted to observe motor axon projection patterns. However, no differences in motor outgrowth or patterning could be observed at E12.5. (H and I) $218^{DKO}$ mice do not exhibit neuronal defects associated with Slit2 and Slit3 ablation. Projection of the ophthalmic nerve (H, arrow), sensory neuron spinal cord innervation (I, left panels, arrowhead), and commissural axon guidance (I, inset) appear unaffected by the genetic ablation of miR-218.

Figure 27E:
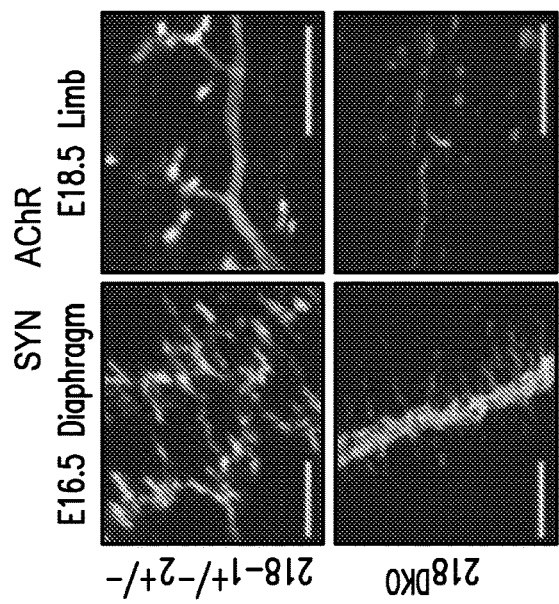
Figure 27D:
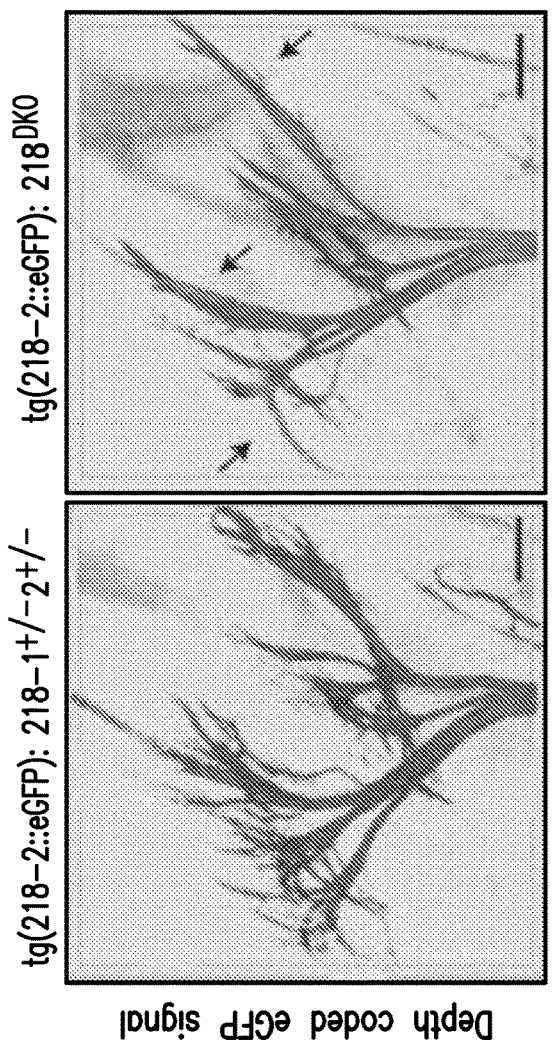
Figure 27F:
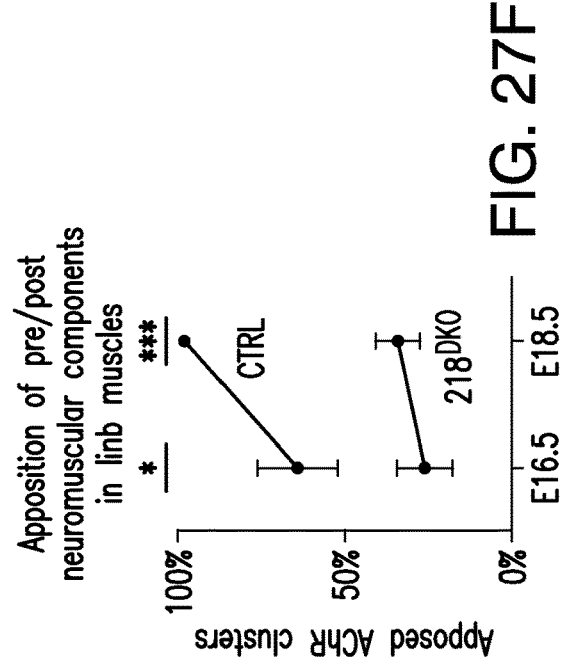
Figures 34A, 34B:
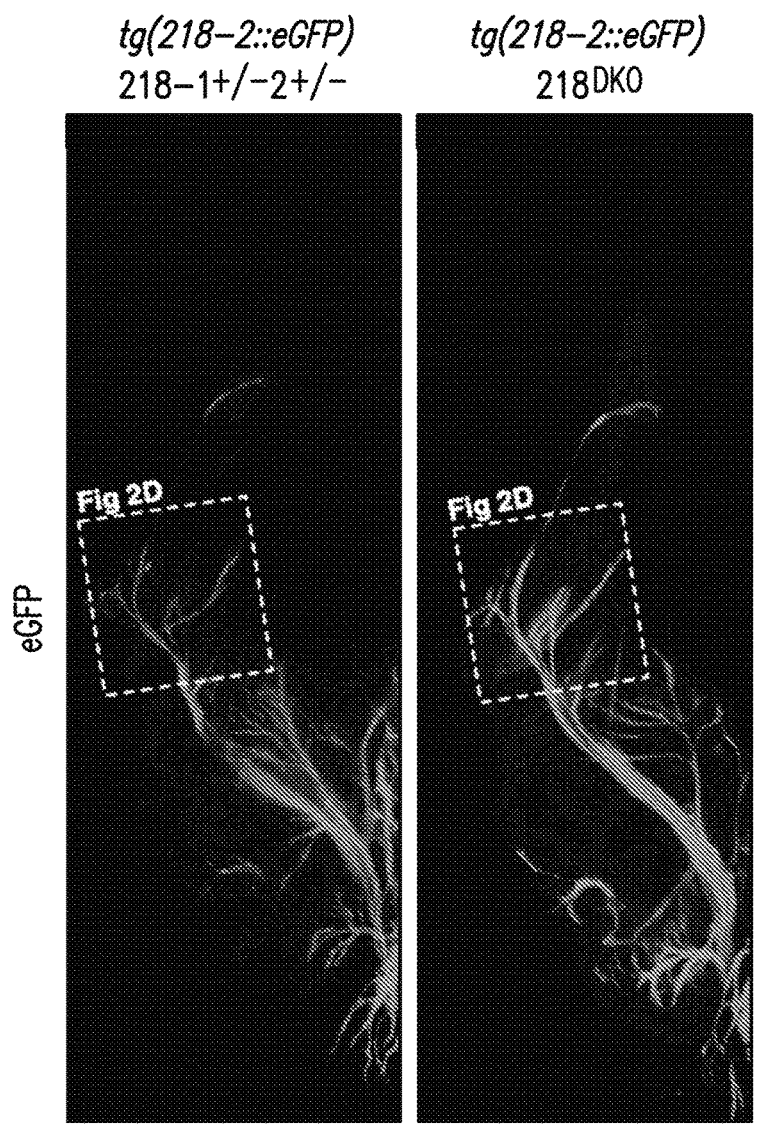

FIG. 34A-B shows 218DKO embryos are not viable and have defective motor axon innervation of muscle. (A) miR-218-1$^{-/-}$2$^{+/-}$ male and female mice were used for generating $218^{DKO}$ embryos. $218^{DKO}$ embryos were observed at Mendelian frequencies at E18.5, though all of these embryos showed no motor responses 20 minutes after cesarean-section. (B) Glycerol cleared lower limbs of tg(218-2:eGFP) E14.5 embryos were deskinned, glycerol cleared, flat-mounted between glass coverslips, and imaged to observe motoneuron branching within muscle. Axon bundle thickness is normal, but complexity of branching is significantly compromised across motor nerves in $218^{DKO}$ embryos. Boxed area denotes area of imaging of the deep peroneal nerve shown in (FIG. 27D).

Figure 35A:
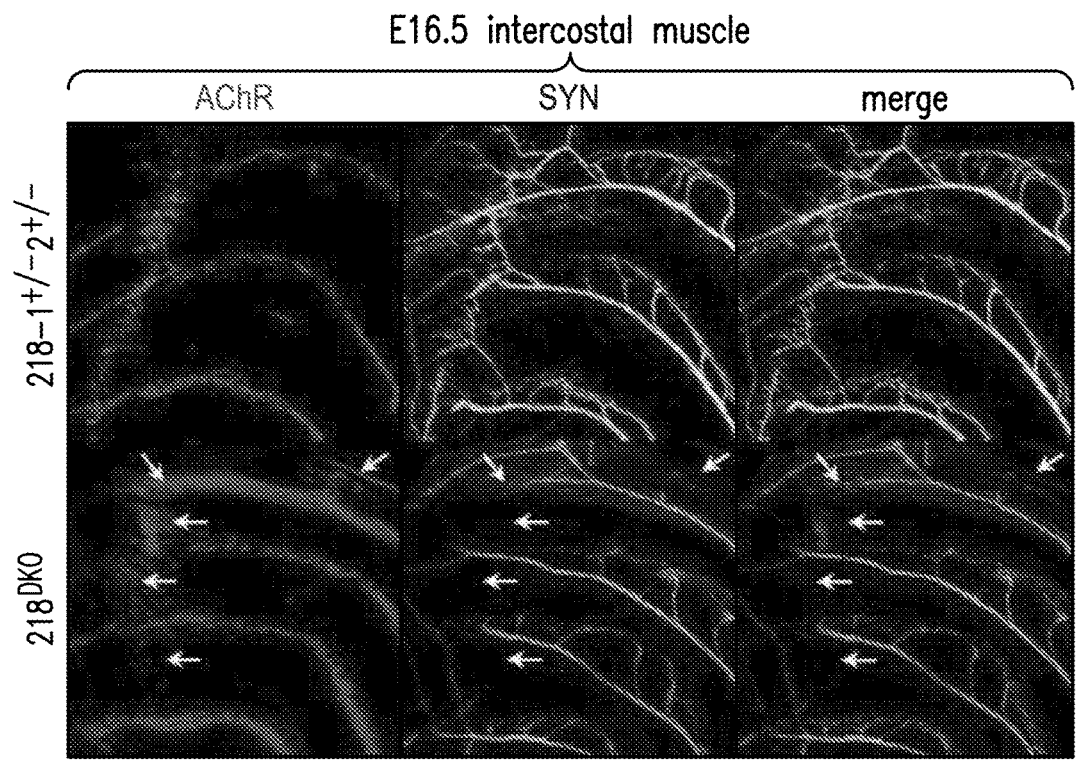
Figure 35B:
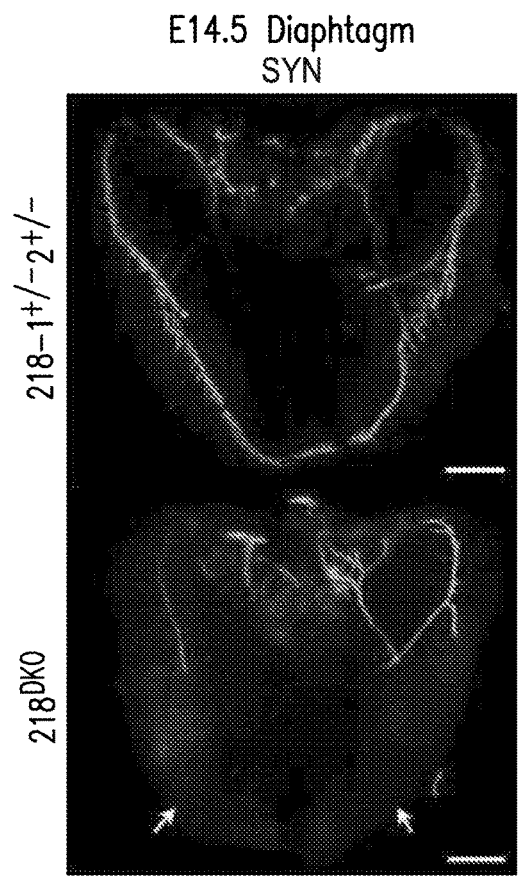
Figure 35C:
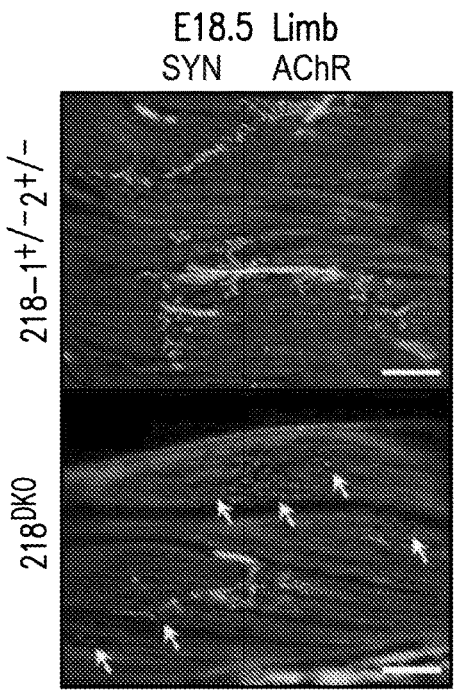

FIG. 35A-C shows neuromuscular junctions are abnormal in $218^{DKO}$ embryos. (A-C) Pre- (SYN+) and post-synaptic (AChR+) neuromuscular junction components were identified by synaptophysin antibody and a-bungarotoxin staining. (A) In E16.5 $218^{DKO}$ intercostal muscles, motor nerves innervate muscle but fail to appropriately induce clustering of post-synaptic AChRs, exhibit less branching, and do not completely innervate the muscle (white arrows) compared with controls. (B) In 14.5 dissected diaphragms, motor axons only partially innervate the circumference of the muscle in mutants, with large areas of the diaphragm (white arrows) lacking motor innervation. (C) A representative section of E18.5 limb tissue demonstrating significant regions of limb AChR clusters (white arrows) lack motor innervation.

Figure 36A:
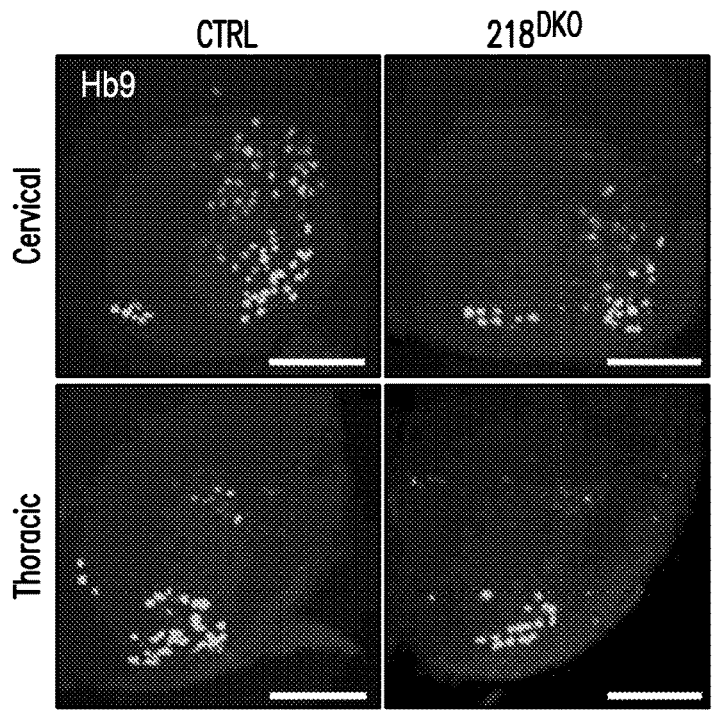
Figure 36B:
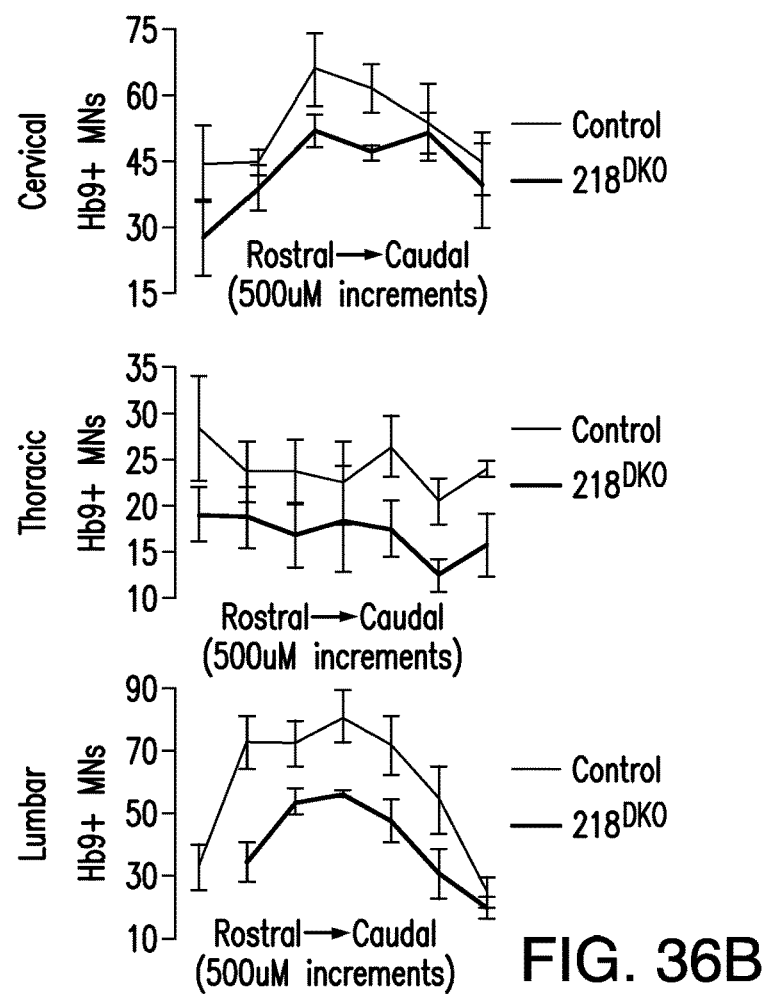

FIG. 36A-B shows reduced numbers of motoneurons in E18.5 $218^{DKO}$ spinal cords. (A) Motoneurons were identified by Hb9 nuclear staining in control and $218^{DKO}$ E18.5 spinal cord sections from lumbar, cervical and thoracic regions at E18.5. Lumbar spinal cord staining is shown in (FIG. 27H). (B) Hb9$^+$ motoneurons in 30 uM cryo sections of hemi-spinal cords were counted in 500 um intervals across the rostrocaudal axis of cervical, thoracic, and lumbar regions. Significant reductions in motoneuron numbers were observed in $218^{DKO}$ spinal cords across all of these regions (n=4, standard deviation is shown).

FIG. 37A-J shows motoneuron electrophysiology. (A) Large LMC α-motoneurons from lumbar spinal cords were identified by Hb9::gfp expression. Fine pulled glass electrodes were patched onto fluorescent cells to record intracellular electrophysiological properties. (B-F) Capacitances, membrane resistances, holding currents (at −70 mV), max firing frequencies, and voltage thresholds were indistinguishable between controls and mutants (n=9, 5). (G) $I_h$ currents were slightly reduced in $218^{DKO}$ motoncurons. (H and I) Current ramps induced firing of $218^{DKO}$ mutant motor neurons with ~3-fold lower currents than required in control motor neurons. (J) Intraspinal motoneuron connectivity was assessed by chemical stimulation of the central pattern generator in an in vitro spinal cord preparation. Recording electrodes were placed on the ventral roots at L2 on ipsilateral and contralateral sides and ipsilaterally on L5. Alternating L/R activity and alternating flexor/extensor activity was observed in both controls and $218^{DKO}$ embryos.

Figures 38A, 38B:
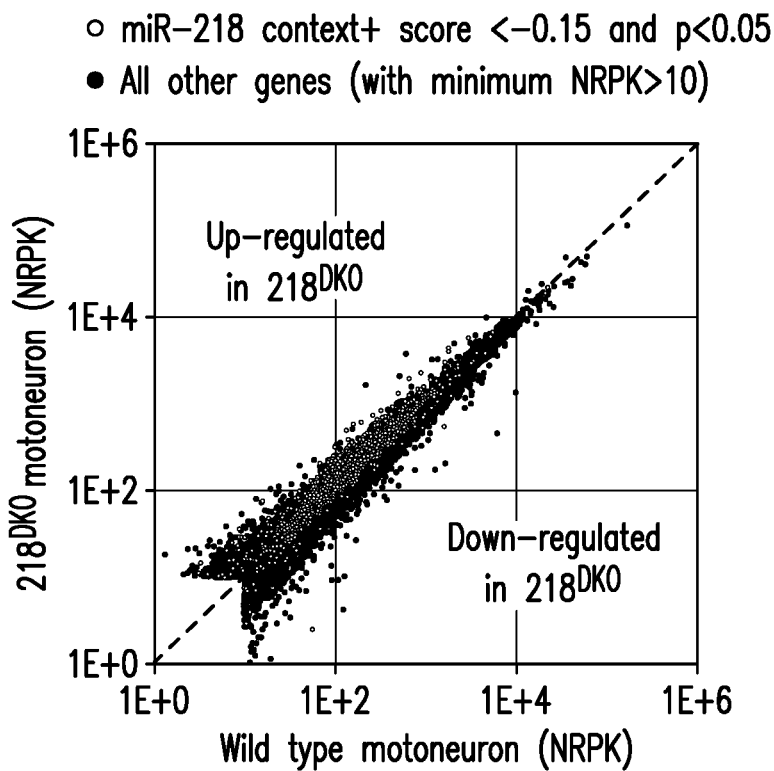
Figure 38C:
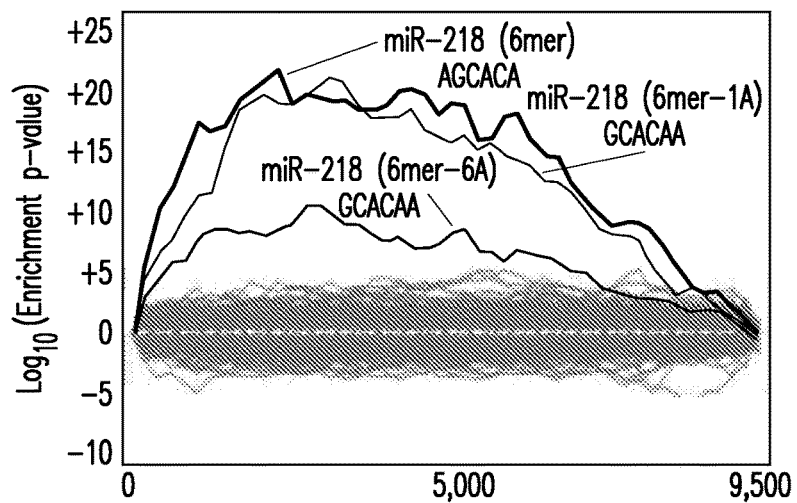
Figure 38D:
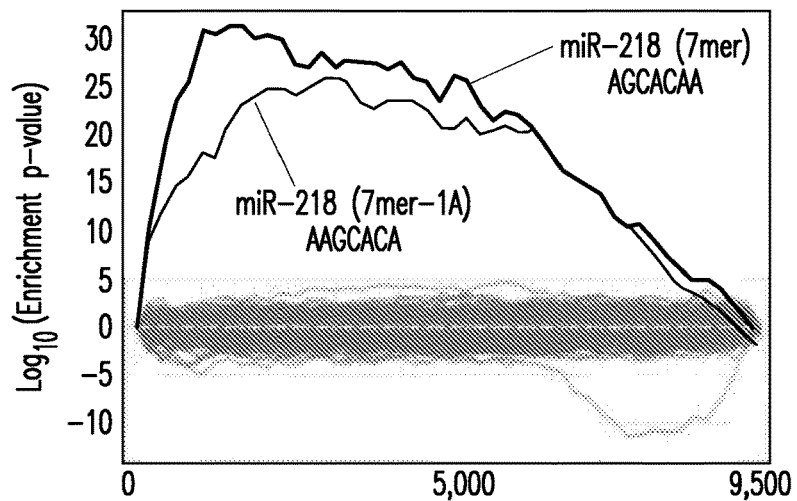
Figure 38E:
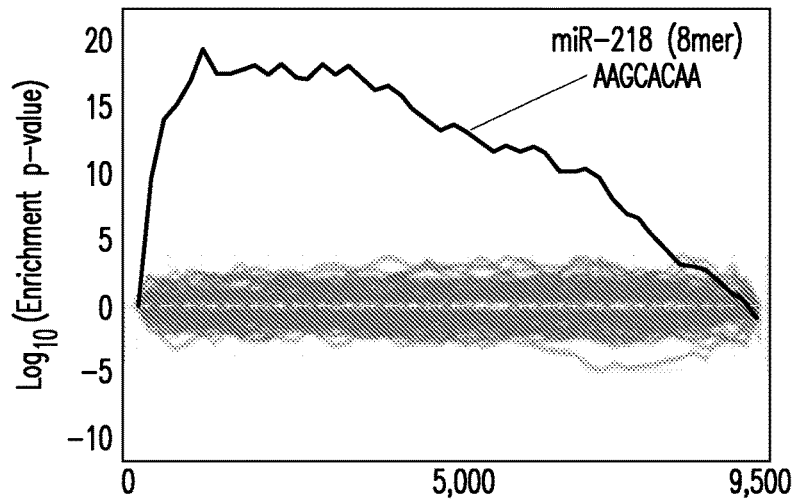

FIG. 38A-G shows altered gene expression of miR-218 target genes in $218_{DKO}$ motoneurons. (A) NRPK gene expression in wild type versus $218^{DKO}$ motoneurons FACS-isolated from E12.5 spinal cords. Genes with robust miR-218 binding sites (context score <−0.15) and that pass statistical significance are in red, and all other genes with NRPK>10 are in gray. (B) The nucleotide sequence of miR-218 and each of its 6mer, 7mer, and 8mer 3'UTR complementary seed matches is shown. FIG. 38B discloses SEQ ID NOS 60-61 and 68-73, respectively, in order of appearance. (C-E) Transcripts were ranked from upregulated to downregulated in $218^{DKO}$ motoneurons versus wild type motoneurons, and Sylamer was used to determine the statistical enrichment of 6 bp (C), 7 bp (D), and 8 bp (E) 3'UTR miRNA seed matches. Upregulated (de-repressed) genes are specifically and significantly enriched for miR-218 binding sites FIG. 38C discloses "AGCACA" as SEQ ID NO: 71 and "GCACAA" as SEQ ID NO: 72, FIG. 38D discloses "AGCACAA" as SEQ ID NO: 70 and "AAGCACA" as SEQ ID NO: 69 and FIG. 38E discloses "AAGCACAA" as SEQ ID NO: 68. (F) Top ten biological process GO categories enriched in TARGE7$^{218}$ genes as determined by the Gorilla platform. (G) Specific genes within the negative regulation of synaptic transport and neurotransmitter transport categories are listed.

Figure 39C:
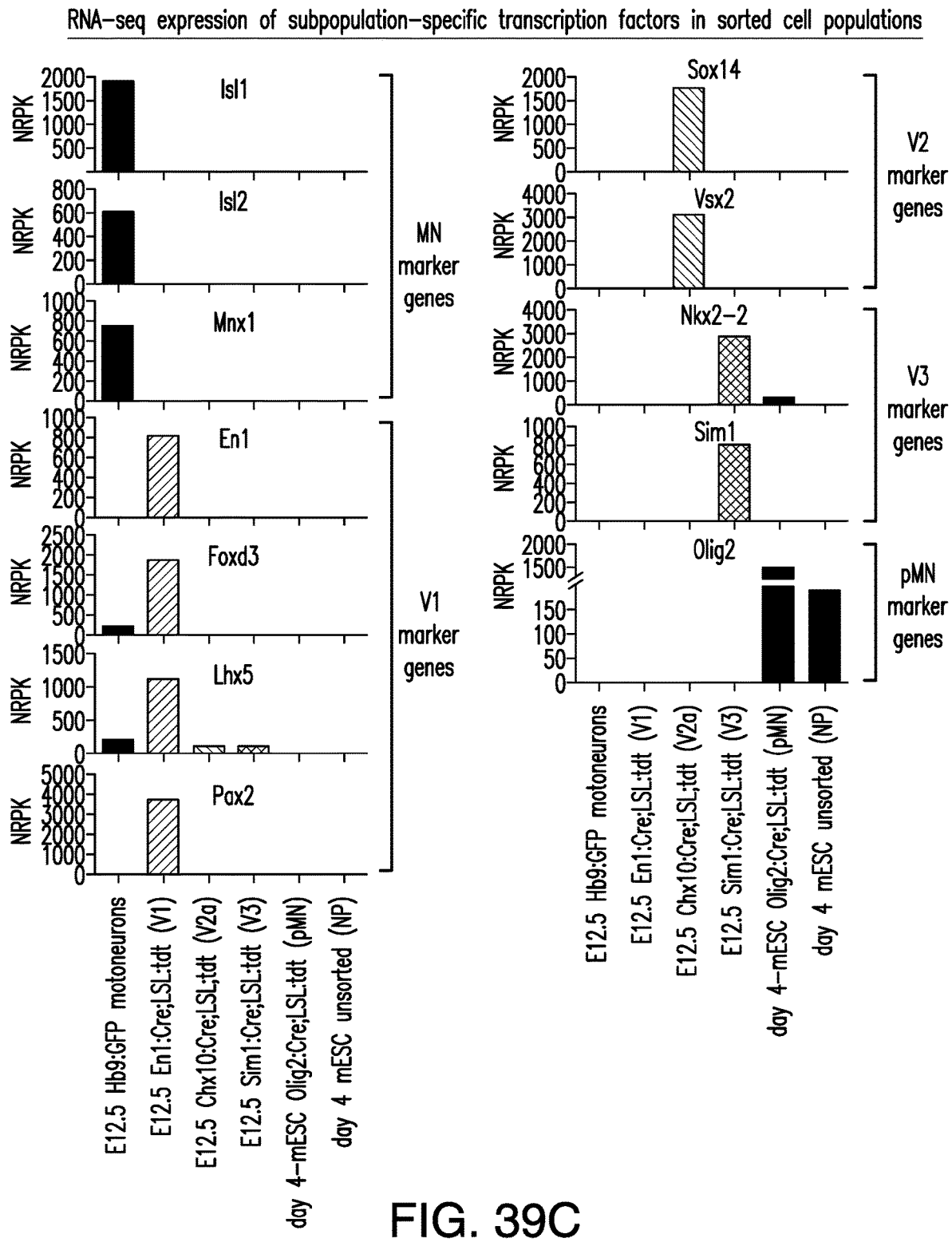

FIG. 39A-C shows FACS-isolated subpopulations specifically express known marker genes. (A) V1, V2a, V3 interneurons, and motoneurons were genetically labelled in E12.5 spinal cords using the reported mouse lines and motoneuron progenitors were isolated from mES-derived transgenic neuronal progenitors by either FACS (pMN) or collecting whole neuro spheres at day 4 of differentiation. (B) Representative FACS plots demonstrate clear separation of fluorescently labelled cell populations. (C) Normalized reads per kilobase (NRPK) for known cellular marker genes are plotted for each dataset to validate the purity of cells. Each known marker gene is specifically and abundantly expressed in the respective dataset. Importantly, Olig2$^+$ progenitors were captured before motoneurogenesis, as indicated by the expression of Olig2 but absence of Hb9, Is11, and Is12 expression.

FIG. 40 shows the TARGET$^{218}$ described by Example 2.

FIG. 41 shows primer and sequence information for the primers described by Example 2. FIG. 41 discloses the first forward and reverse primers as SEQ ID NOS 90-91, the gRNA target sequences as SEQ ID NOS 92-97, the oligos for px330 vector as SEQ ID NOS 98-109, the T7 primers as SEQ ID NOS 110, 116, 111, 116, 112, 116, 113, 116, 114, 116 and 115-116 and the last forward and reverse primers as SEQ ID NOS 117-120, all respectively, in order of appearance.

Figure 42:
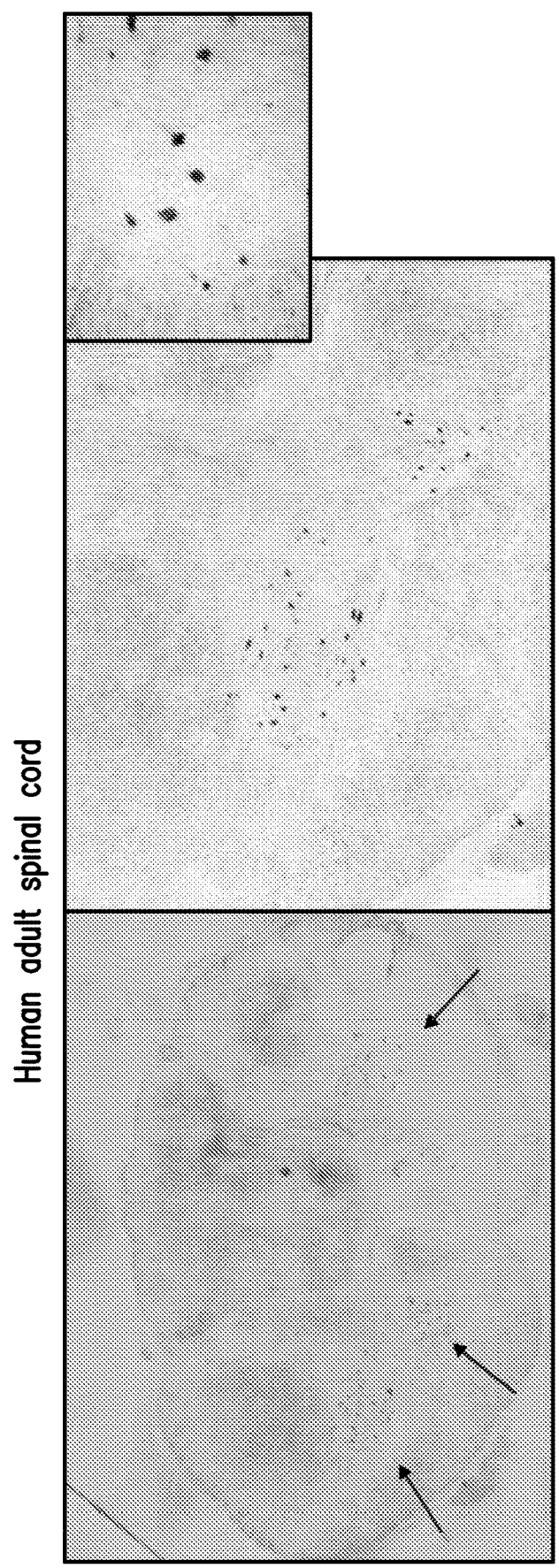

FIG. 42 shows that MicroRNA-218 (miR-218) expression is detected by in situ hybridization in adult human spinal cords from neurologically healthy controls. miR-218 specifically identifies motoneurons.

5. DETAILED DESCRIPTION OF THE INVENTION

The present disclosure relates to methods and compositions for treating and/or reducing the severity of a motor neuron disease. For purposes of clarity and not by way of limitation, the detailed description of the invention is divided into the following subsections:
 (i) motor neuron-specific promoters;
 (ii) therapeutic nucleic acids operably linked to a motor neuron-specific promoter;

(iii) therapeutic compositions;
(iv) pharmaceutical compositions;
(v) methods of use; and
(vi) kits.

The following are terms relevant to the present invention:

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

An "effective amount" of a substance as that term is used herein is that amount sufficient to effect beneficial or desired results, including clinical results, and, as such, an "effective amount" depends upon the context in which it is being applied. In the context of administering a composition to treat and/or reduce the severity of a motor neuron disease in a subject, an effective amount of a composition described herein is an amount sufficient to treat and/or ameliorate a motor neuron disease, as well as decrease the severity and/or reduce the likelihood of a motor neuron disease. The decrease can be a 10%, 20%, 30%, 40%, 50%, 60%, 70%, 80%, 90%, 95%, 98% or 99% decrease in severity of a motor neuron disease, or likelihood of developing a motor neuron disease. An effective amount can be administered in one or more administrations.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more symptoms, diminishment of extent of disease, stabilized (i.e., not worsening) state of disease, prevention of disease, delay or slowing of disease progression, and/or amelioration or palliation of the disease state. The decrease can be a 10%, 20%, 30%, 40%, 50%, 60%, 70%, 80%, 90%, 95%, 98% or 99% decrease in severity of complications or symptoms. "Treatment" can also mean prolonging survival as compared to expected survival if not receiving treatment.

The term "expression vector" is used to denote a nucleic acid molecule that is either linear or circular, into which another nucleic acid sequence fragment of appropriate size can be integrated. Such nucleic acid fragment(s) can include additional segments that provide for transcription of a gene encoded by the nucleic acid sequence fragment. The additional segments can include and are not limited to: promoters, transcription terminators, enhancers, internal ribosome entry sites, untranslated regions, polyadenylation signals, selectable markers, origins of replication and such, as known in the art. Expression vectors are often derived from plasmids, cosmids, viral vectors and yeast artificial chromosomes; vectors are often recombinant molecules containing nucleic acid sequences from several sources.

The term "operably linked," when applied to nucleic acid sequences, for example in an expression vector, indicates that the sequences are arranged so that they function cooperatively in order to achieve their intended purposes, i.e., a promoter sequence allows for initiation of transcription that proceeds through a linked coding sequence as far as the termination signal.

A "nucleic acid molecule" is a single or double stranded covalently-linked sequence of nucleotides in which the 3' and 5' ends on each nucleotide are joined by phosphodiester bonds and/or non-phosphodiester bonds. In certain embodiments, the polynucleotide can be made up of deoxyribonucleotide bases, ribonucleotide bases or a combination of deoxyribonucleotide and ribonucleotide bases (for example a RNA:DNA backbone hybrid). In certain embodiments, the polynucleotide can include other chemical moieties in addition to or in place of the deoxyribonucleotide and/or ribonucleotide bases. Polynucleotides include DNA and RNA, and can be manufactured synthetically in vitro or isolated from natural sources.

The term "promoter" as used herein denotes a region within a gene to which transcription factors and/or RNA polymerase can bind so as to control expression of an associated coding sequence. Promoters are commonly, but not always, located in the 5' non-coding regions of genes, upstream of the translation initiation codon. The promoter region of a gene can include one or more consensus sequences that act as recognizable binding sites for sequence specific nucleic acid binding domains of nucleic acid binding proteins. Nevertheless, such binding sites can also be located in regions outside of the promoter, for example in enhancer regions located in introns or downstream of the coding sequence.

A "regulatory gene" is a gene involved in controlling the expression of one or more other genes.

5.1 Motor Neuron-Specific Promoters

The present disclosure provides for motor neuron-specific promoter nucleic acid sequences. In certain non-limiting embodiments the promoter specifically expresses a nucleic acid or gene operatively linked to the promoter in motor neurons. Thus, when said promoter, operatively linked to a gene in, for example, an expression vector, is injected or otherwise administered into a subject, the gene is expressed in motor neurons at much higher levels than it is expressed in other cells or tissues, such as, for example, liver, kidney, lung, or muscle.

In certain non-limiting embodiments, the promoter comprises the nucleic acid sequence:

(SEQ ID NO: 1)

```
taaacgcccc aatttgctac ttatcaaata gtatacattt ttggctcaga aaaaaacctg   60
atgtctgtat attacttctc aactaaaatc cctcagtcct taactggcat gtgtattagt  120
caaggcatct ttgagaaggg cattatttcc ctacacttag gatgggggaaa gagaaattaa  180 aaaggaatcc taaaataggt gcatttaatt ctccccaatt taaatgtaag tggtgcgtct  240
tttaggcaat aatgatatgc cttttagtcc tccattacaa acacttccat cgatgaattt  300
ccttaatgtt gatgatggtt agtgcagttt gagggaatct gtatttattc agaaaatgtt  360
cccatagaat gacctaccag atgggccacg taacaatgca tggagacatc aaaccaccac  420
```

```
agacatttgg tgettagaat aataaaaaga ctataaaatt agattagttg agtctaattt   480
ggaattggta tattccctac gcaccctcac cgctcttggg cagataaagc cttgagattt   540
agcgctgtgt caaagccaag actgtaactt ccagtaaaag ggagccgagg gaggggggagc  600 ttgctgggag gtcgcggagg gcagagcagt gacctccaat gatttacagg cctttagctt   660
aatgaaattg tttcagtgac atgacagtaa gagctcgtaa tggattggat gccctaatgt   720
aatgaaatta ctccettctg cctaaaaaaa aaaaatgcg caattaatat ttactgagac    780
ctgacagcct ttggtgcgct cgctcgcctg tgtagttccc tcagacagtc agagagaaga   840
gacagagcag cgtggcagac aggcgggctc tgcaggagct cctggcaggg acaagcagag   900 cctgcaag.                                                           908
```

(SEQ ID NO:1).

In a certain non-limiting embodiment, the promoter comprises the nucleic acid sequence of SEQ ID NO:1, or a nucleic acid having a sequence that is at least 60, 65, 70, 75, 80, 85, 90, 95, or at least 99 percent homologous thereto (where homology may be determined using standard software such as BLAST or FASTA).

In certain non-limiting embodiments, the promoter comprises a nucleic acid of SEQ ID NO:1 in which 1, 2, 3, 4, 5 or more nucleotides are either deleted, substituted by another nucleotide, or in which 1, 2, 3, 4, 5 or more nucleotides are added. In other embodiments, the nucleic acid of SEQ ID NO:1 comprises a conservative nucleotide substitution such that the promoter maintains its ability to express a nucleic acid operably linked to the promoter in motor neurons.

In certain non-limiting embodiments, the promoter comprises a nucleic acid of SEQ ID NO:1, or a fragment thereof, wherein the length of the nucleic acid is 10 kilobases (kb) or less, 9.5 kb or less, 9 kb or less, 8.5 kb or less, 8 kb or less, 7.5 kb or less, 7 kb or less, 6.5 kb or less, 6 kb or less, 5.5 kb or less, 5 kb or less, 4.5 kb or less, 4 kb or less, 3.5 kb or less, 3 kb or less, 2.5 kb or less, 2 kb or less, 1.5 kb or less, 1 kb or less, 500 base pairs (bp) or less, 400 bp or less, 300 bp or less, 200 bp or less, 100 bp or less, 50 bp or less, or 20 bp or less.

In certain non-limiting embodiments, the promoter comprises a nucleic acid of SEQ ID NO:1, or a fragment thereof, wherein the nucleic acid is not adjacent to another nucleic acid sequence present in an endogenous miR-218 promoter, or an endogenous Slit2 or Slit3 promoter. In certain embodiments, said nucleic acid sequence of the endogenous miR-218, Slit2 or Slit3 promoter is a nucleic acid having a length of 1, 2, 3, 4, 5, 6, 7, 8, 9, 10, 11, 12, 13, 14, 15, 16, 17, 18, 19, 20 or more nucleotide base pairs.

In certain embodiments, the miR-218 is a mouse miR-218 described by GenBank Accession No. NR 029798 or NR 029799, or a nucleic acid having a sequence that is at least 60, 65, 70, 75, 80, 85, 90, 95, or at least 99 percent homologous thereto (where homology may be determined using standard software such as BLAST or FASTA).

In certain embodiments, the miR-218 is a human miR-218 described by GenBank Accession No. NR_029632 or NR_029631, or a nucleic acid having a sequence that is at least 60, 65, 70, 75, 80, 85, 90, 95, or at least 99 percent homologous thereto (where homology may be determined using standard software such as BLAST or FASTA).

In certain embodiments, the Slit2 is a mouse Slit2 described by GenBank Accession No. NM_001291227, NM_001291228, NM_178804, NR_111900, or NC_000071, or a nucleic acid having a sequence that is at least 60, 65, 70, 75, 80, 85, 90, 95, or at least 99 percent homologous thereto (where homology may be determined using standard software such as BLAST or FASTA).

In certain embodiments, the Slit2 is a human Slit2 described by GenBank Accession No. NM_001289135, NM_001289136, NM_004787, or NC_000004, or a nucleic acid having a sequence that is at least 60, 65, 70, 75, 80, 85, 90, 95, or at least 99 percent homologous thereto (where homology may be determined using standard software such as BLAST or FASTA).

In certain embodiments, the Slit3 is a mouse Slit3 described by GenBank Accession No. NM_011412 or NC_000077, or a nucleic acid having a sequence that is at least 60, 65, 70, 75, 80, 85, 90, 95, or at least 99 percent homologous thereto (where homology may be determined using standard software such as BLAST or PASTA).

In certain embodiments, the Slit3 is a human Slit3 described by GenBank Accession No. NM_001271946, NM_003062, NG_033081, or NC_000005, or a nucleic acid having a sequence that is at least 60, 65, 70, 75, 80, 85, 90, 95, or at least 99 percent homologous thereto (where homology may be determined using standard software such as BLAST or PASTA).

In certain non-limiting embodiments, the promoter comprises one or more nucleic acid sequence, or fragment thereof, described in Table 1.

TABLE 1

| Nucleic acid promoter sequences |
|---|
| taaacgcccc aatttgctac (SEQ ID NO: 2) |
| ttatcaaata gtatacattt (SEQ ID NO: 3) |
| ttggctcaga aaaaaacctg (SEQ ID NO: 4) |
| atgtctgtat attacttctc (SEQ ID NO: 5) |
| aactaaaatc cctcagtcct (SEQ ID NO: 6) |
| taactggcat gtgtattagt (SEQ ID NO: 7) |
| caaggcatct ttgagaaggg (SEQ ID NO: 8) |
| cattatttcc ctacacttag (SEQ ID NO: 9) |
| gatggggaaa gagaaattaa (SEQ ID NO: 10) |
| aaaggaatcc taaaataggt (SEQ ID NO: 11) |
| gcatttaatt ctccccaat (SEQ ID NO: 12) |

TABLE 1-continued

Nucleic acid promoter sequences

```
taaatgtaag tggtgcgtct (SEQ ID NO: 13)

tttaggcaat aatgatatgc (SEQ ID NO: 14)

cttttagtcc tccattacaa (SEQ ID NO: 15)

acacttccat cgatgaattt (SEQ ID NO: 16)

ccttaatgtt gatgatggtt (SEQ ID NO: 17)

agtgcagttt gagggaatct (SEQ ID NO: 18)

gtatttattc agaaaatgtt (SEQ ID NO: 19)

cccatagaat gacctaccag (SEQ ID NO: 20)

atgggccacg taacaatgca (SEQ ID NO: 21)

tggagacatc aaaccaccac (SEQ ID NO: 22)

agacatttgg tgcttagaat (SEQ ID NO: 23)

aataaaaaga ctataaaatt (SEQ ID NO: 24)

agattagttg agtctaattt (SEQ ID NO: 25)

ggaattggta tattccctac (SEQ ID NO: 26)

gcaccctcac cgctcttggg (SEQ ID NO: 27)

cagataaagc cttgagattt (SEQ ID NO: 28)

agcgctgtgt caaagccaag (SEQ ID NO: 29)

actgtaactt ccagtaaaag (SEQ ID NO: 30)

ggagccgagg gaggggagc (SEQ ID NO: 31)

ttgctgggag gtcgcggagg (SEQ ID NO: 32)

gcagagcagt gacctccaat (SEQ ID NO: 33)

gatttacagg cctttagctt (SEQ ID NO: 34)

aatgaaattg tttcagtgac (SEQ ID NO: 35)

atgacagtaa gagctcgtaa (SEQ ID NO: 36)

tggattggat gccctaatgt (SEQ ID NO: 37)

aatgaaatta ctcccttctg (SEQ ID NO: 38)

cctaaaaaaa aaaaaatgcg (SEQ ID NO: 39)

caattaatat ttactgagac (SEQ ID NO: 40)

ctgacagcct ttggtgcgct (SEQ ID NO: 41)

cgctcgcctg tgtagttccc (SEQ ID NO: 42)

tcagacagtc agagagaaga (SEQ ID NO: 43)

gacagagcag cgtggcagac (SEQ ID NO: 44)

aggcgggctc tgcaggagct (SEQ ID NO: 45)

cctggcaggg acaagcagag (SEQ ID NO: 46)

cctgcaag (SEQ ID NO: 47)
```

In one embodiment, the promoter specifically expresses an operatively linked nucleic acid or gene in a brainstem and/or spinal motor neuron. Such motor neurons include, for example, motor neurons having an axon that exits the central nervous system.

In certain embodiments, the motor neuron is a sympathetic and/or parasympathetic motor neuron.

In other embodiments, the promoter specifically expresses the operatively linked nucleic acid or gene in a cranial motor neuron.

In certain embodiments, the motor neuron is a lower motor neuron, for example, an efferent neuron that innervates a muscle.

In certain embodiments, the motor neuron is a somatic motor neuron that innervates skeletal muscle, for example, muscles of the limbs, abdomen, and intercostal muscles.

In other embodiments, the motor neuron is a visceral motor neuron, for example, motor neurons that innervate the branchial muscles of the head and neck, or motor neurons that innervate cardiac muscle and smooth muscles of the viscera, or that synapse onto neurons of the autonomic nervous system.

In certain embodiments, compositions disclosed herein include a promoter nucleic acid sequence, wherein said nucleic acid sequence is part of an expression vector, wherein the expression vector further comprises a second nucleic acid that is expressed in a host cell, for example in a motor neuron cell.

In certain embodiments, the compositions described herein are administered to treat or prevent a motor neuron disease, by way of gene therapy. Gene therapy refers to therapy performed by the administration to a subject of an expressed or expressible nucleic acid.

Any of the methods for gene therapy available in the art can be used according to the present disclosure. Exemplary methods are described below. For general reviews of the methods of gene therapy, see Kron and Kreppel. Curr Gene Ther 12(5):362-73 (2012); Yi et al. Curr Gene Ther 11(3): 218-28 (2011); Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); Morgan and Anderson, Ann. Rev. Biochem. 62:191-217 (1993); and May, TIBTECH 11(5):155-215 (1993). Methods commonly known in the art of recombinant DNA technology which can be used are described in Ausubel et al. (eds.), Current Protocols in Molecular Biology, John Wiley & Sons, N Y (1993); and Kriegler, Gene Transfer and Expression, A Laboratory Manual, Stockton Press, NY (1990).

Delivery of nucleic acid into a subject or cell, e.g., in an in vitro cell culture, can be either direct, in which case the subject or cell is directly exposed to the nucleic acid or nucleic acid-carrying vectors, or indirect, in which case cells are first transformed with the nucleic acids in vitro, then transplanted into the subject.

In certain embodiments, the nucleic acid may be directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retroviral or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, *J. Biol. Chem.* (1987); 262:4429-4432).

The nucleic acid-ligand complexes can also be formed in which the ligand includes a fusogenic viral peptide to disrupt endosomes, allowing the nucleic acid to avoid lysosomal degradation. In addition, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA (1989); 86:8932-8935; Zijlstra et al., Nature (1989); 342:435-438).

In certain embodiments, a viral vector that contains a promoter nucleic acid described herein operatively linked to an expressible nucleic acid or gene can be used. For example, a retroviral vector can be used (see Miller et al., Meth. Enzymol. (1993); 217:581-599). These retroviral vectors contain the components necessary for the correct packaging of the viral genome and integration into the host cell DNA. More detail about retroviral vectors can be found in Boesen et al., Biotherapy (1994); 6:291-302. Other references illustrating the use of retroviral vectors in gene therapy are: Anson, Genet Vaccines Ther 13; 2(1):9 (2004); Clowes et al., J. Clin. Invest. (1994); 93:644-651; Kiem et al., Blood (1994); 83:1467-1473; Salmons and Gunzberg, Human Gene Therapy (1993); 4:129-141; and Grossman and Wilson, Curr. Opin. in Genetics and Devel. (1993); 3:110-114.

In certain embodiments, the vehicle for delivering the nucleic acids of the present disclosure is an adenovirus. Adenoviruses have the advantage of being capable of infecting non-dividing cells. Kron and Kreppel, Curr Gene Ther 12(5):362-73 (2012) and Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995).

In certain embodiments, an adeno-associated virus (AAV) can be used (Zhong et al. J Genet Syndr Gene Ther. 2012 Jan. 10; S1. pii: 008; High, KA, Blood, 120(23):4482-7 (2012): Walsh et al., Proc. Soc. Exp. Biol. Med. 204:289-300 (1993); U.S. Pat. No. 5,436,146). In certain embodiments, AAV vectors are used. Vectors that can be used in gene therapy are discussed in detail below.

Recombinant cells can also be used in the methods of treatment described herein, where nucleic acid sequences encoding a promoter nucleic acid operatively linked to an expressible nucleic acid or gene, are introduced into the cells such that they are expressible by the cells or their progeny, and the recombinant cells are then administered in vivo for therapeutic effect.

In certain non-limiting examples, the methods of the present invention involve transferring a nucleic acid of the present disclosure, for example an expression vector comprising a promoter sequence as described herein and one or more expressible nucleic acids, to a host cell in a cell culture by methods such as transfection, electroporation, microinjection, infection with a viral or bacteriophage vector containing the nucleic acid sequences, lipofection, calcium phosphate mediated transfection, cell fusion, chromosome-mediated gene transfer, microcell-mediated gene transfer, spheroplast fusion, etc. Usually, the method of transfer includes the transfer of a selectable marker to the host cells. The cells are then placed under selection to isolate those host cells that have taken up and are expressing the transferred gene. Those host cells are then delivered to a patient. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985)), and can be used in accordance with the present disclosure, provided that the necessary developmental and physiological functions of the recipient cells are not disrupted.

In certain embodiments, the nucleic acid can be introduced into motor neuron cells and/or motor neuron stem or progenitor cells, and/or embryonic stem cells (ESCs), and/or induced pluripotent stem cells (iPSCs), prior to administration in vivo of the resulting recombinant cell by any method known in the art. Any stem and/or progenitor cells which can be isolated and maintained in vitro can be used (see e.g. PCT Publication WO 94/08598; Porada and Porada, J. Genet Syndr Gene Ther. May 25; S1, p11:011 (2012); Stemple and Anderson, Cell 71:973-985 (1992); Rheinwald, Meth. Cell Bio. 21A:229 (1980); and Pittelkow and Scott, Mayo Clinic Proc. 61:771 (1986)).

The resulting recombinant cells can be delivered to a patient by various methods known in the art. The amount of cells envisioned for use depends on the desired effect, patient state, etc., and can be determined by one skilled in the art.

In certain embodiments, the terms "vector" and "expression vector" mean the vehicle by which a nucleic acid such as a DNA or RNA sequence (e.g., a foreign gene) can be introduced into a host cell, so as to transform the host and promote expression (e.g., transcription and translation) of the introduced sequence. Vectors include plasmids, phages, viruses, etc.; they are discussed in greater detail below. A "therapeutic vector" as used herein refers to a vector which is acceptable for administration to an animal, and particularly to a human.

Vectors typically include the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA can be from the same or different organisms. In certain embodiments the promoter comprises a nucleic acid comprising a sequence of SEQ ID NO:1 as described herein, wherein the promoter is included on an expression vector with an expressible nucleic acid or gene, wherein the expressible nucleic acid or gene is specifically expressed in a motor neuron cell.

A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET plasmids (Invitrogen, San Diego, Calif.), pCDNA3 plasmids (Invitrogen), pREP plasmids (Invitrogen), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

Suitable vectors include viruses, such as adenoviruses, adeno-associated virus (AAV), vaccinia, herpesviruses, baculoviruses, retroviruses, parvovirus, lentivirus, bacteriophages, cosmids, plasmids, fungal vectors, naked DNA, DNA lipid complexes, and other recombination vehicles typically used in the art which have been described for expression in a variety of eukaryotic and prokaryotic hosts, and can be used for gene therapy as well as for simple protein expression.

Viral vectors, especially adenoviral vectors can be complexed with a cationic amphiphile, such as a cationic lipid, polyL-lysine (PLL), and diethylaminoethyldextran (DE-LAE-dextran), which provide increased efficiency of viral infection of target cells (See, e.g., PCT/US97/21496 filed Nov. 20, 1997, incorporated herein by reference). AAV vectors, such as those disclosed in Zhong et al., *J. Genet Syndr Gene Therapy* 2012 Jan. 10; S1, pii: 008, U.S. Pat. Nos. 5,139,941, 5,252,479 and 5,753,500 and PCT publication WO 97/09441, the disclosures of which are incorporated herein, are also useful since these vectors integrate into host chromosomes, with a minimal need for repeat administration of vector. For a review of viral vectors in gene therapy, see McConnell et al., 2004, Hum Gene Ther. 15(11):1022-33; Mccarty et al., 2004, Annu Rev Genet. 38:819-45; Mah et al., 2002, Clin. Pharmacokinet. 41(12): 901-11; Scott et al., 2002, Neuromuscul. Disord. 12(Suppl 1):S23-9.

In certain non-limiting embodiments, the nucleic acids described herein, for example, a motor neuron specific promoter that is operatively liked to a therapeutic nucleic acid, can be integrated into a host cell chromosome or nucleic acid, for example, by using transcription activator-like effector nucleases (TALENs), Zinc-finger nucleases (ZFNs), clustered regularly interspaced short palindromic repeats (CRISPRs, see, e.g., Jinck et al., *Science* (2012); 337:816-821), or transgene expression (e.g., using a natural or chemically modified DNA or RNA).

5.2 Therapeutic Nucleic Acids Operably Linked to a Motor Neuron-Specific Promoter According to the present disclosure, in certain embodiments, the promoter nucleic acids described herein are operably linked with an expressible nucleic acid, such as a gene, wherein the expressible nucleic acid is selectively expressed in a motor neuron. The promoter and expressible nucleic acid can be comprised in an expression vector, as described herein.

The expressible nucleic acid may encode a protein, micro RNA (miRNA), interfering RNA (RNAi) molecule, shRNA molecule, antisense RNA, catalytic RNA, or catalytic DNA. According to an embodiment of the present disclosure, the expressible nucleic acid provides a therapeutic effect when expressed in a motor neuron of a subject diagnosed with or at risk of having a motor neuron disease. In certain non-limiting embodiments, the expressible nucleic acid does not comprise a nucleic acid encoding a miR-218 micro RNA.

In certain embodiments, the expressible nucleic acid comprises DNA. In other embodiments, the expressible nucleic acid comprises RNA.

In certain non-limiting embodiments, the expressible nucleic acid encodes a protein. In certain non-limiting embodiments, the protein is selected from the group consisting of a cytokine, a growth factor, an enzyme, an ion channel, an anti-inflammatory peptide, and an antioxidant.

Non-limiting examples of expressible nucleic acids that can be operatively linked to the promoter nucleic acid sequences described herein include neurotrophic factors such as brain-derived neurotrophic factor (BDNF), glial cell-derived neurotrophic factor (GDNF), and/or neurotrophic factors (NTF) such as neurotrophins.

In certain embodiments, the compositions described herein can be used to replace the function of mutated proteins expressed by a subject. For example, patients with SMA have low levels of Survival of Motor Neuron (SMN) protein. A nucleic acid encoding a functional SMN protein can be operably linked to the promoter nucleic acids described herein such that functional protein is expressed in motor neurons of the subject. Other functional proteins that can be expressed using the compositions described herein include proteins encoded by the genes superoxide dismutase 1 (SOD1); alsin (amyotrophic lateral sclerosis 2 (juvenile); ALS2); amyotrophic lateral sclerosis 4 (ALS4); angiogenin, ribonuclease, RNase A family, 5 (ANG); chromosome 9 open reading frame 72 (C9orf72); FUS RNA binding protein (FUS); senataxin (SETX); TAR DNA binding protein (TAR-DBP); VAMP (vesicle-associated membrane protein)-associated protein B and C (VAPN); dynactin 1 (DCTN1); neurofilament, heavy polypeptide (NEFH); and/or peripherin (PRPH).

In certain embodiments, the nucleic acid operably linked to the promoter nucleic acids described herein can be a regulatory non-coding RNA gene such as a microRNA, for example, miR-218, or a nucleic acid comprising a miR-218 seed sequence, for example, a 6 mer, 7 mer, or 8 mer miR-218 seed sequence selected from the group consisting of 5' UUGUGCUU 3' (SEQ ID NO:48); 5' UGUGCUU 3' (SEQ ID NO:49); 5' UUGUGCU 3' (SEQ ID NO:50); 5' UGUGCU 3' (SEQ ID NO:51); 5' UUGUGC 3' (SEQ ID NO:52); 5' GUGCUU 3' (SEQ ID NO:53); 5' TTGTGCTT 3' (SEQ ID NO:54); 5' TGTGCTT 3' (SEQ ID NO:55); 5' TTGTGCT 3' (SEQ ID NO:56); 5' TGTGCT 3' (SEQ ID NO:57); 5' TTGTGC 3' (SEQ ID NO:58); and 5' GTGCTT 3'(SEQ ID NO:59). In certain embodiments, miR-218 comprises the nucleic acid sequence 5' UUGUGCUUGAUC-UAACCAUGU 3'(SEQ ID NO:60).

In certain embodiments, miR-218 comprises the nucleic acid sequence 5' UUGUGCUUGAUCUAACCAUGUG 3' (SEQ ID NO:61).

In certain embodiments, miR-218 comprises the nucleic acid sequence 5' TTGTGCTTGATCTAACCATGT 3' (SEQ ID NO:62).

In certain embodiments, miR-218 comprises the nucleic acid sequence 5' TTGTGCTTGATCTAACCATGTG 3' (SEQ ID NO:63).

In certain embodiments, miR-218 comprises the nucleic acid sequence 5' GACCAGTCGC TGCGGGGCTT TCCTTTGTGC TTGATCTAAC CATGTGGTGG AAC- GATGGAA ACGGAACATG GTTCTGTCAA GCAC-CGCGGA AAGCACCGTG CTCTCCTGCA 3' (SEQ ID NO:64).

In certain embodiments, miR-218 comprises the nucleic acid sequence 5' GACCAGUCGC UGCGGGGCUU UCCUUUGUGC UUGAUCUAAC CAUGUGGUGG AACGAUGGAA ACGGAACAUG GUUCUGUCAA GCACCGCGGA AAGCACCGUG CUCUCCUGCA 3' (SEQ ID NO:65).

In certain embodiments, miR-218 comprises the nucleic acid sequence 5' GTGATAATGT AGCGAGATTT TCTGT-TGTGC TTGATCTAAC CATGTGGTTG CGAGGTATGA GTAAAACATG GTTCCGTCAA GCACCATGGA ACGT-CACGCA GCTTTCTACA 3'(SEQ ID NO:66).

In certain embodiments, miR-218 comprises the nucleic acid sequence 5' GUGAUAAUGU AGCGAGAUUU UCU-GUUGUGC UUGAUCUAAC CAUGUGGUUG CGAG-GUAUGA GUAAAACAUG GUUCCGUCAA GCAC-CAUGGA ACGUCACGCA GCUUUCUACA 3' (SEQ ID NO:67).

In certain embodiments, miR-218 comprises a sequence that is complimentary to one or more nucleic acid sequences described herein.

In certain embodiments, the expressible nucleic acid operably linked to the promoter nucleic acids described herein encodes a protein that increases miR-218 expression level in motor neurons. In certain embodiments, the expressible nucleic acid encodes a transcription factor protein, such as but not limited to, a transcription factor selected from the group consisting of Isl1, Isl2, Lhx3, Isl-Lhx3 fusion proteins, Phox2a, and a combination thereof.

In certain embodiments, the expressible nucleic acid operably linked to the promoter nucleic acids described herein encodes a compound that inhibits or reduces expression of a miR-218 target nucleic acid. Such a compound can be, for example, an RNAi molecule, shRNA molecule, antisense RNA, catalytic RNA, catalytic DNA, protein, or antibody or fragment thereof, specific for a miR-218 target nucleic acid, or protein encoded therefrom. In certain embodiments, a miR-218 target nucleic acid is a nucleic acid that hybridizes to a miR-218 seed sequence. In certain embodiments, the miR-218 target nucleic acid is selected from the genes described by FIGS. 38 and 40. In certain embodiments, the miR-218 target nucleic acid comprises a nucleic acid sequence selected from the group consisting of 5' AAGCACAA 3' (SEQ ID NO:68); 5' AAGCACA 3' (SEQ ID NO:69); 5' AGCACAA 3' (SEQ ID NO:70); 5' AGCACA 3' (SEQ ID NO:71); 5' GCACAA 3' (SEQ ID NO:72); and 5' AAGCAC 3'(SEQ ID NO:73).

In one set of non-limiting examples, the expressible nucleic acid is an apoptosis inhibitor, such as one of the so-called inhibitors of apoptosis ("IAPs"), for example, the human IAPs c-IAP1, c-IAP2, and XIAP.

In certain non-limiting embodiments, the expressible nucleic acid is a detectable DNA, RNA or protein. Non-limiting examples include fluorescent proteins such as green fluorescent protein (GFP), blue fluorescent protein (EBFP, EBFP2, Azurite, mKalama1), cyan fluorescent protein (ECFP, Cerulean, CyPet, mTurquoise2), and yellow fluorescent protein derivatives (YFP, Citrine, Venus, YPet); β-galactosidase (LacZ); chloramphenicol acetyltransferase (cat); neomycin phosphotransferase (neo); enzymes such as oxidases and peroxidases; antibodies; and/or antigenic molecules.

In certain embodiments, the expressible nucleic acid can be used for analysis of motor neuron viability.

5.3 Therapeutic Compositions

The present disclosure provides for compositions that can increase the activity or level of miR-218 in a cell, for example, a motor neuron. In certain embodiments, the compositions described by the present disclosure can decrease the expression level of a miR-218 target nucleic acid, or the expression level or activity of a protein encoded by a miR-218 target nucleic acid.

In certain embodiments, the composition comprises one or more expressible nucleic acids operably linked to a motor neuron-specific promoter, as described herein.

In certain embodiments, the composition comprises a mir-218 nucleic acid, or a nucleic acid comprising a miR-218 seed sequence, for example, a 6 mer, 7 mer, or 8 mer miR-218 seed sequence selected from the group consisting of 5' UUGUGCUU 3'(SEQ ID NO:48); 5' UGUGCUU 3' (SEQ ID NO:49); 5' UUGUGCU 3' (SEQ ID NO:50); 5' UGUGCU 3' (SEQ ID NO:51); 5' UUGUGC 3' (SEQ ID NO:52); 5' GUGCUU 3' (SEQ ID NO:53); 5' TTGTGCTT 3' (SEQ ID NO:54); 5' TGTGCTT 3' (SEQ ID NO:55); 5' TTGTGCT 3' (SEQ ID NO:56); 5' TGTGCT 3' (SEQ ID NO:57); 5' TTGTGC 3' (SEQ ID NO:58); and 5' GTGCTT 3' (SEQ ID NO:59).

In certain embodiments, the composition comprises a mir-218 nucleic acid comprising the nucleic acid sequence 5' UUGUGCUUGAUCUAACCAUGU 3'(SEQ ID NO:60).

In certain embodiments, the composition comprises a mir-218 nucleic acid comprising the nucleic acid sequence 5' UUGUGCUUGAUCUAACCAUGUG 3'(SEQ ID NO:61).

In certain embodiments, the composition comprises a mir-218 nucleic acid comprising the nucleic acid sequence 5' TTGTGCTTGATCTAACCATGT 3' (SEQ ID NO:62).

In certain embodiments, the composition comprises a mir-218 nucleic acid comprising the nucleic acid sequence 5' TTGTGCTTGATCTAACCATGTG 3' (SEQ ID NO:63).

In certain embodiments, miR-218 comprises the nucleic acid sequence 5' GACCAGTCGC TGCGGGGCTT TCCTTTGTGC TTGATCTAAC CATGTGGTGG AAC-GATGGAA ACGGAACATG GTTCTGTCAA GCAC-CGCGGA AAGCACCGTG CTCTCCTGCA 3' (SEQ ID NO:64).

In certain embodiments, miR-218 comprises the nucleic acid sequence 5' GACCAGUCGC UGCGGGGCUU UCCUUUGUGC UUGAUCUAAC CAUGUGGUGG AACGAUGGAA ACGGAACAUG GUUCUGUCAA GCACCGCGGA AAGCACCGUG CUCUCCUGCA 3' (SEQ ID NO:65).

In certain embodiments, miR-218 comprises the nucleic acid sequence 5' GTGATAATGT AGCGAGATTT TCTGT-TGTGC TTGATCTAAC CATGTGGTTG CGAGGTATGA GTAAAACATG GTTCCGTCAA GCACCATGGA ACGT-CACGCA GCTTTCTACA 3' (SEQ ID NO:66).

In certain embodiments, miR-218 comprises the nucleic acid sequence 5' GUGAUAAUGU AGCGAGAUUU UCU-GUUGUGC UUGAUCUAAC CAUGUGGUUG CGAG-GUAUGA GUA A AACAUG GUUCCGUCAA GCAC-CAUGGA ACGUCACGCA GCUUUCUACA 3'(SEQ ID NO:67).

In certain embodiments, miR-218 comprises a sequence that is complimentary to one or more nucleic acid sequences described herein.

In certain embodiments, the composition comprises a nucleic acid encoding a protein that increases miR-218 expression level in motor neurons, for example, a transcription factor protein, such as but not limited to, a transcription factor selected from the group consisting of Is11, Is12, Lhx3, Is1-Lhx3 fusion proteins, Phox2a, and a combination thereof. In certain embodiments, the nucleic acid is operably linked to a promoter and is constitutively expressed. In certain embodiments, expression of the nucleic acid is inducible or transient.

In certain embodiments, the composition comprises a transcription factor protein selected from the group consisting of Is11, Is12, Lhx3, Is1-Lhx3 fusion proteins, Phox2a, and a combination thereof.

In certain embodiments, the composition can decrease the expression level of a miR-218 target nucleic acid, or the expression level or activity of a protein encoded by a miR-218 target nucleic acid. In certain embodiments, a miR-218 target nucleic acid is a nucleic acid that hybridizes to a miR-218 seed sequence, as described herein. In certain embodiments, the composition comprises an RNAi molecule, shRNA molecule, antisense RNA, catalytic RNA, catalytic DNA, protein, or antibody specific for the miR-218 target nucleic acid, or protein encoded therefrom.

In certain embodiments, the miR-218 target nucleic acid comprises a nucleic acid encoding a gene that is a negative regulator of synaptic transmission or neurotransmitter transport. In certain embodiments, the miR-218 target nucleic acid comprises a nucleic acid encoding a gene that is selected from the genes described by FIGS. 38 and 40. In certain embodiments, the miR-218 target nucleic acid comprises a nucleic acid encoding a gene selected from the group consisting of Slc1a2/GLT-1, Shank2, Grik2, Gnai2, Stxbpl, Park2, Slc6a1, Celf4, Syt13, Stx3, Sv2a, Nrxn3, Slc6a17, and combinations thereof.

In certain embodiments, the composition can be comprised in a vector as described herein.

In certain embodiments, the present disclosure provides for kits comprising one or more of the compositions and/or nucleic acids described herein.

5.4 Pharmaceutical Compositions

In certain embodiments, the present disclosure provides for pharmaceutical compositions comprising the therapeutic compositions and nucleic acids described herein, for example, the motor neuron specific promoter nucleic acids described herein that are operably linked to an expressible nucleic acid. The pharmaceutical compositions can further comprise at least one other agent, such as a stabilizing compound or additional therapeutic agent, and can be administered in any sterile, biocompatible pharmaceutical carrier, including, but not limited to, saline, buffered saline, dextrose, and water. The composition can be in a liquid or lyophilized form and include a diluent (Tris, citrate, acetate or phosphate buffers) having various pH values and ionic strengths, solubilizer such as Tween or Polysorbate, carriers such as human serum albumin or gelatin, preservatives such as thimerosal, parabens, benzylalconium chloride or benzyl alcohol, antioxidants such as ascorbic acid or sodium metabisulfite, and other components such as lysine or glycine. Selection of a particular composition will depend upon a number of factors, including the condition being treated, the route of administration and the pharmacokinetic parameters desired. A more extensive survey of components suitable for pharmaceutical compositions is found in Remington's Pharmaceutical Sciences, 18th ed. A. R. Gennaro, ed. Mack, Easton, Pa. (1980).

In certain embodiments, the methods and compositions of the present disclosure find use in treating a motor neuron disease. The compositions can be administered to the patient intravenously in a pharmaceutically acceptable carrier such as physiological saline. Standard methods for intracellular delivery can be used (e.g., delivery via liposome). Such methods are well known to those of ordinary skill in the art. The formulations of the present disclosure are useful for parenteral administration, such as intravenous, subcutaneous, intramuscular, and intraperitoneal administration. Therapeutic administration of a compound intracellularly can also be accomplished using gene therapy. The route of administration eventually chosen will depend upon a number of factors and can be ascertained by one skilled in the art.

In certain embodiments, the pharmaceutical compositions of the present disclosure can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present disclosure include, in certain embodiments, compositions where the active ingredients are contained in an effective amount to achieve the intended purpose. The amount will vary from one individual to another and will depend upon a number of factors, including the overall physical condition of the patient, e.g., severity and the underlying cause of the motor neuron disease.

In certain embodiments, the formulations of the present disclosure can be administered for prophylactic and/or therapeutic treatments. For example, in alternative embodiments, pharmaceutical compositions of the present disclosure are administered in an amount sufficient to treat, prevent and/or ameliorate a disease, e.g., a motor neuron disease. As is well known in the medical arts, dosages for any one patient depends upon many factors, including stage of the disease or condition, the severity of the disease or condition, the patient's size, body surface area, age, the particular compound to be administered, sex, time and route of administration, general health, and interaction with other drugs being concurrently administered.

Accordingly, in certain embodiments, the compositions described herein can be administered to a patient alone, or in combination with one or more other drugs, nucleotide sequences, lifestyle changes, etc. used in the treatment or prevention of disease, e.g., a motor neuron disease, or symptoms thereof or in pharmaceutical compositions where it is mixed with excipient(s) or other pharmaceutically acceptable carriers.

In certain embodiments, the pharmaceutically acceptable carrier is pharmaceutically inert. In certain embodiments of the present disclosure, the compositions described herein can be administered alone to a subject suffering from a disease, e.g., a motor neuron disease. The dosage regimen also takes into consideration pharmacokinetic parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol.

24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the present disclosure are correct and appropriate.

Single or multiple administrations of formulations can be given depending on the dosage and frequency as required and tolerated by the patient. In certain embodiments, the formulations should provide a sufficient quantity of active agent to effectively treat, prevent or ameliorate the disease to be treated, e.g., a motor neuron disease, or symptoms or complications thereof as described herein.

In certain embodiments, the compositions of the present disclosure are administered once, twice, or three times per day; or once, twice, or three times per week, by intravenous (IV) or subcutaneous (SC) injection to reach a suggested target therapeutic endpoint. Once the target has been achieved, a maintenance dosing schedule is established which will vary depending upon the patient.

5.5 Methods of Use

In certain non-limiting embodiments, the present disclosure provides for a method of treating and/or reducing the severity of a motor neuron disease by administering to a subject in need thereof, a therapeutic composition and/or nucleic acid described herein, for example, the motor neuron specific promoter nucleic acids described herein that are operably linked to an expressible nucleic acid or gene, wherein the expressible nucleic acid or gene is selectively expressed in motor neurons. Accordingly, the present disclosure provides for a method of selectively delivering an expressible nucleic acid to a motor neuron in a subject.

Subjects in need of such treatment or compositions include subjects who have been diagnosed with, or are at risk for developing, a motor neuron disease. In certain embodiments, a motor neuron disease can be any progressive neurological disorder that destroys motor neurons, or disrupts motor neuron function, and thereby disrupt involuntary or voluntary muscle activity such as speaking, walking, breathing, and swallowing. For example, a motor neuron disease is a disorder that disrupts the signaling from nerve cells in the brain (i.e., upper motor neurons) to nerve cells in the brain stem and spinal cord (i.e., lower motor neurons), to muscle tissue.

In certain embodiments, the motor neuron disease is amyotrophic lateral sclerosis (ALS), primary lateral sclerosis (PLS), progressive muscular atrophy, progressive bulbar palsy, pseudobulbar palsy, spinal muscular atrophy (SMA), post-polio syndrome (PPS), spinal and bulbar muscular atrophy (SBMA), Charcot-Marie-Tooth disease (CMT), Guillain-Barre syndrome (GBS), or any other motor neuron disease known in the art.

In certain embodiments, a subject who is at risk for developing a motor neuron disease is a subject who has or had family members diagnosed with a motor neuron disease.

The present disclosure provides for a method of treating a subject suffering from a motor neuron disease, comprising administering, to the subject, an effective amount of a composition comprising a promoter nucleic acid sequence that is operably linked to an expressible nucleic acid or gene, where the expressible nucleic acid or gene inhibits cell death, improves motor neuron cell function, lengthens subject survival, or a combination thereof.

In certain embodiments, an effective amount of a composition described herein is an amount which treats or reduces the severity of a motor neuron disease in a subject. For example, treating or reducing the severity of a motor neuron disease refers to an amelioration in the clinical symptoms or signs of a motor neuron disease, for example, but not by way of limitation, one or more of the following: reduction in the ability to make voluntary movements such as arm and leg movements; speech, swallowing and/or chewing impediments; muscle spasticity, spasms, cramps, and/or fasciculations; breathing impediments; jaw and/or facial muscle weakness; muscle tone loss; and muscle weakness.

5.6 Kits

The presently disclosed subject matter provides for kits for treating a subject diagnosed with, or at risk for having, a motor neuron disease. In certain embodiments, the kit comprises one or more of the compositions or nucleic acids described herein, for example, a nucleic acid of SEQ ID NO:1, and/or a recombinant vector comprising the nucleic acid of SEQ ID NO:1. In certain embodiments, the kit further comprises instructions for administering the compositions or nucleic acids described herein for treating a subject diagnosed with or at risk for having a motor neuron disease.

In certain embodiments, the present disclosure provides for kits comprising one or more of the compositions or nucleic acids described herein in unit dosage form. In certain embodiments, the kit comprises a sterile container which contains the therapeutic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain embodiments, the kit comprises instructions for administering one or more of the compositions or nucleic acids described herein to a subject suffering from, or suspected of having, a motor neuron disease. The instructions can comprise information about the use of the compositions or nucleic acids for treating or preventing a motor neuron disease. In certain embodiments, the instructions comprise at least one of the following: description of the therapeutic agent; dosage schedule and administration for treating or preventing a motor neuron disease or symptoms thereof; precautions; warnings; indications; counter-indications; over dosage information; adverse reactions; animal pharmacology; clinical studies; and/or references. The instructions can be printed directly on the container (when present), or as a label applied to the container, or as a separate sheet, pamphlet, card, or folder supplied in or with the container.

6. EXAMPLES

The presently disclosed subject matter will be better understood by reference to the following Examples, which are provided as exemplary of the invention, and not by way of limitation.

6.1 Example 1: Motor Neuron-Specific Expression of a Recombinant Vector

The present example demonstrates that a 908 base pair nucleic acid sequence from the promoter region of the gene miR-218 is sufficient to specifically express a recombinant green fluorescent transgene in motor neuron cells in vivo. The miR-218 promoter is 7.6 kb and is also known as Pri-miR-218-2:promoter, miR218-promoter, MN-Slit3-promoter, Slit3-promoter, 218-promoter, 218p, and Slit3p.

Methods:

A 908 bp nucleic acid was isolated from the 7.6 kb promoter region of a miR-218 gene that is specifically expressed in mouse motor neurons. The 908 bp nucleic acid is shown in FIG. 1 as SEQ ID NO:1. The 908 bp nucleic acid sequence of SEQ ID NO:1 was operatively linked to eGFP in a recombinant construct (218p:eGFP short). The full length 7.6 kb miR-218 promoter was also operatively linked to eGFP in a recombinant vector (218p:eGFP long).

Transgenic mouse lines were generated for both the 218p:eGFP short and 218p:eGFP long recombinant transgenes. Motor neuron expression levels of GFP in E11.5, E12.5 or E18.5 day mouse embryos were assessed for the transgenic mouse lines. Expression of GFP under the control of a homeobox gene (Hb9) promoter (Hb9:GFP) was used as a control.

A transgenic *Xenopus laevis* was generated using a recombinant transgene comprising the *Xenopus laevis* homolog of the 7.6 kb miR-218 promoter, which was operatively linked to GFP. GFP expression levels in spinal motor neurons of transgenic swimming tadpoles was assessed.

Results:

908 bp Promoter Sequence

Figure 2A:
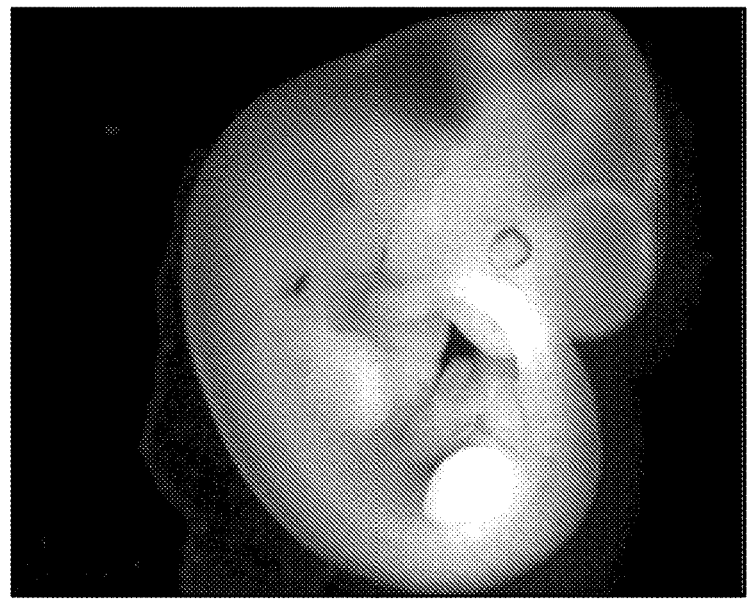
Figure 2B:
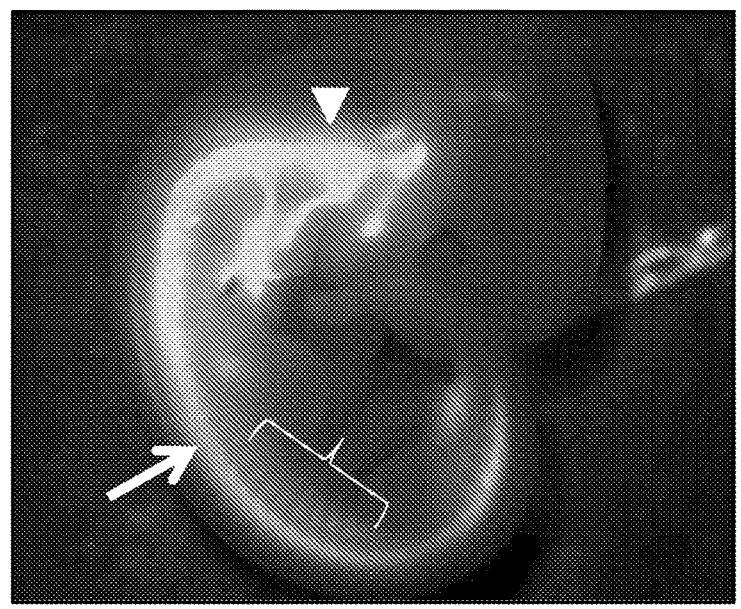

As shown in FIG. 2, an eGFP reporter gene under control of the 908 bp promoter of SEQ ID NO:1 (218p:eGFP short) was expressed in both the cell bodies (FIG. 2B, arrow) and axons (FIG. 2B, bracket) of motor neurons in the spinal cord in E11.5 transgenic mouse embryos. eGFP was also expressed in brainstem motor nuclei of the embryos (FIG. 2B, arrowhead).

7.6 kb miR-218 Promoter Sequence

Figure 4A:
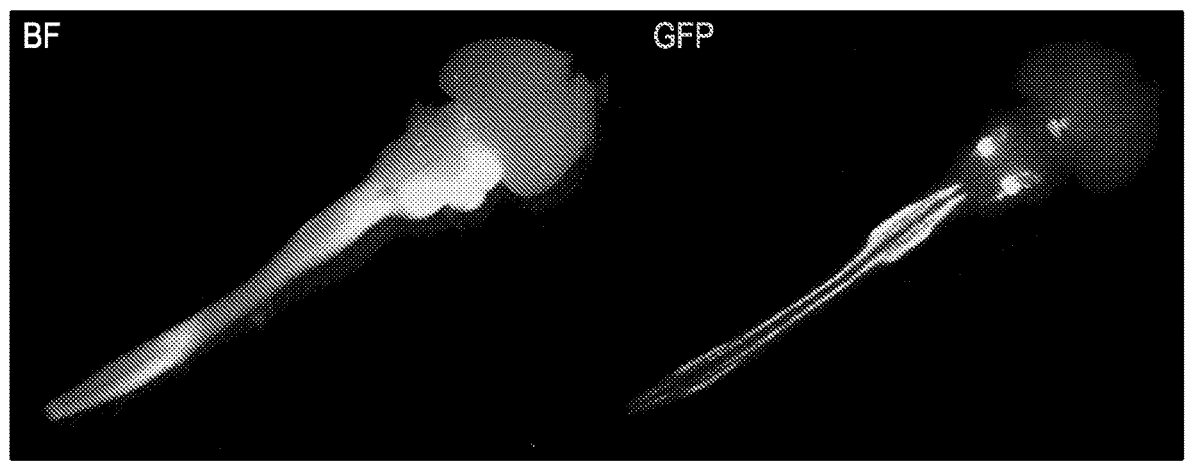
Figure 4B:
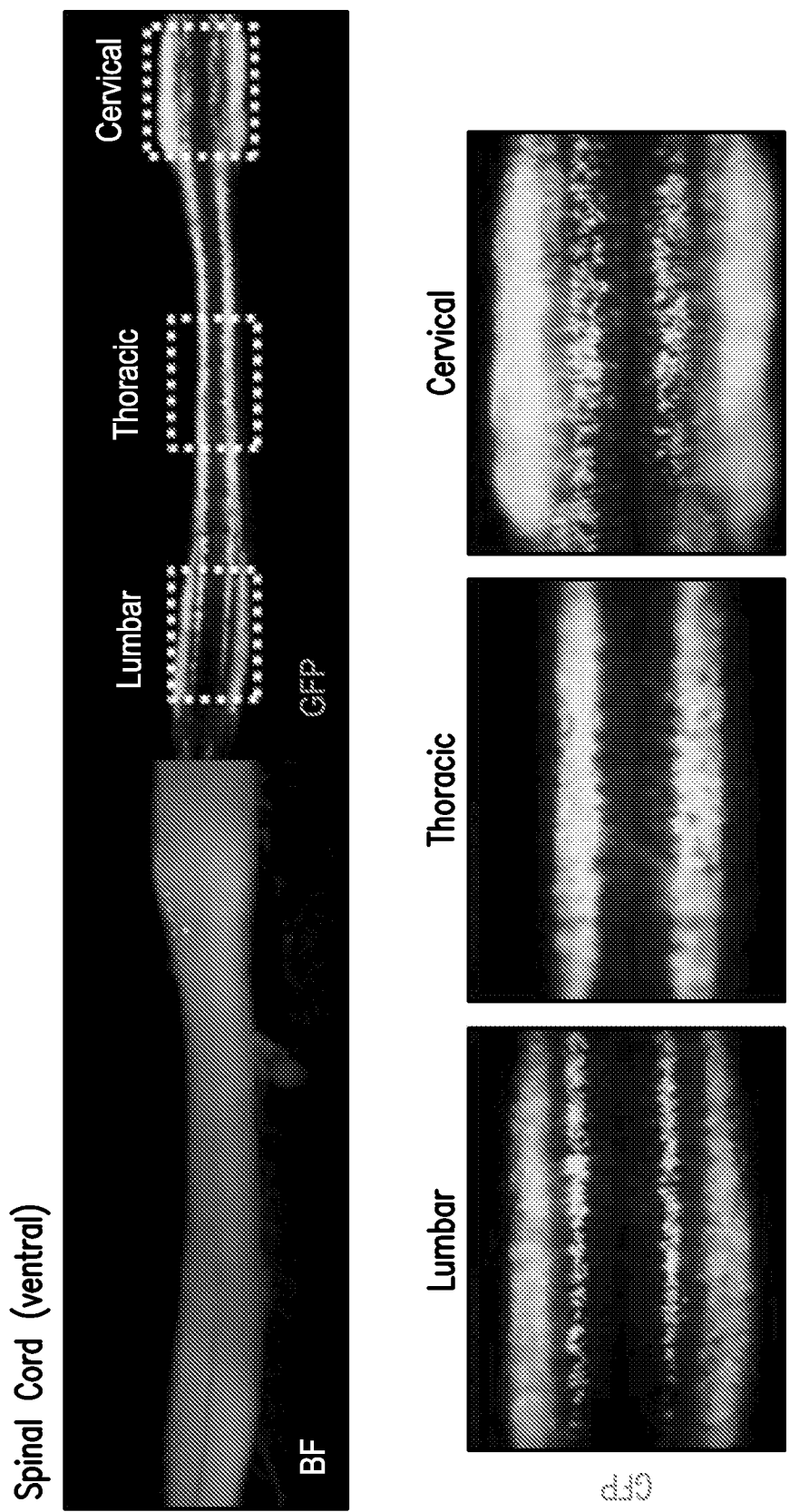
Figure 4C:
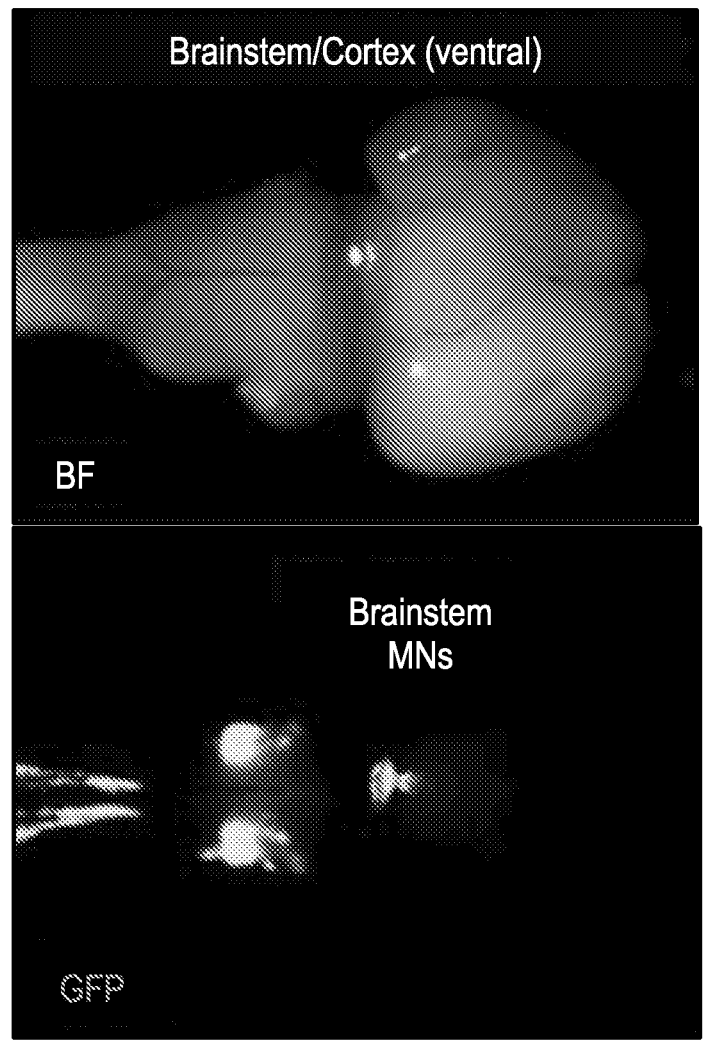
Figure 5:
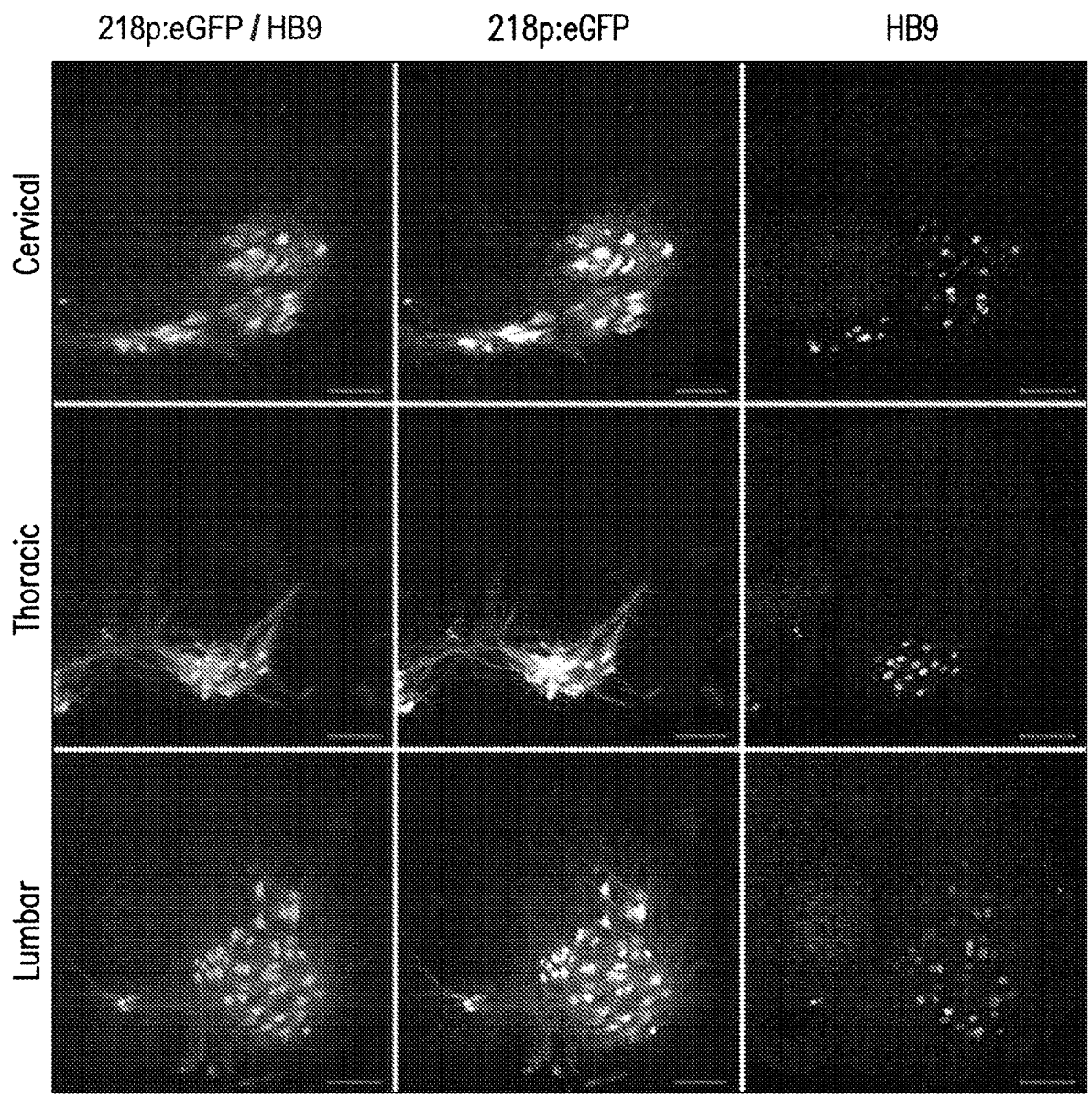
FIG. 5 shows expression of GFP in cross sections of spinal cord from P5 transgenic mice expressing the 7.6 kb miR-218 promoter:eGFP transgene (218p:eGFP) or a homeobox gene (Hb9) promoter:GFP transgene (HB9). Expression of GFP in motor neurons of 218p:eGFP transgenic mice was greater than in HB9 transgenic mice.
Figure 6:
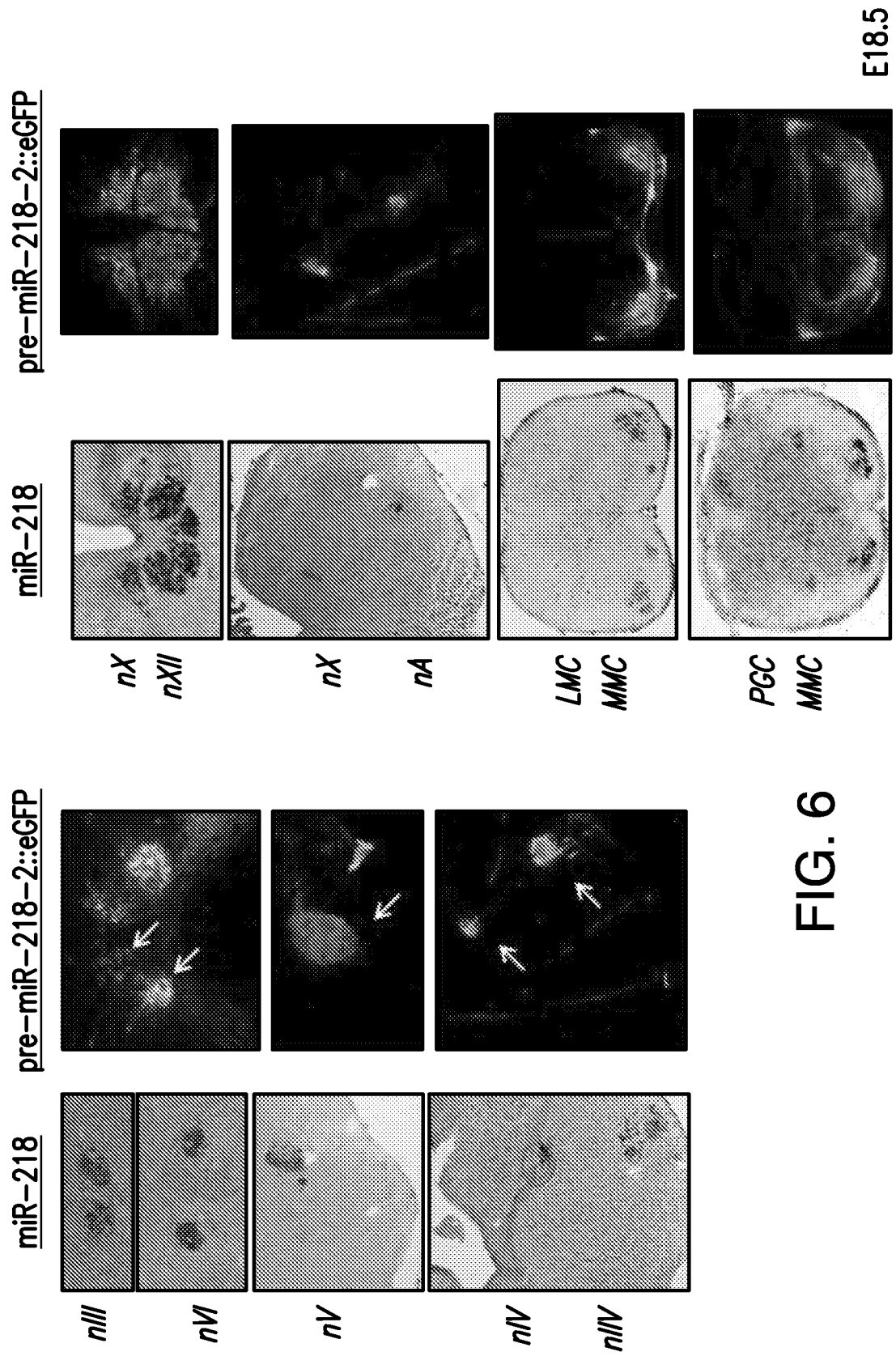
FIG. 6 shows expression of GFP in cranial and spinal motor neurons in E18.5 transgenic mice expressing the 7.6 kb miR-218 promoter:eGFP transgene (pre-miR-218-2:: eGFP) as compared to expression of miR-218 mRNA. miR-218 mRNA was detected by in situ hybridization.

In transgenic mice expressing eGFP under the control of the 7.6 kb miR-218 promoter (218p:eGFP long), eGFP was expressed in motor neurons in E12.5 transgenic mouse embryos (FIG. 3A-B). eGFP expression from the 218p:eGFP long construct was stronger than eGFP expression under control of the homeobox gene (Hb9) promoter (Hb9:GFP) (FIG. 3A). eGFP expression under the control of the 7.6 kb miR-218 promoter (218p:eGFP long) was also detected in the central nervous system of E18.5 transgenic mouse embryos (FIG. 4A-C). eGFP expression was detected in cervical, thoracic and lumbar regions of the spinal cord (FIG. 4B), as well as in brainstem motor neurons (FIG. 4C). Cross sections of spinal cord from P5 mice show expression of GFP in 218p:eGFP long transgenic mice as well as Hb9:GFP transgenic mice. GFP expression in motor neurons was greater in the 218p:eGFP transgenic mice (FIG. 5). FIG. 6 shows expression of 218p:eGFP long in cranial and spinal neurons, as compared to expression of miR-218 mRNA. As shown in FIG. 7, 218p:eGFP long was expressed in both N10 and N12 brainstem nuclei, while Hb9:GFP was only expressed in N12 brainstem nuclei.

In a transgenic *Xenopus laevis* expressing a recombinant transgene comprising the *Xenopus laevis* homolog of the 7.6 kb miR-218 promoter operatively linked to GFP, GFP was expressed in anterior and posterior spinal motor neurons of the swimming tadpole (FIG. 8).

miR-218 Micro RNA is Expressed in Motor Neurons

The micro RNA miR-218 was identified as being highly enriched in motor neurons. Mouse embryonic stem cells (mESCs) carrying a GFP reporter transgene under the control of a homeobox gene (Hb9) promoter (Hb9:GFP), which is expressed in motor neurons, were cultured with retinoic acid (RA) and Sonic Hedgehog (Shh) to differentiate the mESCs into motor neurons. miR-218 micro RNA was identified as being highly enriched in the motor neuron cells (FIG. 9).

miR-218 mRNA expression in mouse motor neurons was assessed by in situ hybridization in mouse embryos. miR-218 mRNA was detected in lumbar motor neurons of E11.5 mouse embryos, lumbar, thoracic and brainstem motor neurons of E12.5 mouse embryos, lumbar motor neurons of P0 mice, and lumbar motor neurons of adult mice (FIG. 10). miR-218 mRNA was detectable in motor neurons in E11.5 mouse embryos after the cells migrated to the ventro-lateral spinal cord (FIG. 11). miR-218 mRNA was also detected in all brainstem and spinal motor neurons in the P0 mouse central nervous system (FIG. 12).

Conclusion:

A single microRNA (miR-218) is abundantly expressed and specifically enriched in all brainstem and spinal motor neuron subtypes. miR-218 is encoded within the Slit2/3 genetic loci, however, novel motor neuron-specific alternative promoters drive pri-miR-218 expression independently of Slit2/3 promoters. miR-218 directly targets many transcriptional modifiers, and indirectly activates many genes involved in synaptic transmission. The miR-218-KO motor neuron transcriptome globally shifts towards that of 'generic' ventral spinal cord interneurons. Furthermore, the 908 bp miR-218 promoter exhibited specificity and intensity that were comparable to the full 7.6 kb miR-218 promoter.

6.2 Example 2: Loss of Motoneuron-Specific microRNA-218 Causes Systemic Neuromuscular Failure Summary:

Dysfunction of microRNA metabolism is thought to underlie diseases affecting motoneurons. One microRNA, miR-218, is abundantly and selectively expressed by developing and mature motoneurons. Here, we show that mutant mice lacking miR-218 die neonatally and exhibit neuromuscular junction (NMJ) defects, motoneuron hyperexcitability, and progressive motoneuron cell loss—hallmarks of motoneuron diseases such as amyotrophic lateral sclerosis (ALS) and spinal muscular atrophy (SMA). Gene profiling reveals that miR-218 modestly represses a cohort of hundreds of genes that are neuronally-enriched, but are not specific to a single neuron subpopulation. Thus, the set of mRNAs targeted by miR-218, designated TARGET[218], define a neuronal gene network that is selectively tuned-down in motoneurons to prevent neuromuscular failure and neurodegeneration.

Methods:

Mouse Lines

The following mouse lines were used: Hb9:gfp, Chx10:Cre (29), Sim1:Cre (30), En1:Cre (Jax 007916), Wnt1:Cre (Jax 003829), and Rosa:LSL:tdtomato (Jax 007905). En1:Cre, Sim1:Cre, Wnt1:Cre, and Chx10:Cre males were crossed with Rosa:LSL:tdtomato females to generate embryos in which specific the respective neuronal populations express tdTomato.

miR-218-1 and miR-218-2 knockout mice were generated using CRISPR/Cas9 targeting, as described (11). Briefly, Cas9 mRNA was in vitro transcribed, capped and polyadenylated using the Invitrogen mMachine kit. Guide RNAs were designed using crispr.mit.edu to decrease the likelihood of off-target effects and were in vitro transcribed using the New England Biolabs High Yield In Vitro Transcription Kit (guide sequences available in Supplemental Table 2). Mouse oocytes were microinjected with Cas9 mRNA:gRNA:gRNA mixtures (at concentrations of 30 ng/uL:15 ng/uL:15 ng/uL) and were reimplanted into B6D2F1 pseudopregnant females. Successful multiplexed deletions were detected by PCR genotyping (see Supplemental Table 2 for primer information) and confirmed by Sanger sequencing, and positive founders were maintained and used for breeding. miR-218-1$^{+/-}$, miR-218-2$^{+/-}$ and Hb9:gfp mice were bred to generate 218$^{DKO}$; Hb9:gfp embryos.

Immunohistochemistry and In Situ Hybridizations

Briefly, tissue was fixed in 4% PFA for 2 hours at 4 C, washed in PBS o/n, cryoprotected in 30% sucrose for 30 minutes before mounting and freezing in OCT. miRNA in situ hybridizations were performed on whole mount embryos and tissue sections according to standard protocols (Exiqon) using a 5'/3'-DIG pre-labelled miR-218 LNA probe (cat: 18111-15; Exiqon). For dual in situ hybridization and immunofluorescence, in situ hybridization was performed first followed by the incubation of tissue sections in primary and secondary antibodies for immunohistochemistry.

Human spinal cords were obtained from NIH Tissue Bank. Microdissections of mouse tissues were performed under a Zeiss Stemi SV6 microscope, and imaging was performed with a Leica confocal CTR6500 (TCS SPE) microscope or Zeiss Lumar V12 stereomicroscope.

Antibodies: goat anti-ChAT (Millipore; AB144P), Rabbit anti-Neurofilament (Chemicon AB1987), mouse anti-Neurofilament (Developmental Studies Hybridoma Bank (DSHB), 2H3 for whole embryo staining), guinea pig anti-Lhx3 (#718), rabbit anti-Isl1/2, rabbit anti-Hb9 (#6055), mouse anti-Tag1 (DSHB, 3.1C12), rabbit anti-TrkA (Millipore; 06-574), rabbit anti-NeuN (Millipore; ABN78), alpha-bungarotoxin-tetramethylrhodamine for AChR labelling (Life Technologies T-1175), rabbit anti-Synaptophysin (Santa Cruz: sc-9116), rabbit anti-GFP (Invitrogen).

Flat Mounts

E12.5 flat mounts were prepared by decapitating and eviscerating Hb9:gfp+ embryos, fixing in 4% PFA for 2 hours at 4 C, washing with PBS 3×, and sequentially transferring the tissue from 30%, 50%, 80% glycerol every 2 hours. Cleared flat mount tissue was mounted between two glass coverslips before imaging with Zeiss Lumar V12 stereomicroscope.

E14.5 flat mounts were prepared by removing the limbs of tg(218-2::eGFP) embryos, dissecting skin from muscle tissue, fixing in 4% PFA for 2 hours at 4 C, washing with PBS 3×, and sequentially transferring the tissue from 30%, 50%, 80% glycerol every 2 hours. Cleared flat mount tissue was mounted between two glass coverslips before imaging with Zeiss Lumar V12 stereomicroscope. The tg(218-2::eGFP) transgene was used for these experiments due to the significantly brighter expression of fluorescence compared with the Hb9:gfp transgene allowing for more detailed imaging.

Slice Preparation for Intracellular Recording

Hb9:gfp+E18.5 embryos were removed from the uterus under isoflurane anesthesia and spinal cords were quickly isolated in ice cold, oxygenated 95% O2/5% CO2, ACSF containing (in mM): 128 NaCl, 2.5 KCl, 0.5 NaH$_2$PO$_4$, 21 NaHCO$_3$, 30 D-Glucose, 3 MgSO$_4$, and 1 CaCl$_2$ at pH=7.4 and 300-305 mOsm. 218DKO mutants were identified by postmortem PCR genotyping. Lumbar regions of the spinal cords were isolated and mounted in low melting point agarose (4% in a CSF) held at 37 C in plastic molds. After mounting, molds were immediately placed on ice until agarose solidified, and spinal cords were sliced coronally (300 μm) on a Leica VT1000S vibratome in an ice cold, oxygenated bath of aCSF. Spinal slices were transferred to a holding chamber and allowed to recover for a half hour at 32 C and then transferred to an oxygenated holding chamber containing ACSF (in mM): 128 NaCl, 2.5 KCl, 0.5 NaH$_2$PO$_4$, 26 NaHCO$_3$, 25 D-Glucose, 1 MgSO$_4$, 2 CaCl, 0.4 ascorbic acid, and 2 Na-Pyruvate at pH=7.4 and 300-305 mOsm at 28 C.

Whole-Cell Current Clamp Recordings

Following an hour of recovery a spinal slice was transferred to a recording chamber (Warner) which was continuously perfused with ACSF at a rate of 1-2 mL/min heated with an inline heater (Warner) to 28 C. Pulled thin-wall glass electrodes (WPI) with a tip resistance of 3.5-4.5 MΩ were filled with a potassium methanesulfonate based intracellular recording solution (in mM): 135 KMeSO$_4$, 5 KCl, 0.5 CaCl$_2$, 5 HEPES, 5 EGTA, 2 Mg-ATP, and 0.3 Na-GTP at pH=7.3 and 285-290 mOsm. MultiClamp 700A amplifier and Digidata 1322a Digitizer (Molecular Devices) was used for data acquisition. Whole-cell recordings were filtered at 2 kHz and digitized at 10 kHz and monitored using pClamp 9 software. Liquid junction potential was not corrected for. Whole-cell current clamp experiments targeted large, Hb9:gfp+ motoneurons located in the lateral motor column of the ventral horn under 40×DIC magnification with a high speed IR camera (QImaging). eGFP epifluorescence co-localization was confirmed prior to break-in. Following 5 minutes post break-in whole-cell configuration membrane properties were collected at a holding potential of −70 mV. Series resistance ranged between 8-20 mOhms and any cells with changes>20% over the duration of the recording were discarded. Resting membrane potential was calculated 5 minutes following the transition to current clamp mode from the average of ten consecutive sweeps. The rheobase current was determined from a series of 5s square pulses (−250 pA and up, 50 pA steps) given at 20 second intervals to allow slow conductances to recover to their initial state. The first sweep to elicit an action potential was considered the rheobase current. For a more precise measure of rheobase current, the recruitment current coinciding with the first action potential on 0.1 nA/sec current ramps (5 sec duration) repeated 10 times (20s interval) were measured. Voltage spiking threshold on the first spike was measured by finding the voltage first derivative value greater than 10 mV/ms. Input conductance was measured as the slope of the current-voltage relationship by determining the steady state current at negative current injections (−100 to −10 pA, 30 pA steps). Ih current amplitude was measured during hyperpolarizing current injections as the peak current minus steady state current. AHP amplitude was measured by single action potentials elicited by 1 ms square pulses (2-4 nA) and AHP decay tau was fit with a single exponential.

Ventral Root Recordings

At E18.5, spinal cords from wild-type and 218$^{DKO}$ animals were isolated in cold oxygenated dissection ACSF (128 mM NaCl; 4 mM KCl; 21 mM NaHCO3; 0.5 mM NaHPO$_4$; 3 mM MgSO$_4$; 30 mM D-glucose; and 1 mM CaCl$_2$), and transferred to oxygenated room temperature recording ACSF (128 mM NaCl; 4 mM KCl; 21 mM NaHCO$_3$; 0.5 mM NaH$_2$PO$_4$; 1 mM MgSO$_4$; 30 mM D-glucose; and 2 mM CaCl$_2$). Suction electrodes were attached to the L2 and L4 or L5 ventral roots, and cords were then allowed to recover and equilibrate to room temperature for ~20 min. Pharmacologic induction of fictive locomotor activity was performed by bath application of 10 μM N-methyl-D,L-aspartate and 20 μM serotonin. Motoneuron activity was recorded, amplified 1000×, and filtered from 100 Hz-3 Hz.

Analysis of fictive locomotor activity phase and cycles was conducted offline with custom written scripts in R.

FACS and RNA Isolation

Spinal cords from E12.5 mice were micro-dissected using a Leica stereomicroscope and dissociated with papain (papain dissociation kit, Worthington Biochemical) for 45 minutes. Dissociated spinal tissue was triturated and centrifuged at 1000 rpm for 5 minutes. Cells were resuspended in 1:1 Neurobasal:DMEM/F12 (without phenol red) with 3% Horse Serum (Invitrogen) and DNase (Worthingon Biochemical) and passed through a 35 μm cell strainer (BD Falcon 08-771-23). Cells were sorted on a Becton Dickinson FACS Vantage SE DiVa using Coherent Sapphire 488 nm and 568 nm solid state lasers (200 mW) and collected directly into miRvana RNA lysis buffer.

Collected cells were stored at −80C until RNA was collected using the miRvana miRNA isolation kit (Ambion AM1560). Samples were genotyped by PCR prior to RNA isolation. For both small RNA and polyA+ RNA sequencing experiments, the protocol for total RNA collection was used. RNA collected from cells isolated from one to (at most) three spinal cords were combined before sequencing to obtain at least 100 ng RNA (determined by Agilent TapeStation) for library preparation.

RNA Sequencing and Gene Expression Quantification mRNA sequencing libraries were prepared using the TruSeq RNA Library Preparation Kit (v2) according to the manufacturer's instructions (Illumina). Briefly, RNA with polyA$^+$ tails was selected using oligo-dT beads. mRNA was then fragmented and reverse-transcribed into cDNA. cDNA was end-repaired, index adapter-ligated and PCR amplified. AMPure XP beads (Beckman Coulter) were used to purify nucleic acids after each step.

Small RNA-sequencing libraries were prepared using NEBNext Small RNA Library Prep for Illumina. Briefly, 3' adapter was ligated to total RNA, any excess 3' adaptor were quenched by hybridization of reverse transcription primer to prevent primer dimers. RNA was then ligated to 5' adaptor, reverse transcribed and PCR amplified.

Libraries were then quantified, pooled and sequenced using either the Illumina HiSeq 2500 or Illumina HiSeq 2000 platforms at the Salk NGS Core and Beijing Genomics Institute. Raw sequencing data was demultiplexed and converted into FASTQ files using CASAVA (v1.8.2). A total of 50-base pair (bp) single-end reads or 100-bp paired-end reads were aligned to the mouse genome using Bowtie, allowing up to three mismatches per alignment and up to 20 alignments per read, filtering out any read aligning in more than 20 locations. For consistency in comparing some data sets, read lengths were cut down to 50 by (from the 3' end). All samples were filtered by removing reads with average base quality before 15.

Isoform gene expression quantification was performed using Sailfish (by Lane Center for Computational Biology at Carnegie Mellon University) using the mm10 Refgene transcriptome database (available at the University of California, Santa Cruz Genome Browser). Isoform expressions were summed per gene locus to create gene-level expression for downstream fold change comparisons between groups.

Data Analysis Methods (28A) Normalized reads per kilobase (NRPK) values of replicates (n=6 (WT), n=2 ($218^{DKO}$)) were averaged. Genes that were not expressed by at least 10 NRPKs in either the wild type or $218^{DKO}$ data sets were eliminated. Significance p-values were determined by a two-tailed heteroscedastic t-test in Excel.

TargetScan6 context+scores are a predictor of efficacy of miRNA targeting with more negative scores denoting a greater predicted efficacy of repression. context+values were obtained from TargetScanHuman (by Whitehead Institute for Biomedical Research). A cutoff of <−0.15 for context+ scores to be designated a TARGET[218] gene was empirically established.

(28C) Differential NRPK expression of TARGET[218] genes in wild-type motoneurons versus each interneuron subtype (n=6 (WT), 1 (V1), 1 (V2a), 1 (V3)).

(28E) Heirarchical clustering was performed with GENE-E software, using city block distances.

(29A) RNA sequencing reads were aligned on the transcript-specific level (mm10, transcript database obtained from UCSC genome browser). NRPKs of gene expression in wild-type motoneuron replicates were averaged, and NRPKs of gene expression in from V1, V2a, and V3 interneurons were averaged. The top 15,000 most highly expressed genes (as determined by maximum NRPK level in either data set) were used for Sylamer motif enrichment analysis. Sylamer software was used to assess miRNA seed match enrichment p-values. A FASTA file of 3'UTRs masked and purged of low complexity and redundant sequences was obtained from and exported from Sylarray. Transcripts were ranked by differential expression (most enriched in motoneuron to most depleted in motoneurons) to generate a ranked transcript list for Sylamer analysis. Sylamer settings: 7 bp, bin size 2, markov correction 4, known miRNA seeds only. Enrichment p-values were exported and plotted in one-dimension using Prism GraphPad.

(29B and C) For RNA sequencing data sets from cortical projection neurons, raw data sets were obtained from data sets associated with DeCoN (24) and were aligned to the genome using the same methods as in-house generated data sets. NRPK values from cortical neuron duplicates (E15.5 data set only) were averaged before performing Sylamer analysis (as above).

Results:

Motoneurons are a specialized neuronal subpopulation within the central nervous system (CNS) that establish synaptic connections with muscles to regulate movement. Diseases such as ALS and SMA, which affect motoneurons, seem to share a common pathogenic mechanism based on defective RNA metabolism and biogenesis of microRNAs (1-5). Consistent with earlier descriptions of miR-218 expression in embryonic motoneurons (6, 7), we found that miR-218 was the most abundant motoneuron microRNA and was enriched ~27-fold, as determined by small RNA sequencing of FACS-purified Hb9::gfp$^+$ motoneurons from embryonic mouse spinal cords (FIG. 26A). The spinal cord is comprised of many interneuron subtypes (8). We found that V2a and V3 ventral spinal interneurons did not express a single characteristic microRNA (FIG. 30A), indicating motoneurons may be distinctly reliant on cell type-specific microRNA expression.

We detected miR-218 within visceral and somatic spinal motoneurons (FIG. 26B, FIG. 30B) and brainstem motor nuclei (FIG. 30C). Robust miR-218 expression persisted postnatally in α- and γ-choline acetyltransferase (ChAT)-positive motoneurons (FIG. 26C, FIG. 30D) but not ChAT+ interneurons (FIG. 30E) Likewise, miR-218 was selectively expressed in human embryonic motoneurons (FIG. 30F). Compared with the extensive catalog of protein markers that delineate motoneuron subtypes (8), miR-218 is remarkable for its expression spanning motoneuron classes from embryonic stages into adulthood (FIG. 30G) and its undetectable expression in other tissues.

Figure 26F:
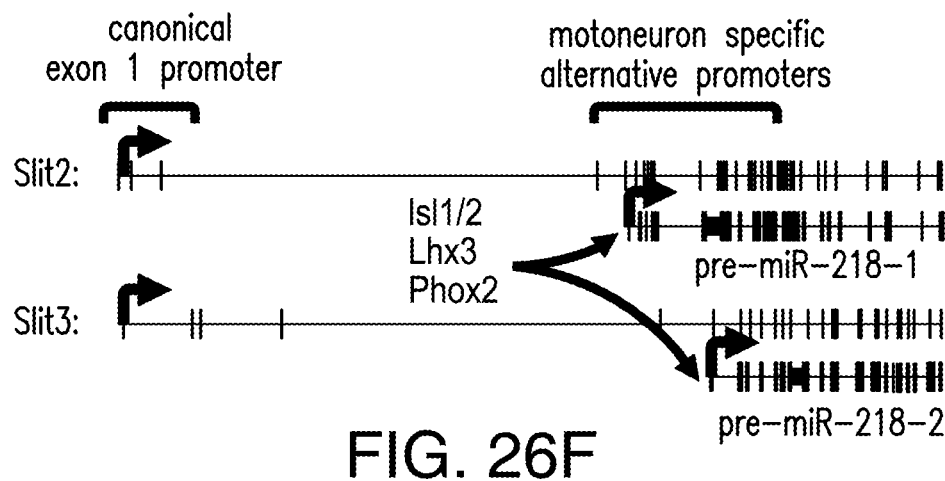
Figure 26G:
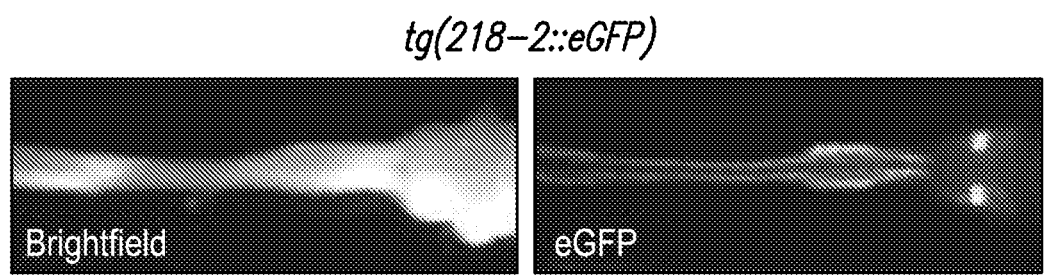
Figure 26H:
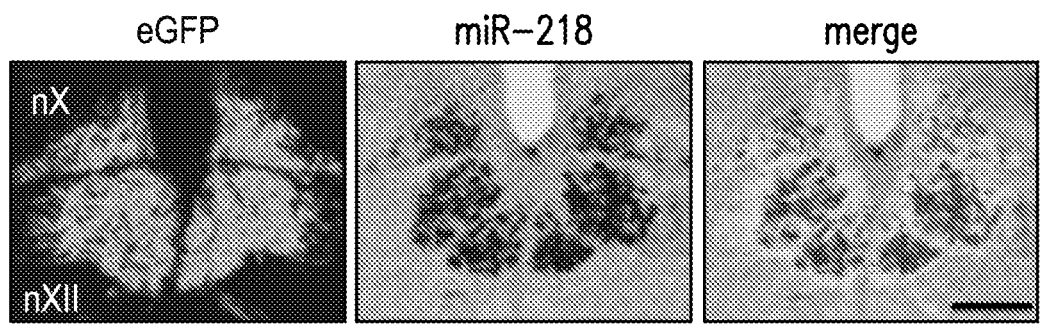

Two paralogs of miR-218 are present in mammals, miR-218-1 and miR-218-2, embedded within homologous introns of the Slit2 and Slit3 genes, respectively. The motoneuron-specifying transcription factors Isl1 and Lhx3 have been suggested to upregulate miR-218 by increasing transcription of Slit2 and Slit3 (6). We investigated Slit2 and Slit3 mRNA expression in motoneurons by RNA sequencing and discovered that both genes were transcribed using start sites located upstream of exon 6 (FIG. 26D, FIGS. 31A and B). This intronic start site was not used by adjacent floor plate glial cells expressing Slit2 and Slit3. Previously mapped Isl1/2, Lhx3, and Phox2a ChIP peaks (9) were observed at conserved hexamer DNA response elements (HxREs) proximal to exon 6 (FIG. 26E), suggesting the presence of intragenic motoneuron-specific promoters (FIG. 26F). To test this hypothesis, we generated a transgenic mouse line, tg(218-2::eGFP) with a 7.4 kilobase (kb) sequence containing putative regulatory elements (FIG. 31C). In vivo, eGFP was expressed in tg(218-2::eGFP) spinal and cranial motoneurons, reproducing miR-218's endogenous expression pattern (FIGS. 26G and H, FIG. 31C). These findings demonstrate that primary miR-218 transcripts are under independent activation in motoneurons by promoters distinct from those that generate Slit2 and Slit3 full-length transcripts in other tissues.

Figure 33G:
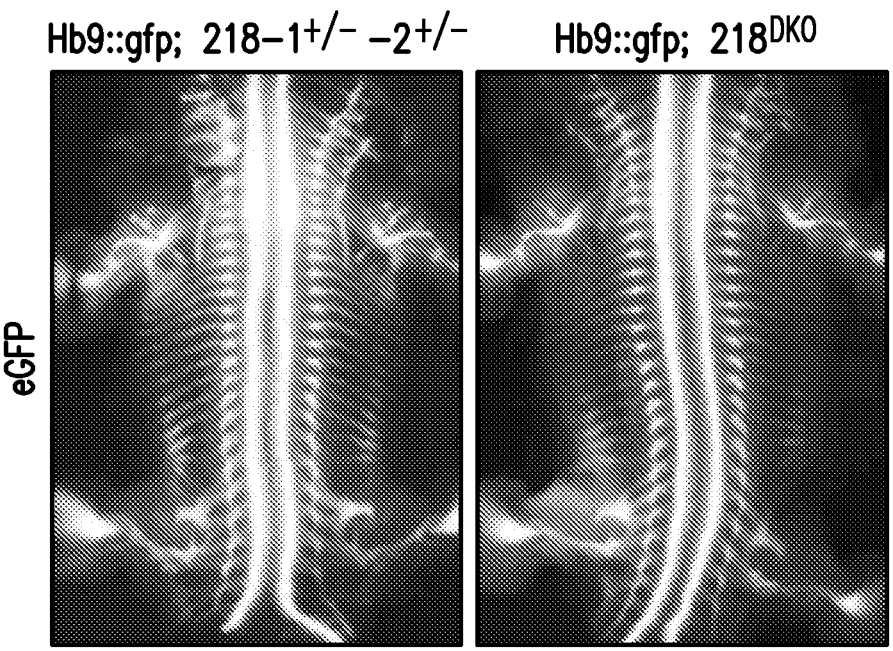
Figures 33H, 33I:
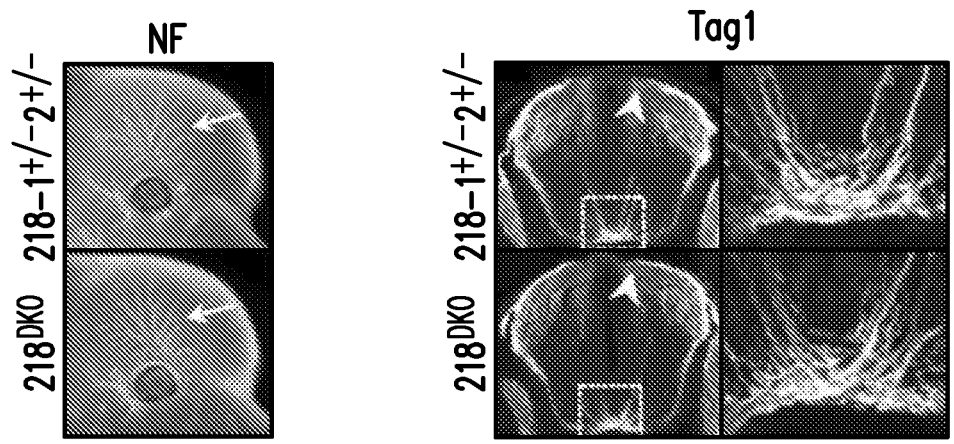

Studies in vitro and in chick embryos have suggested miR-218 may contribute to motoneuron specification (6), however, such microRNA knockdown and overexpression studies can yield non-physiological affects (10). To determine the biological impact of miR-218 disruption in vivo, we used CRISPR/Cas9 gene editing (11) to create microdeletions of miR-218-1 and miR-218-2 precursor sequences in mouse (FIG. 27A, FIG. 32A-D). miR-218 expression was detected in miR-218-1$^{-/-}$ and at lower levels in miR-218-2$^{-/-}$ motoneurons, but was undetectable in miR-218-1$^{-/-}$ 2$^{-/-}$ double knockout ($218^{DKO}$) motoneurons (FIG. 27B, FIG. 32E-H). We found that the number and spatial organization of motoneurons in E12.5 spinal cords of $218^{DKO}$ mutants were unchanged compared to controls (FIG. 33A-F). Subsequent developmental events including axonal exit from the spinal cord, outgrowth, and peripheral pathfinding were indistinguishable between Hb9::gfp$^+$ control and $218^{DKO}$ embryos (FIG. 33G). $218^{DKO}$ mutants displayed none of the phenotypes characteristic of Slit2 and Slit3 disruption (FIGS. 33H and I)(12, 13), indicating Slit2 and Slit3 function is unaffected by the intronic microdeletions. We conclude that miR-218 is dispensable for in vivo motoneuron fate specification and gross early motoneuron development.

However, $218^{DKO}$ mice were never viable (FIG. 34A). $218^{DKO}$ embryos exhibited akinesia, kyphosis, and weak or absent responses to pain stimulation after cesarean delivery at E18.5 and died within minutes due to an apparent lack of respiration (FIG. 27C)—a phenotype similar to mice carrying null alleles of Agrin, MuSK, choline acetyltransferase (ChAT) and other components required for neuromuscular transmission (14). Consequently, we investigated whether loss of miR-218 impacts neuromuscular synaptogenesis, an intricate process in which motor nerves first innervate muscle and subsequently form pre-synaptic specializations with post-synaptic acetylcholine receptors (AChRs) expressed by developing muscle (15). We examined glycerol-cleared tg(218-2::eGFP) embryos and found that the motor nerves of $218^{DKO}$ motoneurons reached E14.5 limb tissue (FIG. 34B). However, motor axons appeared to lack penetrating, fine intra-muscular branches across limb (FIG. 27D), diaphragm and intercostal muscle groups (FIG. 27E, FIG. 35A-B). At E18.5, the majority of a-bungarotoxin-labelled AChR+ clusters lack motor innervation in $218^{DKO}$ limb muscles (FIG. 27F, FIG. 35C), reflecting a gross failure of motoneurons to establish neuromuscular junctions needed to control body movements.

Figure 37I:
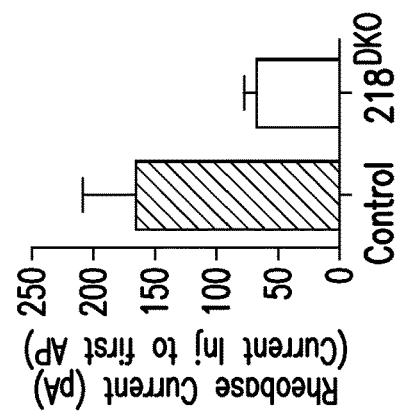
Figure 37H:
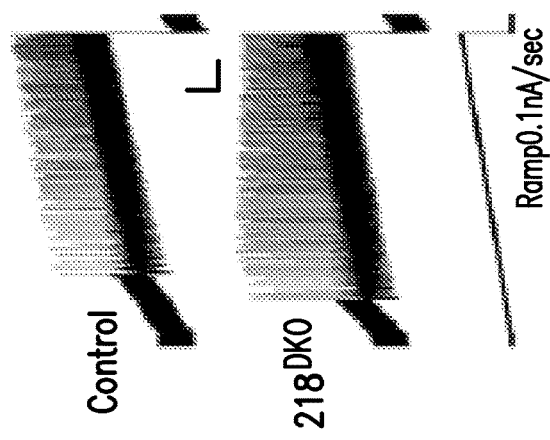
Figure 37G:
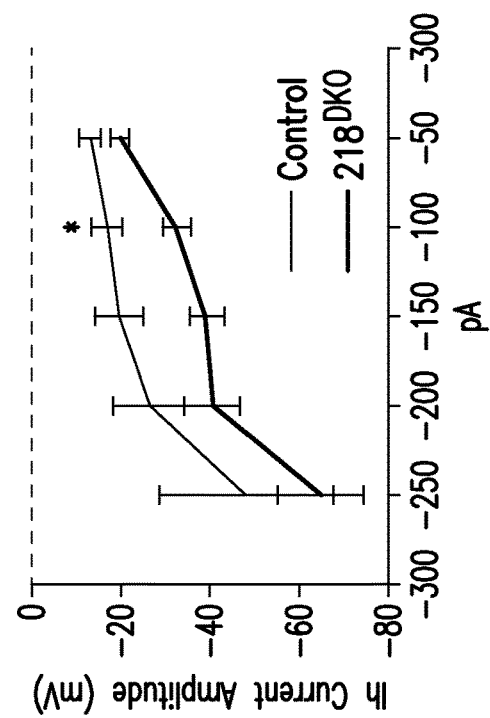
Figure 37J:
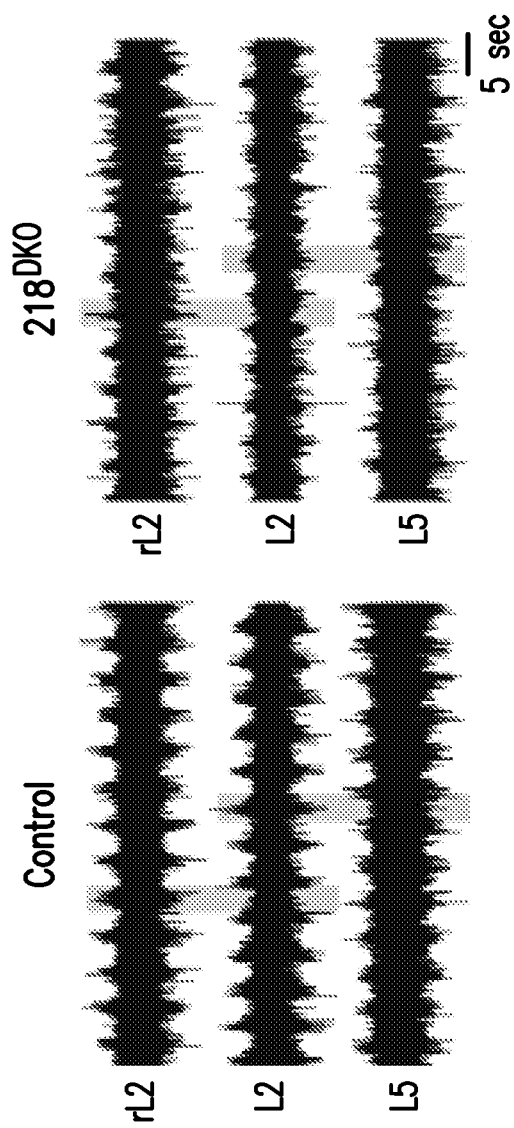

While $218^{DKO}$ mutants had normal numbers of motoneurons at E12.5 (FIG. 27G), $218^{DKO}$ mutants had 18 to 36% fewer motoneurons at cervical, thoracic, and lumbar spinal cord segments at E18.5, indicating neurodegenerative cell loss (FIG. 27H; FIG. 36A-B). To examine whether the physiology of the remaining motoneurons was altered in mice lacking miR-218, we assessed fictive locomotion (16) and performed intracellular recordings of Hb9::gfp$^+$ LMC α-motoneurons from E18.5 lumbar spinal slices (FIG. 37A). Left/right and flexor/extensor activation of motor roots were normal in $218^{DKO}$ spinal cords, and motoneuron resting membrane potentials, capacitances, resistances, and holding currents were similar between control and $218^{DKO}$ motoneurons (FIG. 37B-J). However, action potentials were elicited by a 4.4-fold lower rheobase current in $218^{DKO}$ motoneurons compared with controls (FIGS. 27I and J), indicative of membrane hyperexcitability. Thus, miR-218 does not significantly contribute to early motoneuron development, but it is critical for the regulation of neuromuscular synapses, membrane excitability, and motoneuron survival.

These phenotypic defects suggested that motoneuron-specific gene regulation depends on the post-transcriptional repression of miR-218 target mRNAs. To extend beyond microRNA-target identification studies performed in vitro using cancer cell lines (6, 17), we identified miR-218 gene targets within motoneurons by performing polyA$^+$ RNA sequencing of FACS-isolated Hb9::gfp$^+$ motoneurons from wild type and $218^{DKO}$ E12.5 spinal cords, before the apparent onset of defects (FIG. 38A). Using Sylamer (18), we determined that 6 bp, 7 bp and 8 bp 3'UTR complementary seed matches to miR-218 were enriched within genes expressed higher in $218^{DKO}$ motoneurons than controls (FIG. 38B-E), reflecting widespread de-repression of miR-218 target genes in $218^{DKO}$ motoneurons.

Figure 28A:
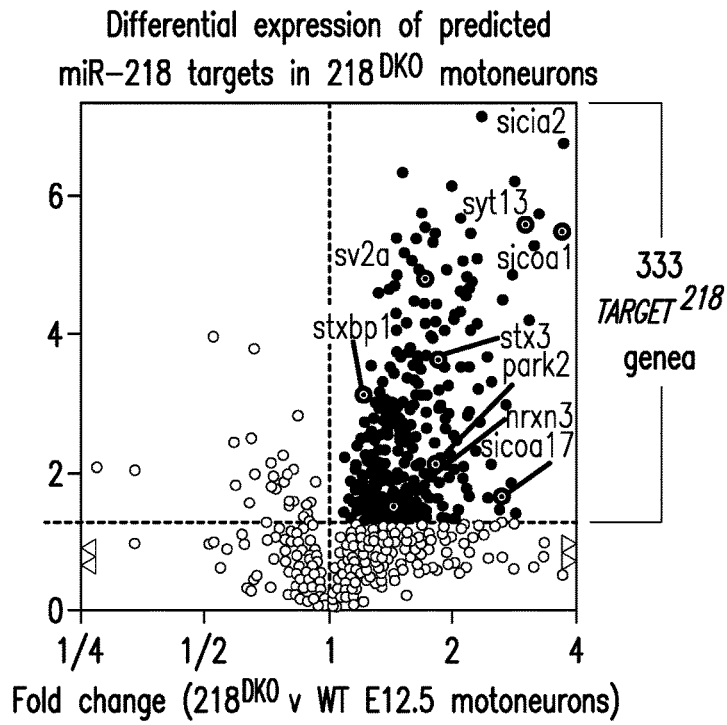
Figure 28B:
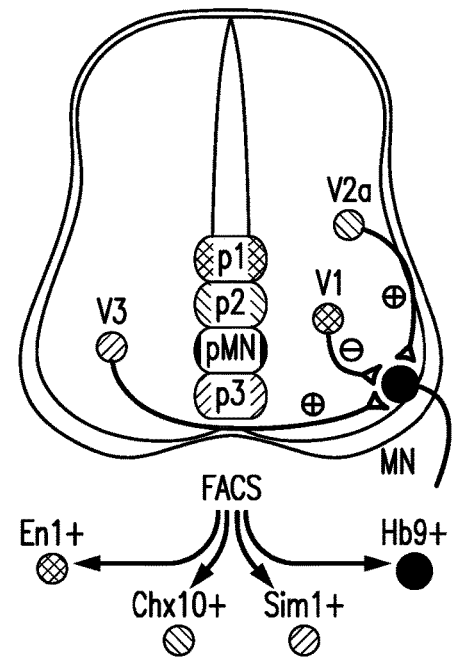

We identified 333 miR-218 target genes that met the following criteria: expression>10 normalized reads per kilobase (NRPK), possession of miR-218 binding sites (context+score≤−0.15, TargetScan6)(19), and significant upregulation in $218^{DKO}$ versus wild type motoneurons (FIG. 28A). This cohort of 333 genes is likely to be under direct miR-218 mediated repression, and we named this coordinately regulated gene set TARGET$^{218}$. TARGET$^{218}$ genes are enriched for neurotransmission and neurotransmitter transport biological processes (FIGS. 38F and G). The most highly upregulated TARGET$^{218}$ gene, Slc1a2/GLT-1 (266% increase), is a glutamate reuptake transporter known to be modulated by riluzole—the only medication approved for the treatment of ALS (20). On average, TARGET$^{218}$ genes were expressed 61.1% higher in $218^{DKO}$ motoneurons, and 47 of these genes were increased by at least 2-fold (FIG. 40). The wide breadth of target genes affected in $218^{DKO}$ motoneurons suggests miR-218 shapes expression of an extensive genetic network, rather than merely modulating a small group of individual genes within a single molecular pathway.

Figure 28C:
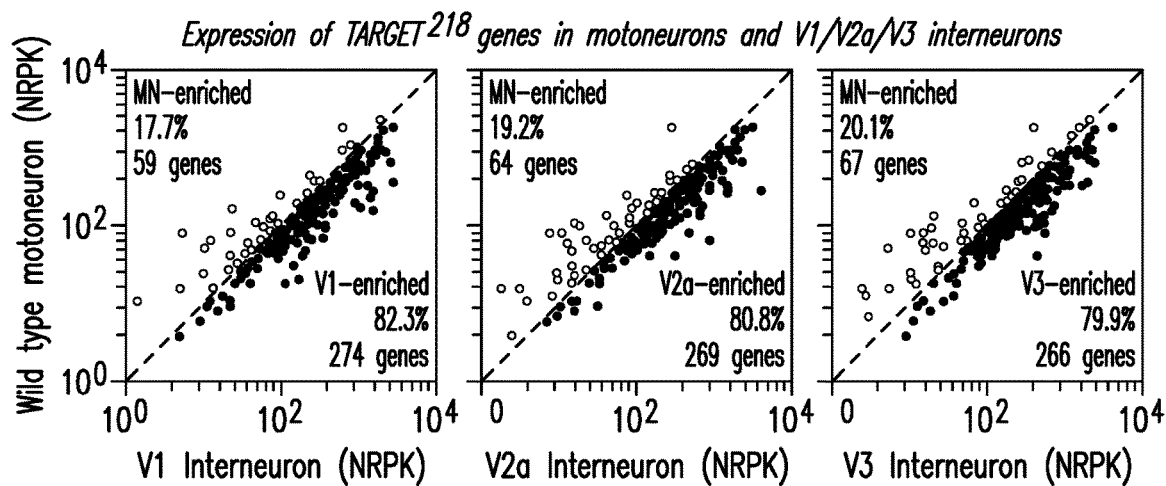
Figure 28D:
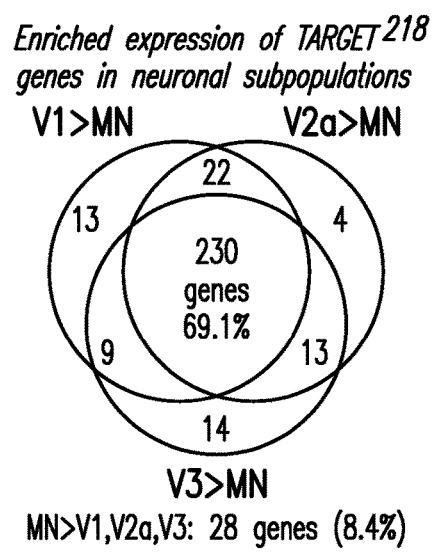
Figure 28E:
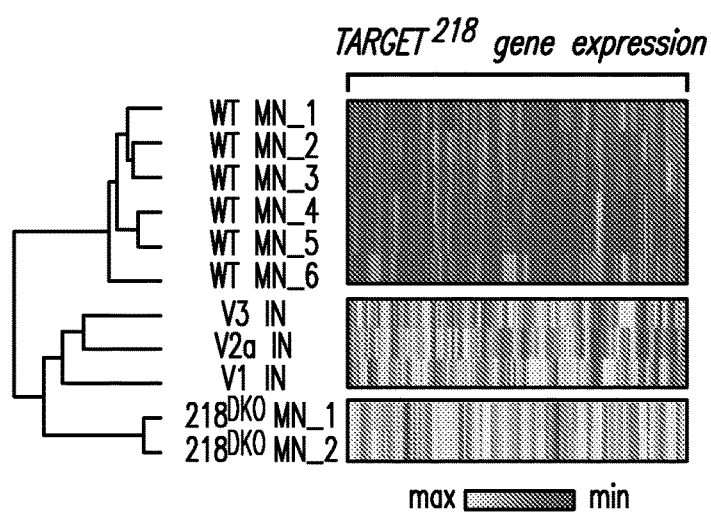

Other microRNA-gene regulatory networks have been shown to reinforce the repression of differentiation programs to confer robustness to cell-fate decisions (21-23), however, the lack of cell specification errors in $218^{DKO}$ embryos suggested that miR-218 might have a novel regulatory role. We evaluated whether the TARGET$^{218}$ gene network was expressed higher or lower in motoneurons compared with other spinal neuronal subpopulations by gene profiling FACS-purified interneuron subpopulations labelled by genetic reporters: GABAergic-V1 (En1:Cre), glutamatergic-V2a (Chx10:Cre), and glutamatergic-V3 (Sim1:Cre) spinal interneurons (FIG. 28B, FIG. 39A-C). We found that ~80% TARGET$^{218}$ genes are expressed lower in wild type motoneurons versus each of V1, V2a, and V3 interneurons (FIG. 28C). Moreover, the majority (69.1%) of TARGET$^{218}$ genes are expressed lower in wild type motoneurons versus all three of the spinal interneurons subpopulations profiled (FIG. 28D). These findings suggest miR-218 represses a gene network shared across interneuron subpopulations, but not specific to a single one. Furthermore, hierarchical clustering revealed that 218$^{DKO}$ motoneurons express TARGET$^{218}$ genes at levels more similar to V1, V2a and V3 interneurons than to wild type motoneurons (FIG. 28E). Thus, rather than reinforcing a preexisting 'low' target gene expression in motoneurons, miR-218 establishes the low TARGET$^{218}$ expression observed in motoneurons relative to interneurons.

To evaluate microRNA-mediated repression in an unbiased manner, we bioinformatically evaluated the statistical enrichment of binding sites for all microRNAs across the transcriptome of investigated cell types. Using Sylamer (18), we determined the hypergeometric statistical enrichment of 7 bp 3'UTR sequences complementary to known microRNA seed sequences (microRNA seed matches) in transcripts expressed higher or lower in motoneurons versus interneurons (FIG. 29A). We found that 3'UTR seed matches to miR-218 are significantly enriched in transcripts expressed lower in wild type motoneurons versus averaged (FIG. 29A) and individual spinal interneuron subpopulations—and even distantly located cortical neuron subpopulations (FIG. 29B) (24). 3'UTR seed matches to miR-218 were no longer found to be enriched in genes expressed higher or lower in 218$^{DKO}$ motoneurons (FIG. 29C). The 3'UTR seed match to miR-124 (a pan-neuronal microRNA abundantly expressed in motoneurons and other CNS neurons (25)), but not 3'UTR seed matches to miR-218, was overrepresented in transcripts expressed lower in motoneurons versus purified motoneuron progenitors differentiated from embryonic stem cells (FIGS. 29B and C). We conclude: [1] miR-218 represses a genetic network shared across functionally and spatially distinct neuronal cell types; [2] the low relative expression of this gene network in motoneurons is established by miR-218; and [3] although miR-124 and miR-218 are co-expressed in motoneurons, their regulatory roles differ—miR-124 represses a neuronal progenitor-associated gene network, while miR-218 represses a gene network coordinately expressed by other spinal and cortical neuronal subpopulations.

In summary, we have identified a neuronal gene network that is selectively repressed in motoneurons by a single microRNA. When this network is de-repressed in 218$^{DKO}$ mice, motoneurons exhibit severe neuromuscular junction defects, hyperexcitability and cell loss—the pathological hallmarks of motoneuron diseases such as ALS and SMA (1, 26-28). The link between miR-218 and motoneuron diseases likely extends beyond phenotypic similarities. Patients suffering from motoneuron diseases carry genetic mutations in ubiquitously expressed RNA processing factors (e.g. TAR DNA binding protein-43, fused in sarcoma, survival of motor neuron) or expansion repeats in C9ORF72 that sequester RNA binding proteins (1, 2), but the biological mechanisms that magnify the effects of these changes on motoneurons are unclear. microRNA processing pathways, and specifically, the repression of miR-218's genetic network, might be particularly sensitive to defects in these RNA metabolic pathways thought to underlie motoneuron disease.

REFERENCES

1. X. Paez-Colasante, C. Figueroa-Romero, S. A. Sakowski, S. A. Goutman, E. L. Feldman, Amyotrophic lateral sclerosis: mechanisms and therapeutics in the epigenomic era. Nat Rev Neurol 11, 266-279 (2015).
2. C. Volonte, S. Apolloni, C. Parisi, MicroRNAs: newcomers into the ALS picture. CNS Neurol Disord Drug Targets 14, 194-207 (2015).
3. M. Morlando et al., FUS stimulates microRNA biogenesis by facilitating co-transcriptional Drosha recruitment. EMBO J 31, 4502-4510 (2012).
4. Y. Kawahara, A. Mieda-Sato, TDP-43 promotes microRNA biogenesis as a component of the Drosha and Dicer complexes. Proc Natl Acad Sci USA 109, 3347-3352 (2012).
5. S. Haramati et al., miRNA malfunction causes spinal motor neuron disease. Proc Natl Acad Sci USA 107, 13111-13116 (2010).
6. K. P. Thiebes et al., miR-218 is essential to establish motor neuron fate as a downstream effector of Isl1-Lhx3. Nat Commun 6, 7718 (2015).
7. M. Kapsimali et al., MicroRNAs show a wide diversity of expression profiles in the developing and mature central nervous system. Genome Biol 8, R173 (2007).
8. W. A. Alaynick, T. M. Jessell, S. L. Pfaff, SnapShot: spinal cord development. Cell 146, 178-178 e171 (2011).
9. E. O. Mazzoni et al., Synergistic binding of transcription factors to cell-specific enhancers programs motor neuron identity. Nat Neurosci 16, 1219-1227 (2013).
10. J. A. Vidigal, A. Ventura, The biological functions of miRNAs: lessons from in vivo studies. Trends Cell Biol 25, 137-147 (2015).
11. H. Wang et al., One-step generation of mice carrying mutations in multiple genes by CRISPR/Cas-mediated genome engineering. Cell 153, 910-918 (2013).
12. Y. F. Lu, L. Zhang, M. M. Waye, W. M. Fu, J. F. Zhang, MiR-218 mediates tumorigenesis and metastasis: Perspectives and implications. Exp Cell Res 334, 173-182 (2015).
13. S. van Dongen, C. Abreu-Goodger, A. J. Enright, Detecting microRNA binding and siRNA off-target effects from expression data. Nat Methods 5, 1023-1025 (2008).
14. D. M. Garcia et al., Weak seed-pairing stability and high target-site abundance decrease the proficiency of lsy-6 and other microRNAs. Nat Struct Mot Biol 18, 1139-1146 (2011).
15. B. C. Cheah, S. Vucic, A. V. Krishnan, M. C. Kiernan, Riluzole, neuroprotection and amyotrophic lateral sclerosis. Curr Med Chem 17, 1942-1199 (2010).
16. L. Ma, M. Tessier-Lavigne, Dual branch-promoting and branch-repelling actions of Slit/Robo signaling on peripheral and central branches of developing sensory axons. J Neurosci 27, 6843-6851 (2007).
17. H. Long et al., Conserved roles for Slit and Robo proteins in midline commissural axon guidance. Neuron 42, 213-223 (2004).
18. B. Turgeon, S. Meloche, Interpreting neonatal lethal phenotypes in mouse mutants: insights into gene function and human diseases. Physiol Rev 89, 1-26 (2009).
19. H. Darabid, A. P. Perez-Gonzalez, R. Robitaille, Neuromuscular synaptogenesis: coordinating partners with multiple functions. Nat Rev Neurosci 15, 703-718 (2014).

20. A. C. Kwan, S. B. Dietz, W. W. Webb, R. M. Harris-Warrick, Activity of Hb9 interneurons during fictive locomotion in mouse spinal cord. *J Neurosci* 29, 11601-11613 (2009).
21. D. P. Bartel, MicroRNAs: target recognition and regulatory functions. *Cell* 136, 215-233 (2009).
22. J. Tsang, J. Zhu, A. van Oudenaarden, MicroRNA-mediated feedback and feedforward loops are recurrent network motifs in mammals. *Mol Cell* 26, 753-767 (2007).
23. H. Herranz, S. M. Cohen, MicroRNAs and gene regulatory networks: managing the impact of noise in biological systems. *Genes Dev* 24, 1339-1344 (2010).
24. B. J. Molyneaux et al., DeCoN: genome-wide analysis of in vivo transcriptional dynamics during pyramidal neuron fate selection in neocortex. *Neuron* 85, 275-288 (2015).
25. E. V. Makeyev, J. Zhang, M. A. Carrasco, T. Maniatis, The MicroRNA miR-124 promotes neuronal differentiation by triggering brain-specific alternative pre-mRNA splicing. *Mol Cell* 27, 435-448 (2007).
26. L. R. Fischer et al., Amyotrophic lateral sclerosis is a distal axonopathy: evidence in mice and man. *Exp Neurol* 185, 232-240 (2004).
27. B. J. Wainger et al., Intrinsic membrane hyperexcitability of amyotrophic lateral sclerosis patient-derived motor neurons. *Cell Rep* 7, 1-11 (2014).
28. H. Liu et al., Spinal muscular atrophy patient-derived motor neurons exhibit hyperexcitability. *Sci Rep* 5, 12189 (2015).
29. E. Azim, J. Jiang, B. Alstermark, T. M. Jessell, Skilled reaching relies on a V2a propriospinal internal copy circuit. *Nature* 508, 357-363 (2014).
30. Y. Zhang et al., V3 spinal neurons establish a robust and balanced locomotor rhythm during walking. *Neuron* 60, 84-96 (2008).

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

I claim:

1. A method of treating a human subject diagnosed with or at risk of having a motor neuron disease, comprising administering to a subject in need thereof, a therapeutically effective amount of a composition comprising a nucleic acid encoding a compound that increases miR-218 expression, wherein the nucleic acid encoding a compound that increases miR-218 expression encodes a transcription factor selected from the group consisting of Isl1, Isl2, Lux, Isl-Lhx3 fusion proteins, Phox2a, and a combination thereof.

2. The method of claim 1, wherein the nucleic acid further encodes a miR-218, wherein the miR-218 comprises a nucleic acid selected from the group consisting of 5' UUGUGCUU 3' (SEQ ID NO: 48); 5' UGUGCUU 3' (SEQ ID NO: 49); 5' UUGUGCU 3' (SEQ ID NO: 50); 5' UGUGCU 3' (SEQ ID NO: 51); 5' UUGUGC 3' (SEQ ID NO: 52); and 5' GUGCUU 3' (SEQ ID NO: 53).

3. The method of claim 1, wherein the nucleic acid further encodes a compound that inhibits expression or activity of a miR-218 target nucleic acid or protein encoded therefrom, wherein the miR-218 target nucleic acid comprises a nucleic acid that specifically hybridizes to a miR-218 seed sequence selected from the group consisting of 5' UUGUGCUU 3' (SEQ ID NO: 48); 5' UGUGCUU 3' (SEQ ID NO: 49); 5' UUGUGCU 3' (SEQ ID NO: 50); 5' UGUGCU 3' (SEQ ID NO: 51); 5' UUGUGC 3' (SEQ ID NO: 52); and 5' GUGCUU 3' (SEQ ID NO: 53).

4. The method of claim 3, wherein the compound that inhibits expression or activity of a miR-218 target nucleic acid or protein encoded therefrom, is selected from the group consisting of an RNAi molecule, shRNA molecule, antisense RNA, catalytic RNA, catalytic DNA, protein, or antibody or fragment thereof, specific for a miR-218 target nucleic acid, or protein encoded therefrom.

5. The method of claim 1, wherein the composition is administered in an amount effective to inhibit cell death, increase motor neuron cell function, lengthen subject survival, reduce one or more symptom or sign of a motor neuron disease, or a combination thereof.

6. The method of claim 5, wherein the one or more symptom or sign of a motor neuron disease is selected from the group consisting of a reduction in the ability to make voluntary movements; speech impediments; swallowing impediments; chewing impediments; muscle spasticity; spasms; cramps; fasciculations; breathing impediments; jaw weakness; facial muscle weakness; muscle tone loss; and muscle weakness.

7. The method of claim 1, wherein the motor neuron disease is selected from the group consisting of amyotrophic lateral sclerosis (ALS), primary lateral sclerosis (PLS), progressive muscular atrophy, progressive bulbar palsy, pseudobulbar palsy, spinal muscular atrophy (SMA), post-polio syndrome (PPS), spinal and bulbar muscular atrophy (SBMA), Charcot-Marie-Tooth disease (CMT), and Guillain-Barre syndrome (GBS).

* * * * *

SEQUENCE LISTING

```
<160> NUMBER OF SEQ ID NOS: 122

<210> SEQ ID NO 1
<211> LENGTH: 908
<212> TYPE: DNA
<213> ORGANISM: Mus musculus
<220> FEATURE:
<221> NAME/KEY: misc_feature
<222> LOCATION: (1)..(908)
<223> OTHER INFORMATION: promoter

<400> SEQUENCE: 1
taaacgcccc aatttgctac ttatcaaata gtatacattt ttggctcaga aaaaaacctg      60
atgtctgtat attacttctc aactaaaatc cctcagtcct taactggcat gtgtattagt     120
caaggcatct ttgagaaggg cattatttcc ctacacttag gatggggaaa gagaaattaa     180
aaaggaatcc taaaataggt gcatttaatt ctccccaatt taaatgtaag tggtgcgtct     240
tttaggcaat aatgatatgc cttttagtcc tccattacaa acacttccat cgatgaattt     300
ccttaatgtt gatgatggtt agtgcagttt gagggaatct gtatttattc agaaaatgtt     360
cccatagaat gacctaccag atgggccacg taacaatgca tggagacatc aaaccaccac     420
agacatttgg tgcttagaat aataaaaaga ctataaaatt agattagttg agtctaattt     480
ggaattggta tattccctac gcaccctcac cgctcttggg cagataaagc cttgagattt     540
agcgctgtgt caaagccaag actgtaactt ccagtaaaag ggagccgagg gaggggagc      600 ttgctgggag gtcgcggagg gcagagcagt gacctccaat gatttacagg cctttagctt     660
aatgaaattg tttcagtgac atgacagtaa gagctcgtaa tggattggat gccctaatgt     720
aatgaaatta ctcccttctg cctaaaaaaa aaaaatgcg caattaatat ttactgagac      780
ctgacagcct ttggtgcgct cgctcgcctg tgtagttccc tcagacagtc agagagaaga     840
```

```
gacagagcag cgtggcagac aggcgggctc tgcaggagct cctggcaggg acaagcagag      900
cctgcaag                                                              908

<210> SEQ ID NO 2
<211> LENGTH: 20
<212> TYPE: DNA
<213> ORGANISM: Mus musculus

<400> SEQUENCE: 2
taaacgcccc aatttgctac                                                  20

<210> SEQ ID NO 3
<211> LENGTH: 20
<212> TYPE: DNA
<213> ORGANISM: Mus musculus

<400> SEQUENCE: 3
ttatcaaata gtatacattt                                                  20

<210> SEQ ID NO 4
<211> LENGTH: 20
<212> TYPE: DNA
<213> ORGANISM: Mus musculus

<400> SEQUENCE: 4
ttggctcaga aaaaaacctg                                                  20

<210> SEQ ID NO 5
<211> LENGTH: 20
<212> TYPE: DNA
<213> ORGANISM: Mus musculus

<400> SEQUENCE: 5
atgtctgtat attacttctc                                                  20

<210> SEQ ID NO 6
<211> LENGTH: 20
<212> TYPE: DNA
<213> ORGANISM: Mus musculus

<400> SEQUENCE: 6
aactaaaatc cctcagtcct                                                  20

<210> SEQ ID NO 7
<211> LENGTH: 20
<212> TYPE: DNA
<213> ORGANISM: Mus musculus

<400> SEQUENCE: 7
taactggcat gtgtattagt                                                  20

<210> SEQ ID NO 8
<211> LENGTH: 20
<212> TYPE: DNA
<213> ORGANISM: Mus musculus

<400> SEQUENCE: 8
caaggcatct ttgagaaggg                                                  20

<210> SEQ ID NO 9
<211> LENGTH: 20
<212> TYPE: DNA
```

```
<213> ORGANISM: Mus musculus

<400> SEQUENCE: 9
cattatttcc ctacacttag                                                  20

<210> SEQ ID NO 10
<211> LENGTH: 20
<212> TYPE: DNA
<213> ORGANISM: Mus musculus

<400> SEQUENCE: 10
gatggggaaa gagaaattaa                                                  20

<210> SEQ ID NO 11
<211> LENGTH: 20
<212> TYPE: DNA
<213> ORGANISM: Mus musculus

<400> SEQUENCE: 11
aaaggaatcc taaaataggt                                                  20

<210> SEQ ID NO 12
<211> LENGTH: 19
<212> TYPE: DNA
<213> ORGANISM: Mus musculus

<400> SEQUENCE: 12
gcatttaatt ctccccaat                                                   19

<210> SEQ ID NO 13
<211> LENGTH: 20
<212> TYPE: DNA
<213> ORGANISM: Mus musculus

<400> SEQUENCE: 13
taaatgtaag tggtgcgtct                                                  20

<210> SEQ ID NO 14
<211> LENGTH: 20
<212> TYPE: DNA
<213> ORGANISM: Mus musculus

<400> SEQUENCE: 14
tttaggcaat aatgatatgc                                                  20

<210> SEQ ID NO 15
<211> LENGTH: 20
<212> TYPE: DNA
<213> ORGANISM: Mus musculus

<400> SEQUENCE: 15
cttttagtcc tccattacaa                                                  20

<210> SEQ ID NO 16
<211> LENGTH: 20
<212> TYPE: DNA
<213> ORGANISM: Mus musculus

<400> SEQUENCE: 16
acacttccat cgatgaattt                                                  20

<210> SEQ ID NO 17
<211> LENGTH: 20
```

```
<212> TYPE: DNA
<213> ORGANISM: Mus musculus

<400> SEQUENCE: 17
ccttaatgtt gatgatggtt                                                   20

<210> SEQ ID NO 18
<211> LENGTH: 20
<212> TYPE: DNA
<213> ORGANISM: Mus musculus

<400> SEQUENCE: 18
agtgcagttt gagggaatct                                                   20

<210> SEQ ID NO 19
<211> LENGTH: 20
<212> TYPE: DNA
<213> ORGANISM: Mus musculus

<400> SEQUENCE: 19
gtatttattc agaaaatgtt                                                   20

<210> SEQ ID NO 20
<211> LENGTH: 20
<212> TYPE: DNA
<213> ORGANISM: Mus musculus

<400> SEQUENCE: 20
cccatagaat gacctaccag                                                   20

<210> SEQ ID NO 21
<211> LENGTH: 20
<212> TYPE: DNA
<213> ORGANISM: Mus musculus

<400> SEQUENCE: 21
atgggccacg taacaatgca                                                   20

<210> SEQ ID NO 22
<211> LENGTH: 20
<212> TYPE: DNA
<213> ORGANISM: Mus musculus

<400> SEQUENCE: 22
tggagacatc aaaccaccac                                                   20

<210> SEQ ID NO 23
<211> LENGTH: 20
<212> TYPE: DNA
<213> ORGANISM: Mus musculus

<400> SEQUENCE: 23
agacatttgg tgcttagaat                                                   20

<210> SEQ ID NO 24
<211> LENGTH: 20
<212> TYPE: DNA
<213> ORGANISM: Mus musculus

<400> SEQUENCE: 24
aataaaaaga ctataaaatt                                                   20

<210> SEQ ID NO 25
```

```
<211> LENGTH: 20
<212> TYPE: DNA
<213> ORGANISM: Mus musculus

<400> SEQUENCE: 25
agattagttg agtctaattt                                              20

<210> SEQ ID NO 26
<211> LENGTH: 20
<212> TYPE: DNA
<213> ORGANISM: Mus musculus

<400> SEQUENCE: 26
ggaattggta tattccctac                                              20

<210> SEQ ID NO 27
<211> LENGTH: 20
<212> TYPE: DNA
<213> ORGANISM: Mus musculus

<400> SEQUENCE: 27
gcaccctcac cgctcttggg                                              20

<210> SEQ ID NO 28
<211> LENGTH: 20
<212> TYPE: DNA
<213> ORGANISM: Mus musculus

<400> SEQUENCE: 28
cagataaagc cttgagattt                                              20

<210> SEQ ID NO 29
<211> LENGTH: 20
<212> TYPE: DNA
<213> ORGANISM: Mus musculus

<400> SEQUENCE: 29
agcgctgtgt caaagccaag                                              20

<210> SEQ ID NO 30
<211> LENGTH: 20
<212> TYPE: DNA
<213> ORGANISM: Mus musculus

<400> SEQUENCE: 30
actgtaactt ccagtaaaag                                              20

<210> SEQ ID NO 31
<211> LENGTH: 20
<212> TYPE: DNA
<213> ORGANISM: Mus musculus

<400> SEQUENCE: 31
ggagccgagg gaggggagc                                               20

<210> SEQ ID NO 32
<211> LENGTH: 20
<212> TYPE: DNA
<213> ORGANISM: Mus musculus

<400> SEQUENCE: 32
ttgctgggag gtcgcggagg                                              20
```

```
<210> SEQ ID NO 33
<211> LENGTH: 20
<212> TYPE: DNA
<213> ORGANISM: Mus musculus

<400> SEQUENCE: 33
gcagagcagt gacctccaat                                               20

<210> SEQ ID NO 34
<211> LENGTH: 20
<212> TYPE: DNA
<213> ORGANISM: Mus musculus

<400> SEQUENCE: 34
gatttacagg cctttagctt                                               20

<210> SEQ ID NO 35
<211> LENGTH: 20
<212> TYPE: DNA
<213> ORGANISM: Mus musculus

<400> SEQUENCE: 35
aatgaaattg tttcagtgac                                               20

<210> SEQ ID NO 36
<211> LENGTH: 20
<212> TYPE: DNA
<213> ORGANISM: Mus musculus

<400> SEQUENCE: 36
atgacagtaa gagctcgtaa                                               20

<210> SEQ ID NO 37
<211> LENGTH: 20
<212> TYPE: DNA
<213> ORGANISM: Mus musculus

<400> SEQUENCE: 37
tggattggat gccctaatgt                                               20

<210> SEQ ID NO 38
<211> LENGTH: 20
<212> TYPE: DNA
<213> ORGANISM: Mus musculus

<400> SEQUENCE: 38
aatgaaatta ctcccttctg                                               20

<210> SEQ ID NO 39
<211> LENGTH: 20
<212> TYPE: DNA
<213> ORGANISM: Mus musculus

<400> SEQUENCE: 39
cctaaaaaaa aaaaaatgcg                                               20

<210> SEQ ID NO 40
<211> LENGTH: 20
<212> TYPE: DNA
<213> ORGANISM: Mus musculus

<400> SEQUENCE: 40
caattaatat ttactgagac                                               20
```

```
<210> SEQ ID NO 41
<211> LENGTH: 20
<212> TYPE: DNA
<213> ORGANISM: Mus musculus

<400> SEQUENCE: 41
ctgacagcct ttggtgcgct                                                    20

<210> SEQ ID NO 42
<211> LENGTH: 20
<212> TYPE: DNA
<213> ORGANISM: Mus musculus

<400> SEQUENCE: 42
cgctcgcctg tgtagttccc                                                    20

<210> SEQ ID NO 43
<211> LENGTH: 20
<212> TYPE: DNA
<213> ORGANISM: Mus musculus

<400> SEQUENCE: 43
tcagacagtc agagagaaga                                                    20

<210> SEQ ID NO 44
<211> LENGTH: 20
<212> TYPE: DNA
<213> ORGANISM: Mus musculus

<400> SEQUENCE: 44
gacagagcag cgtggcagac                                                    20

<210> SEQ ID NO 45
<211> LENGTH: 20
<212> TYPE: DNA
<213> ORGANISM: Mus musculus

<400> SEQUENCE: 45
aggcgggctc tgcaggagct                                                    20

<210> SEQ ID NO 46
<211> LENGTH: 20
<212> TYPE: DNA
<213> ORGANISM: Mus musculus

<400> SEQUENCE: 46
cctggcaggg acaagcagag                                                    20

<210> SEQ ID NO 47
<211> LENGTH: 8
<212> TYPE: DNA
<213> ORGANISM: Mus musculus

<400> SEQUENCE: 47 cctgcaag                                                                  8

<210> SEQ ID NO 48
<211> LENGTH: 8
<212> TYPE: RNA
<213> ORGANISM: Mus musculus

<400> SEQUENCE: 48 uugugcuu                                                                  8
```

```
<210> SEQ ID NO 49
<211> LENGTH: 7
<212> TYPE: RNA
<213> ORGANISM: Mus musculus

<400> SEQUENCE: 49 ugugcuu                                                                    7

<210> SEQ ID NO 50
<211> LENGTH: 7
<212> TYPE: RNA
<213> ORGANISM: Mus musculus

<400> SEQUENCE: 50 uugugcu                                                                    7

<210> SEQ ID NO 51
<211> LENGTH: 6
<212> TYPE: RNA
<213> ORGANISM: Mus musculus

<400> SEQUENCE: 51 ugugcu                                                                     6

<210> SEQ ID NO 52
<211> LENGTH: 6
<212> TYPE: RNA
<213> ORGANISM: Mus musculus

<400> SEQUENCE: 52 uugugc                                                                     6

<210> SEQ ID NO 53
<211> LENGTH: 6
<212> TYPE: RNA
<213> ORGANISM: Mus musculus

<400> SEQUENCE: 53 gugcuu                                                                     6

<210> SEQ ID NO 54
<211> LENGTH: 8
<212> TYPE: DNA
<213> ORGANISM: Mus musculus

<400> SEQUENCE: 54 ttgtgctt                                                                   8

<210> SEQ ID NO 55
<211> LENGTH: 7
<212> TYPE: DNA
<213> ORGANISM: Mus musculus

<400> SEQUENCE: 55 tgtgctt                                                                    7

<210> SEQ ID NO 56
<211> LENGTH: 7
<212> TYPE: DNA
<213> ORGANISM: Mus musculus

<400> SEQUENCE: 56
``` ttgtgct                                                         7

<210> SEQ ID NO 57
<211> LENGTH: 6
<212> TYPE: DNA
<213> ORGANISM: Mus musculus

<400> SEQUENCE: 57 tgtgct                                                          6

<210> SEQ ID NO 58
<211> LENGTH: 6
<212> TYPE: DNA
<213> ORGANISM: Mus musculus

<400> SEQUENCE: 58 ttgtgc                                                          6

<210> SEQ ID NO 59
<211> LENGTH: 6
<212> TYPE: DNA
<213> ORGANISM: Mus musculus

<400> SEQUENCE: 59 gtgctt                                                          6

<210> SEQ ID NO 60
<211> LENGTH: 21
<212> TYPE: RNA
<213> ORGANISM: Mus musculus

<400> SEQUENCE: 60
uugugcuuga ucuaaccaug u                                        21

<210> SEQ ID NO 61
<211> LENGTH: 22
<212> TYPE: RNA
<213> ORGANISM: Mus musculus

<400> SEQUENCE: 61
uugugcuuga ucuaaccaug ug                                       22

<210> SEQ ID NO 62
<211> LENGTH: 21
<212> TYPE: DNA
<213> ORGANISM: Mus musculus

<400> SEQUENCE: 62
ttgtgcttga tctaaccatg t                                        21

<210> SEQ ID NO 63
<211> LENGTH: 22
<212> TYPE: DNA
<213> ORGANISM: Mus musculus

<400> SEQUENCE: 63
ttgtgcttga tctaaccatg tg                                       22

<210> SEQ ID NO 64
<211> LENGTH: 110
<212> TYPE: DNA
<213> ORGANISM: Mus musculus

<400> SEQUENCE: 64

```
gaccagtcgc tgcggggctt tcctttgtgc ttgatctaac catgtggtgg aacgatggaa      60
acggaacatg gttctgtcaa gcaccgcgga agcaccgtg  ctctcctgca                110
```

<210> SEQ ID NO 65
<211> LENGTH: 110
<212> TYPE: RNA
<213> ORGANISM: Mus musculus

<400> SEQUENCE: 65

```
gaccagucgc ugcggggcuu uccuuugugc uugaucuaac caugugguggg aacgauggaa     60 acggaacaug guucugucaa gcaccgcgga agcaccgug  cucuccugca                110
```

<210> SEQ ID NO 66
<211> LENGTH: 110
<212> TYPE: DNA
<213> ORGANISM: Mus musculus

<400> SEQUENCE: 66

```
gtgataatgt agcgagattt tctgttgtgc ttgatctaac catgtggttg cgaggtatga      60
gtaaaacatg gttccgtcaa gcaccatgga acgtcacgca gctttctaca                110
```

<210> SEQ ID NO 67
<211> LENGTH: 110
<212> TYPE: RNA
<213> ORGANISM: Mus musculus

<400> SEQUENCE: 67

```
gugauaaugu agcgagauuu ucuguugugc uugaucuaac caugugguug cgagguauga      60
guaaaacaug guuccgucaa gcaccaugga acgucacgca gcuuucuaca                110
```

<210> SEQ ID NO 68
<211> LENGTH: 8
<212> TYPE: DNA
<213> ORGANISM: Mus musculus

<400> SEQUENCE: 68

```
aagcacaa                                                                8
```

<210> SEQ ID NO 69
<211> LENGTH: 7
<212> TYPE: DNA
<213> ORGANISM: Mus musculus

<400> SEQUENCE: 69

```
aagcaca                                                                 7
```

<210> SEQ ID NO 70
<211> LENGTH: 7
<212> TYPE: DNA
<213> ORGANISM: Mus musculus

<400> SEQUENCE: 70

```
agcacaa                                                                 7
```

<210> SEQ ID NO 71
<211> LENGTH: 6
<212> TYPE: DNA
<213> ORGANISM: Mus musculus

<400> SEQUENCE: 71

```
agcaca                                                                6

<210> SEQ ID NO 72
<211> LENGTH: 6
<212> TYPE: DNA
<213> ORGANISM: Mus musculus

<400> SEQUENCE: 72 gcacaa                                                                6

<210> SEQ ID NO 73
<211> LENGTH: 6
<212> TYPE: DNA
<213> ORGANISM: Mus musculus

<400> SEQUENCE: 73 aagcac                                                                6

<210> SEQ ID NO 74
<211> LENGTH: 11
<212> TYPE: DNA
<213> ORGANISM: Mus musculus

<400> SEQUENCE: 74
taatgaaatt g                                                         11

<210> SEQ ID NO 75
<211> LENGTH: 11
<212> TYPE: DNA
<213> ORGANISM: Mus musculus

<400> SEQUENCE: 75
taatgaaatt a                                                         11

<210> SEQ ID NO 76
<211> LENGTH: 33
<212> TYPE: DNA
<213> ORGANISM: Mus musculus

<400> SEQUENCE: 76
tctcgctatg atcatacaca atctgcggga aga                                 33

<210> SEQ ID NO 77
<211> LENGTH: 33
<212> TYPE: DNA
<213> ORGANISM: Mus musculus

<400> SEQUENCE: 77 agagggaga ataacaaatg tccgtaggaa aaa                                  33

<210> SEQ ID NO 78
<211> LENGTH: 33
<212> TYPE: DNA
<213> ORGANISM: Mus musculus

<400> SEQUENCE: 78
tcttcaagca gattgtgtat gatcatagcg aga                                 33

<210> SEQ ID NO 79
<211> LENGTH: 33
<212> TYPE: DNA
<213> ORGANISM: Mus musculus

<400> SEQUENCE: 79
```
tttttcctac ggacatttgt tattctcccc tct                                    33

<210> SEQ ID NO 80
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tctcgctatg atcatacaca atccgtagga aaaa                                   34

<210> SEQ ID NO 81
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tttttcctac ggattgtgta tgatcatagc gaga                                   34

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gatcatacac aatccgtagg aaaaaaaa                                          28

<210> SEQ ID NO 83
<211> LENGTH: 33
<212> TYPE: DNA
<213> ORGANISM: Mus musculus

<400> SEQUENCE: 83
accttgactc tgaccagttg ccgcggggct ttc                                    33

<210> SEQ ID NO 84
<211> LENGTH: 33
<212> TYPE: DNA
<213> ORGANISM: Mus musculus

<400> SEQUENCE: 84
cggggccgtg cttcgagtat ccacattact taa                                    33

<210> SEQ ID NO 85
<211> LENGTH: 33
<212> TYPE: DNA
<213> ORGANISM: Mus musculus

<400> SEQUENCE: 85
gaaagccccg cggcaactgg tcagagtcaa ggt                                    33

<210> SEQ ID NO 86
<211> LENGTH: 33
<212> TYPE: DNA
<213> ORGANISM: Mus musculus

<400> SEQUENCE: 86
ttaagtaatg tggatactcg aagcacggcc ccg         33

<210> SEQ ID NO 87
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
accttgactc tgaccagttg cctcgagtat ccacattact taa         43

<210> SEQ ID NO 88
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ttaagtaatg tggatactcg aggcaactgg tcagagtcaa ggt         43

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tctgaccagt tgcctcgagt atccacat         28

<210> SEQ ID NO 90
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
agatcgggta ccgagaaata cctccgctct g         31

<210> SEQ ID NO 91
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agatcgaccg gtgaaggctc catcttcaat gc         32

<210> SEQ ID NO 92
<211> LENGTH: 23
<212> TYPE: DNA
<213> ORGANISM: Mus musculus

<400> SEQUENCE: 92
tatgatcata cacaatctgc ggg         23

```
<210> SEQ ID NO 93
<211> LENGTH: 23
<212> TYPE: DNA
<213> ORGANISM: Mus musculus

<400> SEQUENCE: 93
ggagaataac aaatgtccgt agg                                              23

<210> SEQ ID NO 94
<211> LENGTH: 23
<212> TYPE: DNA
<213> ORGANISM: Mus musculus

<400> SEQUENCE: 94
gactctgacc agttgccgcg ggg                                              23

<210> SEQ ID NO 95
<211> LENGTH: 23
<212> TYPE: DNA
<213> ORGANISM: Mus musculus

<400> SEQUENCE: 95
taatgtggat actcgaagca cgg                                              23

<210> SEQ ID NO 96
<211> LENGTH: 23
<212> TYPE: DNA
<213> ORGANISM: Mus musculus

<400> SEQUENCE: 96
tgtctccatg cattgttacg tgg                                              23

<210> SEQ ID NO 97
<211> LENGTH: 23
<212> TYPE: DNA
<213> ORGANISM: Mus musculus

<400> SEQUENCE: 97
caggcgagcg agcgcaccaa agg                                              23

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
caccgtatga tcatacacaa tctgc                                            25

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aaacgcagat tgtgtatgat catac                                            25

<210> SEQ ID NO 100
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 100
caccggagaa taacaaatgt ccgt                                                 24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
aaacacggac atttgttatt ctcc                                                 24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
caccgactct gaccagttgc cgcg                                                 24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aaaccgcggc aactggtcag agtc                                                 24

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
caccgtaatg tggatactcg aagca                                                25

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aaactgcttc gagtatccac attac                                                25

<210> SEQ ID NO 106
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 106
caccgtgtct ccatgcattg ttacg                                           25

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aaaccgtaac aatgcatgga gaca                                            24

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
caccgcaggc gagcgagcgc accaa                                           25

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aaacttggtg cgctcgctcg cctg                                            24

<210> SEQ ID NO 110
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
taatacgact cactataggt atgatcatac acaatctgc                            39

<210> SEQ ID NO 111
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
taatacgact cactatagga gaataacaaa tgtccgt                              37

<210> SEQ ID NO 112
<211> LENGTH: 38
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 112
taatacgact cactatagga ctctgaccag ttgccgcg                         38

<210> SEQ ID NO 113
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
taatacgact cactataggt aatgtggata ctcgaagca                        39

<210> SEQ ID NO 114
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
taatacgact cactataggt gtctccatgc attgttacg                        39

<210> SEQ ID NO 115
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
taatacgact cactataggc aggcgagcga gcgcaccaa                        39

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
aaaagcaccg actcggtgcc                                            20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ggcagtcctg tgtcacaaag                                            20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic -continued

```
        primer

<400> SEQUENCE: 118
tggatatcgg ggttcatcgg                                                  20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119 accctcttt caatccctga                                                   20

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
ctttctgctg atccgattct g                                                21

<210> SEQ ID NO 121
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(60)
<223> OTHER INFORMATION: a, c, t, g, unknown or other

<400> SEQUENCE: 121
taatgaaatt gnnnnnnnnn nnnnnnnnnn nnnnnnnnnn nnnnnnnnnn nnnnnnnnnn       60
taatgaaatt a                                                           71

<210> SEQ ID NO 122
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(60)
<223> OTHER INFORMATION: a, c, t, g, unknown or other

<400> SEQUENCE: 122
taatgaaatt gnnnnnnnnn nnnnnnnnnn nnnnnnnnnn nnnnnnnnnn nnnnnnnnnn       60
taatgaaatt g                                                           71
```